(12) United States Patent
Fischer et al.

(10) Patent No.: US 10,280,214 B2
(45) Date of Patent: May 7, 2019

(54) GLYCOSYLATED REPEAT-MOTIF-MOLECULE CONJUGATES

(75) Inventors: Stephan Fischer, Weilheim (DE);
Sabine Imhof-Jung, Planegg (DE);
Erhard Kopetzki, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 13/464,878

(22) Filed: May 4, 2012

(65) Prior Publication Data

US 2012/0309940 A1    Dec. 6, 2012

Related U.S. Application Data

(63) Continuation of application No. PCT/EP2010/006728, filed on Nov. 4, 2010.

(30) Foreign Application Priority Data

Nov. 5, 2009    (EP) ..................... 09013887

(51) Int. Cl.
| | | |
|---|---|---|
| C07K 16/46 | (2006.01) | |
| A61K 39/00 | (2006.01) | |
| A61K 38/00 | (2006.01) | |
| C07K 16/18 | (2006.01) | |
| C07K 16/00 | (2006.01) | |
| C07K 16/32 | (2006.01) | |

(52) U.S. Cl.
CPC .............. *C07K 16/18* (2013.01); *C07K 16/00* (2013.01); *C07K 16/32* (2013.01); *C07K 16/468* (2013.01); *C07K 2317/41* (2013.01); *C07K 2317/52* (2013.01); *C07K 2318/20* (2013.01); *C07K 2319/00* (2013.01); *C07K 2319/21* (2013.01); *C07K 2319/30* (2013.01)

(58) Field of Classification Search
CPC .............. A61K 2300/00; C12Q 1/6883; C12Q 2600/158; C07K 2317/569; C07K 2318/10; C07K 2319/30
See application file for complete search history.

(56) References Cited

U.S. PATENT DOCUMENTS

| | | | |
|---|---|---|---|
| 5,443,953 A | 8/1995 | Hansen et al. | |
| 5,512,473 A | 4/1996 | Brent et al. | |
| 5,582,996 A | 10/1996 | Curtis | |
| 5,624,821 A | 4/1997 | Winter et al. | |
| 5,648,260 A | 7/1997 | Winter et al. | |
| 5,837,821 A | 11/1998 | Wu | |
| 7,951,920 B2* | 5/2011 | Brandt et al. | 530/391.1 |
| 8,193,316 B2 | 6/2012 | Fang et al. | |
| 2003/0143612 A1 | 7/2003 | Ault-Richie et al. | |
| 2004/0132028 A1* | 7/2004 | Stumpp et al. | 435/6 |
| 2004/0203002 A1 | 10/2004 | Choo | |
| 2005/0169925 A1 | 4/2005 | Bardroff et al. | |
| 2005/0260194 A1* | 11/2005 | Peters | C12Y 304/2102 424/133.1 |
| 2006/0234299 A1 | 10/2006 | Stemmer et al. | |
| 2008/0103098 A1 | 1/2008 | Specht | |
| 2008/0063641 A1 | 3/2008 | Huang et al. | |
| 2008/0206201 A1 | 8/2008 | Beier et al. | |
| 2009/0252729 A1* | 10/2009 | Farrington | A61K 47/48338 424/135.1 |
| 2009/0148905 A1 | 11/2009 | Ashman et al. | |
| 2010/0209424 A1* | 8/2010 | Roopenian et al. | 424/134.1 |

FOREIGN PATENT DOCUMENTS

| | | |
|---|---|---|
| EP | 1 403 282 A1 | 3/2004 |
| JP | 2002-526038 A | 8/2002 |
| JP | 2005-507637 A | 3/2005 |
| RU | 2 164 415 C2 | 3/2001 |
| WO | WO-94/10305 A1 | 5/1994 |
| WO | 96/027011 A1 | 9/1996 |
| WO | WO-00/08177 A2 | 2/2000 |
| WO | WO-00/08177 A3 | 2/2000 |
| WO | 02/020565 A2 | 3/2002 |
| WO | WO-02/068650 A2 | 9/2002 |
| WO | WO-02/068650 A3 | 9/2002 |
| WO | 03/070760 A2 | 8/2003 |
| WO | WO-2005/000899 A2 | 1/2005 |
| WO | WO-2005/000899 A3 | 1/2005 |
| WO | 2006/055689 A2 | 5/2006 |
| WO | 2006/083275 A2 | 8/2006 |
| WO | 2007/122511 A2 | 11/2007 |
| WO | 2008/135237 A1 | 11/2008 |
| WO | WO-2008/154226 A1 | 12/2008 |
| WO | WO-2008/154814 A1 | 12/2008 |
| WO | 2009/068649 A2 | 6/2009 |
| WO | WO-2011/054519 A1 | 5/2011 |

OTHER PUBLICATIONS

Glaser et al (Journal of Biological Chemistry, 2005, 280:41494-41503).*
Wright et al (Tibtech, 1997, 15:26-32).*
Zahnd et al. (Journal of Molecular Biology, 2007, 369:1015-1028).*
Dall'Acqua et al. (Journal of Immunology, 2006, 177:1129-1138).*
Liu et al. (mAbs, 2012 4:17-23).*
Brekke et al. (Immunology Today, 1995, 16:85-90).*
Arakawa et al., "Formation of heterodimers from three neurotrophins, nerve growth factor, neurotrophin-3, and brain-derived neurotrophic factor" J. Biol. Chem. 269:27833-27839 (1994).

(Continued)

*Primary Examiner* — Julie Wu
(74) *Attorney, Agent, or Firm* — Morrison & Foerster LLP

(57) ABSTRACT

Herein are reported glycosylated repeat-motif-molecule conjugate of the following formula: (repeat-motif-molecule–linker$_n$)$_m$–conjugation partner–(linker$_o$–repeat-motif-molecule)$_p$, wherein n and o are independently of each other and independently for each value of m and p integer values of 0 or 1, and m and p are independently of each other integer values of 0 or 1 or 2 or 3 or 4 or 5 or 6 or 7, and wherein the repeat-motif-molecule conjugate comprises at least one oligosaccharide attached to a glycosylation site. Also reported are encoding nucleic acids and method for producing these repeat-motif-conjugates in mammalian cells.

8 Claims, 19 Drawing Sheets

Specification includes a Sequence Listing.

(56) References Cited

OTHER PUBLICATIONS

Coleman et al., "Dimerization of the TATA binding protein," J. Biol. Chem. 270:13842-13849 (1995).
De Kruif et al. et al., "Leucine Zipper Dimerized Bivalent and Bispecific scFv Antibodies from a Semi-synthetic Antibody Phage Display Library" J Biol Chem 271(13):7630-7634 (Mar. 29, 1996).
Eggel, A. et al., "DARPins as bispecific receptor antagonists analyzed for immunoglobulin E receptor blockage" Molecular Biology 393:598-607 (Oct. 30, 2009).
Eisenberg et al., "The design, synthesis, and crystallization of an alpha-helical peptide" Protein:16-22 ( 1986).
Forrer et al., "The design, synthesis, and crystallization of an alpha-helical peptide" Chem Bio Chem 5:183-189 ( 2004).
Forrer, P. et al., "A novel strategy to design binding molecules harnessing the modular nature of repeat proteins" FEBS Letters 539:2-6 (Mar. 27, 2003).
Hill et al., "Crystal structure of alpha 1: implications for protein design" Science 249:543-546 (1990).
Ho et al., "Design of a 4-helix bundle protein: synthesis of peptides which self-associate into a helical protein" J. Am. Chern. Soc. 109:6751-6758 ( 1987).
Jefferis, B., "Glycosylation of recombinant antibody therapeutics" Biotechnol Prog 21:11-16 ( 2005).
Jeong et al., "Avimers hold their own," J. Nat. Biotechnol. 23:1493-1494 ( 2005).
Kohl et al., "Designed to be stable: crystal structure of a consensus ankyrin repeat protein" Proc. Natl. Acad. Sci. USA 100:1700-1705 ( 2003).
Kostelny et al., "Formation of a bispecific antibody by the use of leucine zippers" J. Immunol. 148:1547-1553 ( 1992).
Legendre et al., "TEM-1 beta-lactamase as a scaffold for protein recognition and assay" Protein Sci. 11:1506-1518 ( 2002).
Leung et al., "Engineering a unique glycosylation site for site-specific conjugation of haptens to antibody fragments" Journal of Immunology 154:5919-5926 (1995).
Lupas et al., "Predicting Coiled Coils from Protein Sequences" Science 252:1162-1164 (1991).
Meissner, P. et al. et al., "Transient gene expression: recombinant protein production with suspension-adapted HEK293-EBNA cells" Biotechnol Bioeng 75:197-203 ( 2001).
Mueller et al., "The first constant domain (CH1 and CL) of an antibody used as heterodimerization domain for bispecific miniantibodies" FEBS Lett. 422:259-264 ( 1998)
Pack et al., "Improved bivalent miniantibodies, with identical avidity as whole antibodies, produced by high cell density fermentation of *Escherichia coli*" Biotechnol. 11:1271-1277 (1993).
Panni et al., "'In vitro evolution of recognition specificity mediated by SH3 domains reveals target recognition rules" J. Biol. Chem. 277:2166-21674 ( 2002).
Pluckthun and Pack, "New Protein Engineering Approaches to Multivalent and Bispecific Antibody Fragments" Immunotechnology 3:83-105 (Jun. 1997).
Radziejewski et al., "Heterodimers of the neurotrophic factors: formation, isolation, and differential stability" Biochem. 32:13350-13356 ( 1993).
Regan & Degrado, "Characterization of a helical protein designed from first principles." Science 241:976-978 (1988).

Ridgeway et al., "Knobs-into-holes' Engineering of Antibody CH3 Domains for Heavy Chain Heterdimerization" Protein Engineering 9(7):617-621 ( 1996).
Schneider et al., "Mutagenesis and selection of PDZ domains that bind new protein targets" Nat. Biotechnol. 17:170-175 ( 1999).
Shen et al., "Single variable domain antibody as a versatile building block for the construction of IgG-like bispecific antibodies" J Immunol Methods 318:65-74 ( 2007).
Steiner et al., "Efficient selection of DARPins with sub-nanomolar affinities using SRP phage display" J. Mol. Biol. 381:1211-1227 ( 2008).
Stoop et al., "Engineering of a macromolecular scaffold to develop specific protease inhibitors" Nat. Biotechnol. 21:1063-1068 ( 2003).
Stumpp, M. et al., "DARPins: A new generation of protein 'therapeutics'" Drug Discovery Today 13:695-701 (Aug. 1, 2008).
Vijayalakshmi, "Antibody purification methods" Appl Biochem Biotech 75:93-102 (1998).
Vita et al., "Scorpion toxins as natural scaffolds for protein engineering" Proc. Natl. Acad. Sci. USA 92:6404-6408 ( 1995).
Winkler, J. et al., "EpCAM-targeted delivery of nanocomplexed siRNA to tumor cells with designed ankyrin repeat proteins" Molecular Cancer Therapeutics 8(9):2674-2683 (Sep. 2009).
Zahnd et al., "A designed ankyrin repeat protein evolved to picomolar affinity to Her2" J. Mol Biol. 369:1015-1028 ( 2007).
International Search Report dated Jan. 14, 2011, for PCT Patent Application No. PCT/EP2010/006728, filed on Nov. 4, 2010, four pages.
Written Opinion dated Jan. 14, 2011, for PCT Patent Application No. PCT/EP2010/006728, filed on Nov. 4, 2010, eleven pages.
Brekke et al., "The Structural Requirements for Complement Activation by IgG: Does it Hinge on the Hinge?" *Immunology Today* 16(2):85-90 ( 1995).
Drew, D.R. et al. "The Human IgG3 Hinge Mediates the Formation of Antigen Dimers That Enhance Humoral Immune Responses to DNA Immunisation," Vaccine 19:4115-4120 (2001).
Olafsen, T. et al. "Generation of Single-Chain Fv Fragments and Multivalent Derivatives scFv-Fc and scFv-CH3 (Minibodies)," Chapter 6 in Antibody Engineering, Kontermann, R. et al. Eds., 2:69-72, 75-79, 82-84. (2010).
Tarantul, V.Z. "Languages of Slavic Cultures," Glossary of Biotechnology Terms, Moscow, Russia p. 213 (2009). (Translation of p. 213 Abstract Only.).
Ashkenazi et al. "Protection Against Endotoxic Shock by a Tumor Necrosis Factor Receptor Immunoadhesin," *Proc. Natl. Acad. Sci. USA*, 88:10535-10539, (Dec. 1991).
Swartz et al. "Enigneering Cell Extracts for Efficient Protein Synthesis," *Meeting Abstracts for the Society for Biotechnology*, Japan, Abstract No. 545, p. 84, (2002). (English Translation of the Abstract).
European Office Action dated Apr. 2, 2015, for EP Patent Application No. 10779694.8, filed on Nov. 4, 2010, seven pages.
Song et al. "Increased Refolding Yield of Disulfide Bond Bridged Fab-Toxin Homodimers by the Insertion of CH3 Domains," *J. Microbiol. Biotechnol.* 16(7):1104-1110, (2006).
Wu et al. "Multimerization fo a Chimeric Anti-CD20 Single-Chain Fv-Fc Fusion Protein is Mediated Through Variable Domain Exchange," *Prot. Eng.* 14(12):1025-1033, (2001).
European Office Action dated Apr. 8, 2016, for EP Patent Application No. 10779694.8, filed on Nov. 4, 2010, eight pages.

* cited by examiner

```
                         SEQUENCE LISTING

<160> NUMBER OF SEQ ID NOS: 66

<210> SEQ ID NO 1
<211> LENGTH: 30
<212> TYPE: PRT
<213> ORGANISM: Artificial Sequence
<220> FEATURE:
<223> OTHER INFORMATION: consensus sequence 1
<220> FEATURE:
<221> NAME/KEY: MISC_FEATURE
<222> LOCATION: (5)..(5)
<223> OTHER INFORMATION: proline or alanine
<220> FEATURE:
<221> NAME/KEY: MISC_FEATURE
<222> LOCATION: (10)..(10)
<223> OTHER INFORMATION: alanine or valine
<220> FEATURE:
<221> NAME/KEY: MISC_FEATURE
<222> LOCATION: (14)..(14)
<223> OTHER INFORMATION: histidine or asparagine
<220> FEATURE:
<221> NAME/KEY: MISC_FEATURE
<222> LOCATION: (17)..(17)
<223> OTHER INFORMATION: isoleucine or valine
<220> FEATURE:
<221> NAME/KEY: MISC_FEATURE
<222> LOCATION: (22)..(22)
<223> OTHER INFORMATION: leucine or isoleucine
<220> FEATURE:
<221> NAME/KEY: MISC_FEATURE
<222> LOCATION: (27)..(27)
<223> OTHER INFORMATION: aspartic acid or asparagine

<400> SEQUENCE: 1

Asp Gly Asn Thr Xaa Leu His Leu Ala Xaa Glu Asn Gly Xaa Leu Glu
1               5                   10                  15

Xaa Val Lys Leu Leu Xaa Glu Ala Gly Ala Xaa Ile Asn Ala
            20                  25                  30

<210> SEQ ID NO 2
<211> LENGTH: 33
<212> TYPE: PRT
<213> ORGANISM: Artificial Sequence
<220> FEATURE:
<223> OTHER INFORMATION: consensus sequence 2

<400> SEQUENCE: 2

Asp Ser Asp Gly Asn Thr Pro Leu His Leu Ala Ala Glu Asn Gly Gln
1               5                   10                  15
```

-continued

Leu Glu Val Val Lys Leu Leu Leu Glu Ala Gly Ala Asp Val Asn Ala
               20                  25                  30

Arg

<210> SEQ ID NO 3
<211> LENGTH: 33
<212> TYPE: PRT
<213> ORGANISM: Artificial Sequence
<220> FEATURE:
<223> OTHER INFORMATION: consensus sequence 3
<220> FEATURE:
<221> NAME/KEY: MISC_FEATURE
<222> LOCATION: (1)..(1)
<223> OTHER INFORMATION: aspartic acid or threonine
<220> FEATURE:
<221> NAME/KEY: MISC_FEATURE
<222> LOCATION: (10)..(10)
<223> OTHER INFORMATION: leucine or isoleucine
<220> FEATURE:
<221> NAME/KEY: MISC_FEATURE
<222> LOCATION: (29)..(29)
<223> OTHER INFORMATION: aspartic acid or asparagine
<220> FEATURE:
<221> NAME/KEY: MISC_FEATURE
<222> LOCATION: (30)..(30)
<223> OTHER INFORMATION: valine or isoleucine

<400> SEQUENCE: 3

Xaa Lys Asn Gly Leu Thr Pro Leu His Xaa Ala Ala Gln Glu Gly His
1               5                   10                  15

Leu Glu Val Val Lys Leu Leu Leu Glu Asn Gly Ala Xaa Xaa Asn Ala
               20                  25                  30

Lys

<210> SEQ ID NO 4
<211> LENGTH: 33
<212> TYPE: PRT
<213> ORGANISM: Artificial Sequence
<220> FEATURE:
<223> OTHER INFORMATION: consensus sequence 4
<220> FEATURE:
<221> NAME/KEY: MISC_FEATURE
<222> LOCATION: (1)..(33)
<223> OTHER INFORMATION: Xaa denoting variable position

<400> SEQUENCE: 4

Asp Xaa Xaa Gly Xaa Thr Pro Leu His Leu Ala Ala Xaa Xaa Gly His
1               5                   10                  15

Leu Glu Ile Val Glu Val Leu Leu Lys Xaa Gly Ala Asp Val Asn Ala
               20                  25                  30

Xaa

<210> SEQ ID NO 5
<211> LENGTH: 33
<212> TYPE: PRT
<213> ORGANISM: Artificial Sequence
<220> FEATURE:
<223> OTHER INFORMATION: consensus sequence 5

<400> SEQUENCE: 5

Ala Asp Val Asn Ala Lys Asp Lys Asp Gly Tyr Thr Pro Leu His Leu
1               5                   10                  15

Ala Ala Arg Glu Gly His Leu Glu Ile Val Glu Val Leu Leu Lys Ala
               20                  25                  30

Gly

<210> SEQ ID NO 6
<211> LENGTH: 33
<212> TYPE: PRT
<213> ORGANISM: Artificial Sequence
<220> FEATURE:
<223> OTHER INFORMATION: consensus sequence 6
<220> FEATURE:
<221> NAME/KEY: MISC_FEATURE
<222> LOCATION: (1)..(33)
<223> OTHER INFORMATION: Xaa denoting variable position

<400> SEQUENCE: 6

Asp Xaa Xaa Gly Xaa Thr Pro Leu His Leu Ala Ala Xaa Xaa Gly Pro
1               5                   10                  15

Xaa Pro Ala Val Pro Xaa Leu Leu Pro Xaa Gly Ala Asp Val Asn Ala
            20                  25                  30

Xaa

<210> SEQ ID NO 7
<211> LENGTH: 33
<212> TYPE: PRT
<213> ORGANISM: Artificial Sequence
<220> FEATURE:
<223> OTHER INFORMATION: consensus sequence 7
<220> FEATURE:
<221> NAME/KEY: MISC_FEATURE
<222> LOCATION: (1)..(33)
<223> OTHER INFORMATION: Xaa denoting variable position

<400> SEQUENCE: 7

Asp Xaa Xaa Gly Xaa Thr Pro Leu His Leu Ala Xaa Xaa Xaa Gly Xaa
1               5                   10                  15

Xaa Xaa Val Val Xaa Leu Leu Leu Xaa Xaa Gly Ala Asp Val Asn Ala
            20                  25                  30

Xaa

<210> SEQ ID NO 8
<211> LENGTH: 33
<212> TYPE: PRT
<213> ORGANISM: Artificial Sequence
<220> FEATURE:
<223> OTHER INFORMATION: consensus sequence 8
<220> FEATURE:
<221> NAME/KEY: MISC_FEATURE
<222> LOCATION: (1)..(33)
<223> OTHER INFORMATION: Xaa denoting variable position

<400> SEQUENCE: 8

Asp Xaa Xaa Gly Xaa Thr Pro Leu His Leu Ala Xaa Xaa Xaa Gly Xaa
1               5                   10                  15

Xaa Xaa Ile Val Xaa Val Leu Leu Xaa Xaa Gly Ala Asp Val Asn Ala
            20                  25                  30

Xaa

<210> SEQ ID NO 9
<211> LENGTH: 33
<212> TYPE: PRT
<213> ORGANISM: Artificial Sequence
<220> FEATURE:
<223> OTHER INFORMATION: consensus sequence 9
<220> FEATURE:
<221> NAME/KEY: MISC_FEATURE
<222> LOCATION: (1)..(25)
<223> OTHER INFORMATION: Xaa denotes amino acid selected from A, D, E,
      F, H, I, K, L, M, N, Q, R, S, T, V, W and Y
<220> FEATURE:

```
<221> NAME/KEY: MISC_FEATURE
<222> LOCATION: (26)..(26)
<223> OTHER INFORMATION: Xaa denotes amino acid selected from H, N and Y
<220> FEATURE:
<221> NAME/KEY: MISC_FEATURE
<222> LOCATION: (27)..(33)
<223> OTHER INFORMATION: Xaa denotes amino acid selected from A, D, E,
      F, H, I, K, L, M, N, Q, R, S, T, V, W and Y

<400> SEQUENCE: 9

Asp Xaa Xaa Gly Xaa Thr Pro Leu His Leu Ala Ala Xaa Xaa Gly His
1               5                   10                  15

Leu Glu Ile Val Glu Val Leu Leu Lys Xaa Gly Ala Asp Val Asn Ala
            20                  25                  30

Xaa

<210> SEQ ID NO 10
<211> LENGTH: 130
<212> TYPE: PRT
<213> ORGANISM: Artificial Sequence
<220> FEATURE:
<223> OTHER INFORMATION: model repeat-motif-molecule H10-2-G3 with
      C-terminal hexa-histidine-tag

<400> SEQUENCE: 10

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Glu Tyr Gly Leu Thr Pro Leu Tyr Leu Ala Thr Ala His Gly His Leu
        35                  40                  45

Glu Ile Val Glu Val Leu Leu Lys Asn Gly Ala Asp Val Asn Ala Val
    50                  55                  60

Asp Ala Ile Gly Phe Thr Pro Leu His Leu Ala Ala Phe Ile Gly His
65                  70                  75                  80

Leu Glu Ile Ala Glu Val Leu Leu Lys His Gly Ala Asp Val Asn Ala
                85                  90                  95

Gln Asp Lys Phe Gly Lys Thr Ala Phe Asp Ile Ser Ile Gly Asn Gly
            100                 105                 110

Asn Glu Asp Leu Ala Glu Ile Leu Gln Gly Ser Gly His His His His
        115                 120                 125

His His
    130

<210> SEQ ID NO 11
<211> LENGTH: 352
<212> TYPE: PRT
<213> ORGANISM: Artificial Sequence
<220> FEATURE:
<223> OTHER INFORMATION: model repeat-motif-molecule H10-2-G3 with
      C-terminally conjugated IgG1 Fc-part

<400> SEQUENCE: 11

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Glu Tyr Gly Leu Thr Pro Leu Tyr Leu Ala Thr Ala His Gly His Leu
        35                  40                  45

Glu Ile Val Glu Val Leu Leu Lys Asn Gly Ala Asp Val Asn Ala Val
    50                  55                  60
```

```
Asp Ala Ile Gly Phe Thr Pro Leu His Leu Ala Ala Phe Ile Gly His
 65                  70                  75                  80

Leu Glu Ile Ala Glu Val Leu Leu Lys His Gly Ala Asp Val Asn Ala
                 85                  90                  95

Gln Asp Lys Phe Gly Lys Thr Ala Phe Asp Ile Ser Ile Gly Asn Gly
            100                 105                 110

Asn Glu Asp Leu Ala Glu Ile Leu Gln Pro Lys Ser Cys Asp Lys Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 12
<211> LENGTH: 163
<212> TYPE: PRT
<213> ORGANISM: Artificial Sequence
<220> FEATURE:
<223> OTHER INFORMATION: model repeat-motif-molecule 9-26 with
      C-terminally conjugated hexa-histidine-tag

<400> SEQUENCE: 12

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Phe Tyr Gly Ile Thr Pro Leu His Leu Ala Ala Tyr Gly His Leu
        35                  40                  45

Glu Ile Val Glu Val Leu Leu Lys His Gly Ala Asp Val Asn Ala His
    50                  55                  60

Asp Trp Asn Gly Trp Thr Pro Leu His Leu Ala Ala Lys Tyr Gly His
```

```
                65                  70                  75                  80
Leu Glu Ile Val Glu Val Leu Lys His Gly Ala Asp Val Asn Ala
                    85                  90                  95

Ile Asp Asn Ala Gly Lys Thr Pro Leu His Leu Ala Ala His Gly
                100                 105                 110

His Leu Glu Ile Val Glu Val Leu Lys Tyr Gly Ala Asp Val Asn
                115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Gly Ser Gly His His His
145                 150                 155                 160

His His His

<210> SEQ ID NO 13
<211> LENGTH: 385
<212> TYPE: PRT
<213> ORGANISM: Artificial Sequence
<220> FEATURE:
<223> OTHER INFORMATION: model repeat-motif-molecule 9-26 with
      C-terminally conjugated IgG1 Fc-part

<400> SEQUENCE: 13

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
                20                  25                  30

Phe Tyr Gly Ile Thr Pro Leu His Leu Ala Ala Ala Tyr Gly His Leu
            35                  40                  45

Glu Ile Val Glu Val Leu Leu Lys His Gly Ala Asp Val Asn Ala His
        50                  55                  60

Asp Trp Asn Gly Trp Thr Pro Leu His Leu Ala Ala Lys Tyr Gly His
65              70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala Ala His Gly
                100                 105                 110

His Leu Glu Ile Val Glu Val Leu Leu Lys Tyr Gly Ala Asp Val Asn
                115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Pro Lys Ser Cys Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
                180                 185                 190

Arg Thr Pro Glu Val Thr Cys Val Val Val Asp Val Ser His Glu Asp
            195                 200                 205

Pro Glu Val Lys Phe Asn Trp Tyr Val Asp Gly Val Glu Val His Asn
            210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
```

```
                     260                 265                 270
Thr Ile Ser Lys Ala Lys Gly Gln Pro Arg Glu Pro Gln Val Tyr Thr
            275                 280                 285

Leu Pro Pro Ser Arg Asp Glu Leu Thr Lys Asn Gln Val Ser Leu Thr
        290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 14
<211> LENGTH: 5
<212> TYPE: PRT
<213> ORGANISM: Artificial Sequence
<220> FEATURE:
<223> OTHER INFORMATION: linker 1

<400> SEQUENCE: 14

Gly Gly Gly Gly Ser
1               5

<210> SEQ ID NO 15
<211> LENGTH: 5
<212> TYPE: PRT
<213> ORGANISM: Artificial Sequence
<220> FEATURE:
<223> OTHER INFORMATION: linker 2

<400> SEQUENCE: 15

Gln Gln Gln Gln Gly
1               5

<210> SEQ ID NO 16
<211> LENGTH: 5
<212> TYPE: PRT
<213> ORGANISM: Artificial Sequence
<220> FEATURE:
<223> OTHER INFORMATION: linker 3

<400> SEQUENCE: 16

Ser Ser Ser Ser Gly
1               5

<210> SEQ ID NO 17
<211> LENGTH: 17
<212> TYPE: PRT
<213> ORGANISM: Artificial Sequence
<220> FEATURE:
<223> OTHER INFORMATION: linker 4

<400> SEQUENCE: 17

Gly Ser Ser Ser Ser Ser Ser Ser Ser Ser Ser Ser Ser Ser Ser Ser
1               5                   10                  15

Gly
```

<210> SEQ ID NO 18
<211> LENGTH: 18
<212> TYPE: PRT
<213> ORGANISM: Artificial Sequence
<220> FEATURE:
<223> OTHER INFORMATION: linker 5

<400> SEQUENCE: 18

Gly Gln Gln Gln Gln Gly Gln Gln Gln Gly Gln Gln Gln Gln Gly
1               5                   10                  15

Asn Asn

<210> SEQ ID NO 19
<211> LENGTH: 7
<212> TYPE: PRT
<213> ORGANISM: Artificial Sequence
<220> FEATURE:
<223> OTHER INFORMATION: linker 6

<400> SEQUENCE: 19

Leu Ser Leu Ser Pro Gly Lys
1               5

<210> SEQ ID NO 20
<211> LENGTH: 8
<212> TYPE: PRT
<213> ORGANISM: Artificial Sequence
<220> FEATURE:
<223> OTHER INFORMATION: linker 7

<400> SEQUENCE: 20

Leu Ser Pro Asn Arg Gly Glu Cys
1               5

<210> SEQ ID NO 21
<211> LENGTH: 6
<212> TYPE: PRT
<213> ORGANISM: Artificial Sequence
<220> FEATURE:
<223> OTHER INFORMATION: linker 8

<400> SEQUENCE: 21

Leu Ser Leu Ser Gly Gly
1               5

<210> SEQ ID NO 22
<211> LENGTH: 7
<212> TYPE: PRT
<213> ORGANISM: Artificial Sequence
<220> FEATURE:
<223> OTHER INFORMATION: linker 9

<400> SEQUENCE: 22

Leu Ser Leu Ser Pro Gly Gly
1               5

<210> SEQ ID NO 23
<211> LENGTH: 15
<212> TYPE: PRT
<213> ORGANISM: Artificial Sequence
<220> FEATURE:
<223> OTHER INFORMATION: linker 10

<400> SEQUENCE: 23

Gly Gly Gly Ser Gly Gly Gly Gly Ser Gly Gly Gly Gly Ser Gly

```
                1               5                  10                 15
```

<210> SEQ ID NO 24
<211> LENGTH: 16
<212> TYPE: PRT
<213> ORGANISM: Artificial Sequence
<220> FEATURE:
<223> OTHER INFORMATION: linker 11

<400> SEQUENCE: 24

```
Gly Gly Gly Ser Gly Gly Gly Ser Gly Gly Gly Ser Gly Gly Gly Gly
1               5                  10                 15
```

<210> SEQ ID NO 25
<211> LENGTH: 4
<212> TYPE: PRT
<213> ORGANISM: Artificial Sequence
<220> FEATURE:
<223> OTHER INFORMATION: linker 12

<400> SEQUENCE: 25

```
Gly Gly Gly Ser
1
```

<210> SEQ ID NO 26
<211> LENGTH: 8
<212> TYPE: PRT
<213> ORGANISM: Artificial Sequence
<220> FEATURE:
<223> OTHER INFORMATION: linker 13

<400> SEQUENCE: 26

```
Gly Gly Gly Ser Gly Gly Gly Ser
1               5
```

<210> SEQ ID NO 27
<211> LENGTH: 12
<212> TYPE: PRT
<213> ORGANISM: Artificial Sequence
<220> FEATURE:
<223> OTHER INFORMATION: linker 14

<400> SEQUENCE: 27

```
Gly Gly Gly Ser Gly Gly Gly Ser Gly Gly Gly Ser
1               5                  10
```

<210> SEQ ID NO 28
<211> LENGTH: 16
<212> TYPE: PRT
<213> ORGANISM: Artificial Sequence
<220> FEATURE:
<223> OTHER INFORMATION: linker 15

<400> SEQUENCE: 28

```
Gly Gly Gly Ser Gly Gly Gly Ser Gly Gly Gly Ser Gly Gly Gly Ser
1               5                  10                 15
```

<210> SEQ ID NO 29
<211> LENGTH: 20
<212> TYPE: PRT
<213> ORGANISM: Artificial Sequence
<220> FEATURE:
<223> OTHER INFORMATION: linker 16

<400> SEQUENCE: 29

```
Gly Gly Gly Ser Gly Gly Gly Ser Gly Gly Gly Ser Gly Gly Gly Ser
1               5                  10                 15
```

```
Gly Gly Gly Ser
        20

<210> SEQ ID NO 30
<211> LENGTH: 10
<212> TYPE: PRT
<213> ORGANISM: Artificial Sequence
<220> FEATURE:
<223> OTHER INFORMATION: linker 17

<400> SEQUENCE: 30

Gly Gly Gly Gly Ser Gly Gly Gly Gly Ser
1               5                   10

<210> SEQ ID NO 31
<211> LENGTH: 15
<212> TYPE: PRT
<213> ORGANISM: Artificial Sequence
<220> FEATURE:
<223> OTHER INFORMATION: linker 18

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 20
<212> TYPE: PRT
<213> ORGANISM: Artificial Sequence
<220> FEATURE:
<223> OTHER INFORMATION: linker 19

<400> SEQUENCE: 32

Gly Gly Gly Gly Ser Gly Gly Gly Gly Ser Gly Gly Gly Gly Ser Gly
1               5                   10                  15

Gly Gly Gly Ser
        20

<210> SEQ ID NO 33
<211> LENGTH: 25
<212> TYPE: PRT
<213> ORGANISM: Artificial Sequence
<220> FEATURE:
<223> OTHER INFORMATION: linker 20

<400> SEQUENCE: 33

Gly Gly Gly Gly Ser Gly Gly Gly Gly Ser Gly Gly Gly Gly Ser Gly
1               5                   10                  15

Gly Gly Gly Ser Gly Gly Gly Gly Ser
        20                  25

<210> SEQ ID NO 34
<211> LENGTH: 352
<212> TYPE: PRT
<213> ORGANISM: Artificial Sequence
<220> FEATURE:
<223> OTHER INFORMATION: Model repeat-motif-molecule H10-2-G3 with
      C-terminally conjugated IgG1 Fc-part with two disulfide bonds in
      the hinge region

<400> SEQUENCE: 34

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30
```

```
Glu Tyr Gly Leu Thr Pro Leu Tyr Leu Ala Thr Ala His Gly His Leu
            35                  40                  45

Glu Ile Val Glu Val Leu Leu Lys Asn Gly Ala Asp Val Asn Ala Val
 50                  55                  60

Asp Ala Ile Gly Phe Thr Pro Leu His Leu Ala Ala Phe Ile Gly His
 65                  70                  75                  80

Leu Glu Ile Ala Glu Val Leu Leu Lys His Gly Ala Asp Val Asn Ala
                85                  90                  95

Gln Asp Lys Phe Gly Lys Thr Ala Phe Asp Ile Ser Ile Gly Asn Gly
                100                 105                 110

Asn Glu Asp Leu Ala Glu Ile Leu Gln Pro Lys Ser Ser Asp Lys Thr
            115                 120                 125

His Thr Cys Pro Pro Cys Pro Ala Pro Glu Leu Leu Gly Gly Pro Ser
            130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
            210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
                260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Val Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 35
<211> LENGTH: 385
<212> TYPE: PRT
<213> ORGANISM: Artificial Sequence
<220> FEATURE:
<223> OTHER INFORMATION: Model repeat-motif-molecule 9-26 with
      C-terminally conjugated IgG1 Fc-part with two disulfide bonds in
      the hinge region

<400> SEQUENCE: 35

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
                20                  25                  30
```

```
Phe Tyr Gly Ile Thr Pro Leu His Leu Ala Ala Ala Tyr Gly His Leu
             35                  40                  45
Glu Ile Val Glu Val Leu Leu Lys His Gly Ala Asp Val Asn Ala His
 50                  55                  60
Asp Trp Asn Gly Trp Thr Pro Leu His Leu Ala Ala Lys Tyr Gly His
 65                  70                  75                  80
Leu Glu Ile Val Glu Val Leu Leu Lys His Gly Ala Asp Val Asn Ala
                 85                  90                  95
Ile Asp Asn Ala Gly Lys Thr Pro Leu His Leu Ala Ala His Gly
            100                 105                 110
His Leu Glu Ile Val Glu Val Leu Leu Lys Tyr Gly Ala Asp Val Asn
            115                 120                 125
Ala Gln Asp Lys Phe Gly Lys Thr Ala Phe Asp Ile Ser Ile Asp Asn
            130                 135                 140
Gly Asn Glu Asp Leu Ala Glu Ile Leu Gln Pro Lys Ser Ser Asp Lys
145                 150                 155                 160
Thr His Thr Cys Pro Pro Cys Pro Ala Pro Glu Leu Leu Gly Gly Pro
                165                 170                 175
Ser Val Phe Leu Phe Pro Pro Lys Pro Lys Asp Thr Leu Met Ile Ser
            180                 185                 190
Arg Thr Pro Glu Val Thr Cys Val Val Val Asp Val Ser His Glu Asp
            195                 200                 205
Pro Glu Val Lys Phe Asn Trp Tyr Val Asp Gly Val Glu Val His Asn
            210                 215                 220
Ala Lys Thr Lys Pro Arg Glu Glu Gln Tyr Asn Ser Thr Tyr Arg Val
225                 230                 235                 240
Val Ser Val Leu Thr Val Leu His Gln Asp Trp Leu Asn Gly Lys Glu
                245                 250                 255
Tyr Lys Cys Lys Val Ser Asn Lys Ala Leu Pro Ala Pro Ile Glu Lys
            260                 265                 270
Thr Ile Ser Lys Ala Lys Gly Gln Pro Arg Glu Pro Gln Val Tyr Thr
            275                 280                 285
Leu Pro Pro Ser Arg Asp Glu Leu Thr Lys Asn Gln Val Ser Leu Thr
290                 295                 300
Cys Leu Val Lys Gly Phe Tyr Pro Ser Asp Ile Ala Val Glu Trp Glu
305                 310                 315                 320
Ser Asn Gly Gln Pro Glu Asn Asn Tyr Lys Thr Thr Pro Pro Val Leu
                325                 330                 335
Asp Ser Asp Gly Ser Phe Phe Leu Tyr Ser Lys Leu Thr Val Asp Lys
            340                 345                 350
Ser Arg Trp Gln Gln Gly Asn Val Phe Ser Cys Ser Val Met His Glu
            355                 360                 365
Ala Leu His Asn His Tyr Thr Gln Lys Ser Leu Ser Leu Ser Pro Gly
            370                 375                 380
Lys
385

<210> SEQ ID NO 36
<211> LENGTH: 352
<212> TYPE: PRT
<213> ORGANISM: Artificial Sequence
<220> FEATURE:
<223> OTHER INFORMATION: Model repeat-motif-molecule H10-2-G3 with
      C-terminally conjugated IgG1 Fc-part with CH3-knob-domain

<400> SEQUENCE: 36
```

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Glu Tyr Gly Leu Thr Pro Leu Tyr Leu Ala Thr Ala His Gly His Leu
        35                  40                  45

Glu Ile Val Glu Val Leu Leu Lys Asn Gly Ala Asp Val Asn Ala Val
50                  55                  60

Asp Ala Ile Gly Phe Thr Pro Leu His Leu Ala Ala Phe Ile Gly His
65                  70                  75                  80

Leu Glu Ile Ala Glu Val Leu Leu Lys His Gly Ala Asp Val Asn Ala
                85                  90                  95

Gln Asp Lys Phe Gly Lys Thr Ala Phe Asp Ile Ser Ile Gly Asn Gly
                100                 105                 110

Asn Glu Asp Leu Ala Glu Ile Leu Gln Pro Lys Ser Cys Asp Lys Thr
            115                 120                 125

His Thr Cys Pro Pro Cys Pro Ala Pro Glu Leu Leu Gly Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
        210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Cys Arg Asp Glu Leu Thr Lys Asn Gln Val Ser Leu Trp Cys
                260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Val Leu Asp
        290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
                340                 345                 350

<210> SEQ ID NO 37
<211> LENGTH: 385
<212> TYPE: PRT
<213> ORGANISM: Artificial Sequence
<220> FEATURE:
<223> OTHER INFORMATION: Model repeat-motif-molecule 9-26 with
      C-terminally conjugated IgG1 Fc-part with CH3-hole-domain

<400> SEQUENCE: 37

Asp Leu Gly Lys Lys Leu Leu Glu Ala Ala Arg Ala Gly Gln Asp Asp

```
  1               5                  10                 15
Glu Val Arg Ile Leu Met Ala Asn Gly Ala Asp Val Asn Ala Lys Asp
            20                  25                  30
Phe Tyr Gly Ile Thr Pro Leu His Leu Ala Ala Tyr Gly His Leu
            35                  40                  45
Glu Ile Val Glu Val Leu Leu Lys His Gly Ala Asp Val Asn Ala His
 50                  55                  60
Asp Trp Asn Gly Trp Thr Pro Leu His Leu Ala Ala Lys Tyr Gly His
 65                  70                  75                  80
Leu Glu Ile Val Glu Val Leu Leu Lys His Gly Ala Asp Val Asn Ala
                 85                  90                  95
Ile Asp Asn Ala Gly Lys Thr Pro Leu His Leu Ala Ala Ala His Gly
                100                 105                 110
His Leu Glu Ile Val Glu Val Leu Leu Lys Tyr Gly Ala Asp Val Asn
                115                 120                 125
Ala Gln Asp Lys Phe Gly Lys Thr Ala Phe Asp Ile Ser Ile Asp Asn
            130                 135                 140
Gly Asn Glu Asp Leu Ala Glu Ile Leu Gln Pro Lys Ser Cys Asp Lys
145                 150                 155                 160
Thr His Thr Cys Pro Pro Cys Pro Ala Pro Glu Leu Leu Gly Gly Pro
                165                 170                 175
Ser Val Phe Leu Phe Pro Pro Lys Pro Lys Asp Thr Leu Met Ile Ser
            180                 185                 190
Arg Thr Pro Glu Val Thr Cys Val Val Val Asp Val Ser His Glu Asp
            195                 200                 205
Pro Glu Val Lys Phe Asn Trp Tyr Val Asp Gly Val Glu Val His Asn
 210                 215                 220
Ala Lys Thr Lys Pro Arg Glu Glu Gln Tyr Asn Ser Thr Tyr Arg Val
225                 230                 235                 240
Val Ser Val Leu Thr Val Leu His Gln Asp Trp Leu Asn Gly Lys Glu
                245                 250                 255
Tyr Lys Cys Lys Val Ser Asn Lys Ala Leu Pro Ala Pro Ile Glu Lys
            260                 265                 270
Thr Ile Ser Lys Ala Lys Gly Gln Pro Arg Glu Pro Gln Val Cys Thr
            275                 280                 285
Leu Pro Pro Ser Arg Asp Glu Leu Thr Lys Asn Gln Val Ser Leu Ser
 290                 295                 300
Cys Ala Val Lys Gly Phe Tyr Pro Ser Asp Ile Ala Val Glu Trp Glu
305                 310                 315                 320
Ser Asn Gly Gln Pro Glu Asn Asn Tyr Lys Thr Thr Pro Pro Val Leu
                325                 330                 335
Asp Ser Asp Gly Ser Phe Phe Leu Val Ser Lys Leu Thr Val Asp Lys
            340                 345                 350
Ser Arg Trp Gln Gln Gly Asn Val Phe Ser Cys Ser Val Met His Glu
            355                 360                 365
Ala Leu His Asn His Tyr Thr Gln Lys Ser Leu Ser Leu Ser Pro Gly
            370                 375                 380
Lys
385

<210> SEQ ID NO 38
<211> LENGTH: 526
<212> TYPE: PRT
<213> ORGANISM: Artificial Sequence
```

<220> FEATURE:
<223> OTHER INFORMATION: Model repeat-motif-molecule H10-2-G3 with
       C-terminally conjugated model repeat-motif-molecule 9-26.

<400> SEQUENCE: 38

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Glu Tyr Gly Leu Thr Pro Leu Tyr Leu Ala Thr Ala His Gly His Leu
        35                  40                  45

Glu Ile Val Glu Val Leu Leu Lys Asn Gly Ala Asp Val Asn Ala Val
    50                  55                  60

Asp Ala Ile Gly Phe Thr Pro Leu His Leu Ala Ala Phe Ile Gly His
65                  70                  75                  80

Leu Glu Ile Ala Glu Val Leu Leu Lys His Gly Ala Asp Val Asn Ala
                85                  90                  95

Gln Asp Lys Phe Gly Lys Thr Ala Phe Asp Ile Ser Ile Gly Asn Gly
            100                 105                 110

Asn Glu Asp Leu Ala Glu Ile Leu Gln Pro Lys Ser Cys Asp Lys Thr
        115                 120                 125

His Thr Cys Pro Pro Cys Pro Ala Pro Glu Leu Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

Gly Gly Gly Gly Ser Gly Gly Gly Ser Gly Gly Gly Gly Ser Gly
        355                 360                 365

Gly Gly Gly Ser Asp Leu Gly Lys Lys Leu Leu Glu Ala Ala Arg Ala
    370                 375                 380

Gly Gln Asp Asp Glu Val Arg Ile Leu Met Ala Asn Gly Ala Asp Val

```
       385                 390                 395                 400
Asn Ala Lys Asp Phe Tyr Gly Ile Thr Pro Leu His Leu Ala Ala Ala
                    405                 410                 415

Tyr Gly His Leu Glu Ile Val Glu Val Leu Lys His Gly Ala Asp
                420                 425                 430

Val Asn Ala His Asp Trp Asn Gly Trp Thr Pro Leu His Leu Ala Ala
            435                 440                 445

Lys Tyr Gly His Leu Glu Ile Val Glu Val Leu Lys His Gly Ala
        450                 455                 460

Asp Val Asn Ala Ile Asp Asn Ala Gly Lys Thr Pro Leu His Leu Ala
465                 470                 475                 480

Ala Ala His Gly His Leu Glu Ile Val Glu Val Leu Lys Tyr Gly
                    485                 490                 495

Ala Asp Val Asn Ala Gln Asp Lys Phe Gly Lys Thr Ala Phe Asp Ile
                500                 505                 510

Ser Ile Asp Asn Gly Asn Glu Asp Leu Ala Glu Ile Leu Gln
            515                 520                 525

<210> SEQ ID NO 39
<211> LENGTH: 526
<212> TYPE: PRT
<213> ORGANISM: Artificial Sequence
<220> FEATURE:
<223> OTHER INFORMATION: Model repeat-motif-molecule H10-2-G3 with
      C-terminally conjugated IgG1 Fc-part with two disulfide bonds in
      the hinge region with C-terminally conjugated model repeat-motif-
      molecule 9-26

<400> SEQUENCE: 39

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
                20                  25                  30

Glu Tyr Gly Leu Thr Pro Leu Tyr Leu Ala Thr Ala His Gly His Leu
            35                  40                  45

Glu Ile Val Glu Val Leu Leu Lys Asn Gly Ala Asp Val Asn Ala Val
        50                  55                  60

Asp Ala Ile Gly Phe Thr Pro Leu His Leu Ala Ala Phe Ile Gly His
65                  70                  75                  80

Leu Glu Ile Ala Glu Val Leu Leu Lys His Gly Ala Asp Val Asn Ala
                85                  90                  95

Gln Asp Lys Phe Gly Lys Thr Ala Phe Asp Ile Ser Ile Gly Asn Gly
            100                 105                 110

Asn Glu Asp Leu Ala Glu Ile Leu Gln Pro Lys Ser Ser Asp Lys Thr
        115                 120                 125

His Thr Cys Pro Pro Cys Pro Ala Pro Glu Leu Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
```

```
            210                 215                 220
Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Val Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

Gly Gly Gly Gly Ser Gly Gly Gly Gly Ser Gly Gly Gly Gly Ser Gly
                355                 360                 365

Gly Gly Gly Ser Asp Leu Gly Lys Lys Leu Leu Glu Ala Ala Arg Ala
            370                 375                 380

Gly Gln Asp Asp Glu Val Arg Ile Leu Met Ala Asn Gly Ala Asp Val
385                 390                 395                 400

Asn Ala Lys Asp Phe Tyr Gly Ile Thr Pro Leu His Leu Ala Ala Ala
                405                 410                 415

Tyr Gly His Leu Glu Ile Val Glu Val Leu Leu Lys His Gly Ala Asp
            420                 425                 430

Val Asn Ala His Asp Trp Asn Gly Trp Thr Pro Leu His Leu Ala Ala
            435                 440                 445

Lys Tyr Gly His Leu Glu Ile Val Glu Val Leu Leu Lys His Gly Ala
            450                 455                 460

Asp Val Asn Ala Ile Asp Asn Ala Gly Lys Thr Pro Leu His Leu Ala
465                 470                 475                 480

Ala His Gly His Leu Glu Ile Val Glu Val Leu Leu Lys Tyr Gly
                485                 490                 495

Ala Asp Val Asn Ala Gln Asp Lys Phe Gly Lys Thr Ala Phe Asp Ile
            500                 505                 510

Ser Ile Asp Asn Gly Asn Glu Asp Leu Ala Glu Ile Leu Gln
            515                 520                 525

<210> SEQ ID NO 40
<211> LENGTH: 304
<212> TYPE: PRT
<213> ORGANISM: Artificial Sequence
<220> FEATURE:
<223> OTHER INFORMATION: Model repeat-motif-molecule H10-2-G3 with
      C-terminally conjugated model repeat-motif-molecule 9-26 with
      C-terminally conjugated hexa-histidine-tag.

<400> SEQUENCE: 40

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
                20                  25                  30

Glu Tyr Gly Leu Thr Pro Leu Tyr Leu Ala Thr Ala His Gly His Leu
            35                  40                  45
```

```
Glu Ile Val Glu Val Leu Leu Lys Asn Gly Ala Asp Val Asn Ala Val
 50                  55                  60

Asp Ala Ile Gly Phe Thr Pro Leu His Leu Ala Ala Phe Ile Gly His
 65                  70                  75                  80

Leu Glu Ile Ala Glu Val Leu Leu Lys His Gly Ala Asp Val Asn Ala
                 85                  90                  95

Gln Asp Lys Phe Gly Lys Thr Ala Phe Asp Ile Ser Ile Gly Asn Gly
                100                 105                 110

Asn Glu Asp Leu Ala Glu Ile Leu Gln Gly Gly Gly Ser Gly Gly
            115                 120                 125

Gly Gly Ser Gly Gly Gly Ser Gly Gly Gly Ser Asp Leu Gly
    130                 135                 140

Lys Lys Leu Leu Glu Ala Ala Arg Ala Gly Gln Asp Asp Glu Val Arg
145                 150                 155                 160

Ile Leu Met Ala Asn Gly Ala Asp Val Asn Ala Lys Asp Phe Tyr Gly
                165                 170                 175

Ile Thr Pro Leu His Leu Ala Ala Tyr Gly His Leu Glu Ile Val
                180                 185                 190

Glu Val Leu Leu Lys His Gly Ala Asp Val Asn Ala His Asp Trp Asn
            195                 200                 205

Gly Trp Thr Pro Leu His Leu Ala Ala Lys Tyr Gly His Leu Glu Ile
    210                 215                 220

Val Glu Val Leu Leu Lys His Gly Ala Asp Val Asn Ala Ile Asp Asn
225                 230                 235                 240

Ala Gly Lys Thr Pro Leu His Leu Ala Ala His Gly His Leu Glu
                245                 250                 255

Ile Val Glu Val Leu Leu Lys Tyr Gly Ala Asp Val Asn Ala Gln Asp
            260                 265                 270

Lys Phe Gly Lys Thr Ala Phe Asp Ile Ser Ile Asp Asn Gly Asn Glu
    275                 280                 285

Asp Leu Ala Glu Ile Leu Gln Gly Ser Gly His His His His His
290                 295                 300

<210> SEQ ID NO 41
<211> LENGTH: 304
<212> TYPE: PRT
<213> ORGANISM: Artificial Sequence
<220> FEATURE:
<223> OTHER INFORMATION: Model repeat-motif-molecule 9-26 with
      C-terminally conjugated model repeat-motif-molecule H10-2-G3 with
      C-terminally conjugated hexa-histidine-tag

<400> SEQUENCE: 41

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Lys Asp
             20                  25                  30

Phe Tyr Gly Ile Thr Pro Leu His Leu Ala Ala Tyr Gly His Leu
             35                  40                  45

Glu Ile Val Glu Val Leu Leu Lys His Gly Ala Asp Val Asn Ala His
 50                  55                  60

Asp Trp Asn Gly Trp Thr Pro Leu His Leu Ala Ala Lys Tyr Gly His
 65                  70                  75                  80

Leu Glu Ile Val Glu Val Leu Leu Lys His Gly Ala Asp Val Asn Ala
                 85                  90                  95
```

-continued

```
Ile Asp Asn Ala Gly Lys Thr Pro Leu His Leu Ala Ala Ala His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Gly Gly Gly Ser Gly
145                 150                 155                 160

Gly Gly Gly Ser Gly Gly Gly Ser Gly Gly Gly Ser Asp Leu
                165                 170                 175

Gly Lys Lys Leu Leu Glu Ala Ala Arg Ala Gly Gln Asp Asp Glu Val
            180                 185                 190

Arg Ile Leu Met Ala Asn Gly Ala Asp Val Asn Ala Lys Asp Glu Tyr
        195                 200                 205

Gly Leu Thr Pro Leu Tyr Leu Ala Thr Ala His Gly His Leu Glu Ile
    210                 215                 220

Val Glu Val Leu Leu Lys Asn Gly Ala Asp Val Asn Ala Val Asp Ala
225                 230                 235                 240

Ile Gly Phe Thr Pro Leu His Leu Ala Ala Phe Ile Gly His Leu Glu
                245                 250                 255

Ile Ala Glu Val Leu Leu Lys His Gly Ala Asp Val Asn Ala Gln Asp
            260                 265                 270

Lys Phe Gly Lys Thr Ala Phe Asp Ile Ser Ile Gly Asn Gly Asn Glu
        275                 280                 285

Asp Leu Ala Glu Ile Leu Gln Gly Ser Gly His His His His His His
    290                 295                 300
```

<210> SEQ ID NO 42
<211> LENGTH: 337
<212> TYPE: PRT
<213> ORGANISM: Artificial Sequence
<220> FEATURE:
<223> OTHER INFORMATION: Dimeric model repeat-motif-molecule 9-26 with
      C-terminally conjugated hexa-histidine-tag

<400> SEQUENCE: 42

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Phe Tyr Gly Ile Thr Pro Leu His Leu Ala Ala Ala Tyr Gly His Leu
        35                  40                  45

Glu Ile Val Glu Val Leu Leu Lys His Gly Ala Asp Val Asn Ala His
    50                  55                  60

Asp Trp Asn Gly Trp Thr Pro Leu His Leu Ala Lys Tyr Gly His
65                  70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala Ala His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Gly Gly Gly Ser Gly
145                 150                 155                 160
```

```
Gly Gly Gly Ser Gly Gly Gly Ser Gly Gly Gly Ser Asp Leu
            165             170             175
Gly Lys Lys Leu Leu Glu Ala Ala Ala Gly Gln Asp Asp Glu Val
        180             185             190
Arg Ile Leu Met Ala Asn Gly Ala Asp Val Asn Ala Lys Asp Phe Tyr
            195             200             205
Gly Ile Thr Pro Leu His Leu Ala Ala Ala Tyr Gly His Leu Glu Ile
210             215             220
Val Glu Val Leu Leu Lys His Gly Ala Asp Val Asn Ala His Asp Trp
225             230             235             240
Asn Gly Trp Thr Pro Leu His Leu Ala Ala Lys Tyr Gly His Leu Glu
            245             250             255
Ile Val Glu Val Leu Leu Lys His Gly Ala Asp Val Asn Ala Ile Asp
            260             265             270
Asn Ala Gly Lys Thr Pro Leu His Leu Ala Ala Ala His Gly His Leu
        275             280             285
Glu Ile Val Glu Val Leu Leu Lys Tyr Gly Ala Asp Val Asn Ala Gln
290             295             300
Asp Lys Phe Gly Lys Thr Ala Phe Asp Ile Ser Ile Asp Asn Gly Asn
305             310             315             320
Glu Asp Leu Ala Glu Ile Leu Gln Gly Ser Gly His His His His
            325             330             335
His

<210> SEQ ID NO 43
<211> LENGTH: 330
<212> TYPE: PRT
<213> ORGANISM: Homo sapiens

<400> SEQUENCE: 43

Ala Ser Thr Lys Gly Pro Ser Val Phe Pro Leu Ala Pro Ser Ser Lys
1               5               10              15
Ser Thr Ser Gly Gly Thr Ala Ala Leu Gly Cys Leu Val Lys Asp Tyr
            20              25              30
Phe Pro Glu Pro Val Thr Val Ser Trp Asn Ser Gly Ala Leu Thr Ser
        35              40              45
Gly Val His Thr Phe Pro Ala Val Leu Gln Ser Ser Gly Leu Tyr Ser
    50              55              60
Leu Ser Ser Val Val Thr Val Pro Ser Ser Leu Gly Thr Gln Thr
65              70              75              80
Tyr Ile Cys Asn Val Asn His Lys Pro Ser Asn Thr Lys Val Asp Lys
            85              90              95
Lys Val Glu Pro Lys Ser Cys Asp Lys Thr His Thr Cys Pro Pro Cys
        100             105             110
Pro Ala Pro Glu Leu Leu Gly Gly Pro Ser Val Phe Leu Phe Pro Pro
    115             120             125
Lys Pro Lys Asp Thr Leu Met Ile Ser Arg Thr Pro Glu Val Thr Cys
130             135             140
Val Val Val Asp Val Ser His Glu Asp Pro Glu Val Lys Phe Asn Trp
145             150             155             160
Tyr Val Asp Gly Val Glu Val His Asn Ala Lys Thr Lys Pro Arg Glu
            165             170             175
Glu Gln Tyr Asn Ser Thr Tyr Arg Val Val Ser Val Leu Thr Val Leu
        180             185             190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 327
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys

```
                225                 230                 235                 240
Asn Gln Val Ser Leu Thr Cys Leu Val Lys Gly Phe Tyr Pro Ser Asp
                    245                 250                 255

Ile Ala Val Glu Trp Glu Ser Asn Gly Gln Pro Glu Asn Asn Tyr Lys
                    260                 265                 270

Thr Thr Pro Pro Val Leu Asp Ser Asp Gly Ser Phe Phe Leu Tyr Ser
                    275                 280                 285

Arg Leu Thr Val Asp Lys Ser Arg Trp Gln Glu Gly Asn Val Phe Ser
                    290                 295                 300

Cys Ser Val Met His Glu Ala Leu His Asn His Tyr Thr Gln Lys Ser
305                 310                 315                 320

Leu Ser Leu Ser Leu Gly Lys
                    325

<210> SEQ ID NO 45
<211> LENGTH: 107
<212> TYPE: PRT
<213> ORGANISM: Homo sapiens

<400> SEQUENCE: 45

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 46
<211> LENGTH: 105
<212> TYPE: PRT
<213> ORGANISM: Human

<400> SEQUENCE: 46

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100                 105
```

```
<210> SEQ ID NO 47
<211> LENGTH: 28
<212> TYPE: PRT
<213> ORGANISM: Artificial Sequence
<220> FEATURE:
<223> OTHER INFORMATION: N-terminal capping repeat

<400> SEQUENCE: 47

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val
            20                  25

<210> SEQ ID NO 48
<211> LENGTH: 28
<212> TYPE: PRT
<213> ORGANISM: Artificial Sequence
<220> FEATURE:
<223> OTHER INFORMATION: C-terminal capping repeat

<400> SEQUENCE: 48

Val Asn Ala Gln Asp Lys Phe Gly Lys Thr Ala Phe Asp Ile Ser Ile
1               5                   10                  15

Asp Asn Gly Asn Glu Asp Leu Ala Glu Ile Leu Gln
            20                  25

<210> SEQ ID NO 49
<211> LENGTH: 602
<212> TYPE: DNA
<213> ORGANISM: Human cytomegalovirus

<400> SEQUENCE: 49
gttgacattg attattgact agttattaat agtaatcaat tacgggtca ttagttcata      60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattagc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa atgtcgtaa caactccgcc ccattgacgc    540
aaatgggcgg taggcgtgta cggtgggagg tctatataag cagagctccg tttagtgaac    600
gt                                                                   602

<210> SEQ ID NO 50
<211> LENGTH: 122
<212> TYPE: PRT
<213> ORGANISM: Artificial
<220> FEATURE:
<223> OTHER INFORMATION: VH

<400> SEQUENCE: 50

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Thr His Tyr Ala Arg Tyr Tyr Arg Tyr Phe Asp Val Trp
                100                 105                 110

Gly Gln Gly Thr Leu Val Thr Val Ser Ser
                115                 120
```

<210> SEQ ID NO 51
<211> LENGTH: 126
<212> TYPE: PRT
<213> ORGANISM: Artificial
<220> FEATURE:
<223> OTHER INFORMATION: VH

<400> SEQUENCE: 51

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Gly Asn Thr His Lys Pro Tyr Gly Tyr Val Arg Tyr
                100                 105                 110

Phe Asp Val Trp Gly Gln Gly Thr Leu Val Thr Val Ser Ser
                115                 120                 125
```

<210> SEQ ID NO 52
<211> LENGTH: 124
<212> TYPE: PRT
<213> ORGANISM: Artificial
<220> FEATURE:
<223> OTHER INFORMATION: VH

<400> SEQUENCE: 52

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Leu Ser Arg Gly Tyr Asn Gly Tyr Tyr His Lys Phe Asp
```

```
                100             105             110
Val Trp Gly Gln Gly Thr Leu Val Thr Val Ser Ser
            115                 120
```

<210> SEQ ID NO 53
<211> LENGTH: 110
<212> TYPE: PRT
<213> ORGANISM: Artificial
<220> FEATURE:
<223> OTHER INFORMATION: VL

<400> SEQUENCE: 53

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Val Tyr Asn Pro Pro
                85                  90                  95

Val Thr Phe Gly Gln Gly Thr Lys Val Glu Ile Lys Arg Thr
            100                 105                 110
```

<210> SEQ ID NO 54
<211> LENGTH: 110
<212> TYPE: PRT
<213> ORGANISM: Artificial
<220> FEATURE:
<223> OTHER INFORMATION: VL

<400> SEQUENCE: 54

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Phe Gln Leu Tyr Ser Asp Pro
                85                  90                  95

Phe Thr Phe Gly Gln Gly Thr Lys Val Glu Ile Lys Arg Thr
            100                 105                 110
```

<210> SEQ ID NO 55
<211> LENGTH: 110
<212> TYPE: PRT
<213> ORGANISM: Artificial
<220> FEATURE:
<223> OTHER INFORMATION: VL

<400> SEQUENCE: 55

```
Asp Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Leu Ser Ser Phe Pro
                85                  90                  95

Pro Thr Phe Gly Gln Gly Thr Lys Val Glu Ile Lys Arg Thr
            100                 105                 110

<210> SEQ ID NO 56
<211> LENGTH: 130
<212> TYPE: PRT
<213> ORGANISM: Artificial Sequence
<220> FEATURE:
<223> OTHER INFORMATION: Model repeat-motif-molecule H10-2-G3 with
      C-terminally conjugated hexa-histidine-tag amino acid sequence and
      introduced engineered glycosylation site at the beginning of the
      C-capping repeat.

<400> SEQUENCE: 56

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Lys Asp
            20                  25                  30

Glu Tyr Gly Leu Thr Pro Leu Tyr Leu Ala Thr Ala His Gly His Leu
        35                  40                  45

Glu Ile Val Glu Val Leu Leu Lys Asn Gly Ala Asp Val Asn Ala Val
 50                  55                  60

Asp Ala Ile Gly Phe Thr Pro Leu His Leu Ala Ala Phe Ile Gly His
 65                  70                  75                  80

Leu Glu Ile Ala Glu Val Leu Leu Lys His Gly Ala Asp Val Asn Ala
                85                  90                  95

Thr Asp Lys Phe Gly Lys Thr Ala Phe Asp Ile Ser Ile Gly Asn Gly
            100                 105                 110

Asn Glu Asp Leu Ala Glu Ile Leu Gln Gly Ser Gly His His His His
        115                 120                 125

His His
    130

<210> SEQ ID NO 57
<211> LENGTH: 421
<212> TYPE: PRT
<213> ORGANISM: Artificial Sequence
<220> FEATURE:
<223> OTHER INFORMATION: Model repeat-motif-molecule H10-2-G3 with
      C-terminally conjugated IgG1 Fc-part and thereto C-terminally
      conjugated membrane anchor domain.

<400> SEQUENCE: 57

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Lys Asp
            20                  25                  30

Glu Tyr Gly Leu Thr Pro Leu Tyr Leu Ala Thr Ala His Gly His Leu
        35                  40                  45
```

```
Glu Ile Val Glu Val Leu Leu Lys Asn Gly Ala Asp Val Asn Ala Val
         50                  55                  60

Asp Ala Ile Gly Phe Thr Pro Leu His Leu Ala Ala Phe Ile Gly His
 65                  70                  75                  80

Leu Glu Ile Ala Glu Val Leu Leu Lys His Gly Ala Asp Val Asn Ala
                 85                  90                  95

Gln Asp Lys Phe Gly Lys Thr Ala Phe Asp Ile Ser Ile Gly Asn Gly
                100                 105                 110

Asn Glu Asp Leu Ala Glu Ile Leu Gln Pro Lys Ser Cys Asp Lys Thr
            115                 120                 125

His Thr Cys Pro Pro Cys Pro Ala Pro Glu Leu Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
275                 280                 285

Asn Gly Gln Pro Glu Asn Asn Tyr Lys Thr Thr Pro Pro Val Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Glu Leu
            340                 345                 350

Gln Leu Glu Glu Ser Cys Ala Glu Ala Gln Asp Gly Glu Leu Asp Gly
355                 360                 365

Leu Trp Thr Thr Ile Thr Ile Phe Ile Thr Leu Phe Leu Leu Ser Val
370                 375                 380

Cys Tyr Ser Ala Thr Val Thr Phe Phe Lys Val Lys Trp Ile Phe Ser
385                 390                 395                 400

Ser Val Val Asp Leu Lys Gln Thr Ile Val Pro Asp Tyr Arg Asn Met
                405                 410                 415

Ile Arg Gln Gly Ala
            420

<210> SEQ ID NO 58
<211> LENGTH: 163
<212> TYPE: PRT
<213> ORGANISM: Artificial Sequence
<220> FEATURE:
```

<223> OTHER INFORMATION: Model repeat-motif-molecule 9-26 with
      C-terminally conjugated hexa-histidine-tag amino acid sequence and
      introduced engineered glycosylation site at the beginning of the
      C-capping repeat.

<400> SEQUENCE: 58

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Phe Tyr Gly Ile Thr Pro Leu His Leu Ala Ala Ala Tyr Gly His Leu
        35                  40                  45

Glu Ile Val Glu Val Leu Leu Lys His Gly Ala Asp Val Asn Ala His
    50                  55                  60

Asp Trp Asn Gly Trp Thr Pro Leu His Leu Ala Ala Lys Tyr Gly His
65                  70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala Ala His Gly
            100                 105                 110

His Leu Glu Ile Val Glu Val Leu Leu Lys Tyr Gly Ala Asp Val Asn
        115                 120                 125

Ala Thr Asp Lys Phe Gly Lys Thr Ala Phe Asp Ile Ser Ile Asp Asn
    130                 135                 140

Gly Asn Glu Asp Leu Ala Glu Ile Leu Gln Gly Ser Gly His His His
145                 150                 155                 160

His His His

<210> SEQ ID NO 59
<211> LENGTH: 454
<212> TYPE: PRT
<213> ORGANISM: Artificial Sequence
<220> FEATURE:
<223> OTHER INFORMATION: Model repeat-motif-molecule 9-26 with
      C-terminally conjugated IgG1 Fc-part and thereto C-terminally
      conjugated membrane anchor domain.

<400> SEQUENCE: 59

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Phe Tyr Gly Ile Thr Pro Leu His Leu Ala Ala Ala Tyr Gly His Leu
        35                  40                  45

Glu Ile Val Glu Val Leu Leu Lys His Gly Ala Asp Val Asn Ala His
    50                  55                  60

Asp Trp Asn Gly Trp Thr Pro Leu His Leu Ala Ala Lys Tyr Gly His
65                  70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala Ala His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Pro Lys Ser Cys Asp Lys

```
                145                 150                 155                 160
        Thr His Thr Cys Pro Pro Cys Pro Ala Pro Glu Leu Leu Gly Gly Pro
                    165                 170                 175

Ser Val Phe Leu Phe Pro Pro Lys Pro Lys Asp Thr Leu Met Ile Ser
                    180                 185                 190

Arg Thr Pro Glu Val Thr Cys Val Val Val Asp Val Ser His Glu Asp
                    195                 200                 205

Pro Glu Val Lys Phe Asn Trp Tyr Val Asp Gly Val Glu Val His Asn
                    210                 215                 220

Ala Lys Thr Lys Pro Arg Glu Glu Gln Tyr Asn Ser Thr Tyr Arg Val
        225                 230                 235                 240

Val Ser Val Leu Thr Val Leu His Gln Asp Trp Leu Asn Gly Lys Glu
                    245                 250                 255

Tyr Lys Cys Lys Val Ser Asn Lys Ala Leu Pro Ala Pro Ile Glu Lys
                    260                 265                 270

Thr Ile Ser Lys Ala Lys Gly Gln Pro Arg Glu Pro Gln Val Tyr Thr
                    275                 280                 285

Leu Pro Pro Ser Arg Asp Glu Leu Thr Lys Asn Gln Val Ser Leu Thr
                    290                 295                 300

Cys Leu Val Lys Gly Phe Tyr Pro Ser Asp Ile Ala Val Glu Trp Glu
        305                 310                 315                 320

Ser Asn Gly Gln Pro Glu Asn Asn Tyr Lys Thr Thr Pro Pro Val Leu
                    325                 330                 335

Asp Ser Asp Gly Ser Phe Phe Leu Tyr Ser Lys Leu Thr Val Asp Lys
                    340                 345                 350

Ser Arg Trp Gln Gln Gly Asn Val Phe Ser Cys Ser Val Met His Glu
                    355                 360                 365

Ala Leu His Asn His Tyr Thr Gln Lys Ser Leu Ser Leu Ser Pro Glu
                    370                 375                 380

Leu Gln Leu Glu Glu Ser Cys Ala Glu Ala Gln Asp Gly Glu Leu Asp
        385                 390                 395                 400

Gly Leu Trp Thr Thr Ile Thr Ile Phe Ile Thr Leu Phe Leu Leu Ser
                    405                 410                 415

Val Cys Tyr Ser Ala Thr Val Thr Phe Phe Lys Val Lys Trp Ile Phe
                    420                 425                 430

Ser Ser Val Val Asp Leu Lys Gln Thr Ile Val Pro Asp Tyr Arg Asn
                    435                 440                 445

Met Ile Arg Gln Gly Ala
            450

<210> SEQ ID NO 60
<211> LENGTH: 149
<212> TYPE: PRT
<213> ORGANISM: Artificial Sequence
<220> FEATURE:
<223> OTHER INFORMATION: Model repeat-motif-molecule H10-2-G3 with
      C-terminally conjugated hexa-histidine-tag amino acid sequence and
      glycosylation tag in the C-terminal region.

<400> SEQUENCE: 60

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
                20                  25                  30

Glu Tyr Gly Leu Thr Pro Leu Tyr Leu Ala Thr Ala His Gly His Leu
            35                  40                  45
```

```
Glu Ile Val Glu Val Leu Leu Lys Asn Gly Ala Asp Val Asn Ala Val
            50                  55                  60
Asp Ala Ile Gly Phe Thr Pro Leu His Leu Ala Ala Phe Ile Gly His
 65                  70                  75                  80
Leu Glu Ile Ala Glu Val Leu Leu Lys His Gly Ala Asp Val Asn Ala
                    85                  90                  95
Gln Asp Lys Phe Gly Lys Thr Ala Phe Asp Ile Ser Ile Gly Asn Gly
                100                 105                 110
Asn Glu Asp Leu Ala Glu Ile Leu Gln Gly Ser Gly Asn Gly Thr Glu
            115                 120                 125
Gly Pro Asn Phe Tyr Val Pro Phe Ser Asn Lys Thr Gly Ser Gly His
            130                 135                 140
His His His His His
145
```

<210> SEQ ID NO 61
<211> LENGTH: 182
<212> TYPE: PRT
<213> ORGANISM: Artificial Sequence
<220> FEATURE:
<223> OTHER INFORMATION: Model repeat-motif-molecule 9-26 with
      C-terminally conjugated hexa-histidine-tag amino acid sequence and
      glycosylation tag in the C-terminal region.

<400> SEQUENCE: 61

```
Asp Leu Gly Lys Lys Leu Leu Glu Ala Ala Arg Ala Gly Gln Asp Asp
 1               5                  10                  15
Glu Val Arg Ile Leu Met Ala Asn Gly Ala Asp Val Asn Ala Lys Asp
                20                  25                  30
Phe Tyr Gly Ile Thr Pro Leu His Leu Ala Ala Ala Tyr Gly His Leu
                35                  40                  45
Glu Ile Val Glu Val Leu Leu Lys His Gly Ala Asp Val Asn Ala His
            50                  55                  60
Asp Trp Asn Gly Trp Thr Pro Leu His Leu Ala Ala Lys Tyr Gly His
 65                  70                  75                  80
Leu Glu Ile Val Glu Val Leu Leu Lys His Gly Ala Asp Val Asn Ala
                    85                  90                  95
Ile Asp Asn Ala Gly Lys Thr Pro Leu His Leu Ala Ala Ala His Gly
                100                 105                 110
His Leu Glu Ile Val Glu Val Leu Leu Lys Tyr Gly Ala Asp Val Asn
            115                 120                 125
Ala Gln Asp Lys Phe Gly Lys Thr Ala Phe Asp Ile Ser Ile Asp Asn
            130                 135                 140
Gly Asn Glu Asp Leu Ala Glu Ile Leu Gln Gly Ser Gly Asn Gly Thr
145                 150                 155                 160
Glu Gly Pro Asn Phe Tyr Val Pro Phe Ser Asn Lys Thr Gly Ser Gly
                165                 170                 175
His His His His His His
            180
```

<210> SEQ ID NO 62
<211> LENGTH: 149
<212> TYPE: PRT
<213> ORGANISM: Artificial Sequence
<220> FEATURE:
<223> OTHER INFORMATION: Model repeat-motif-molecule H10-2-G3 with
      C-terminally conjugated hexa-histidine-tag amino acid sequence and
      glycosylation tag in the C-terminal region.

```
<400> SEQUENCE: 62

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Glu Tyr Gly Leu Thr Pro Leu Tyr Leu Ala Thr Ala His Gly His Leu
        35                  40                  45

Glu Ile Val Glu Val Leu Leu Lys Asn Gly Ala Asp Val Asn Ala Val
    50                  55                  60

Asp Ala Ile Gly Phe Thr Pro Leu His Leu Ala Ala Phe Ile Gly His
65                  70                  75                  80

Leu Glu Ile Ala Glu Val Leu Leu Lys His Gly Ala Asp Val Asn Ala
                85                  90                  95

Gln Asp Lys Phe Gly Lys Thr Ala Phe Asp Ile Ser Ile Gly Asn Gly
            100                 105                 110

Asn Glu Asp Leu Ala Glu Ile Leu Gln Gly Ser Gly Asn Gly Thr Glu
        115                 120                 125

Gly Pro Asn Phe Tyr Val Pro Phe Ser Asn Ala Thr Gly Ser Gly His
    130                 135                 140

His His His His His
145

<210> SEQ ID NO 63
<211> LENGTH: 182
<212> TYPE: PRT
<213> ORGANISM: Artificial Sequence
<220> FEATURE:
<223> OTHER INFORMATION: Model repeat-motif-molecule 9-26 with
      C-terminally conjugated hexa-histidine-tag amino acid sequence and
      glycosylation tag in the C-terminal region.

<400> SEQUENCE: 63

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Phe Tyr Gly Ile Thr Pro Leu His Leu Ala Ala Ala Tyr Gly His Leu
        35                  40                  45

Glu Ile Val Glu Val Leu Leu Lys His Gly Ala Asp Val Asn Ala His
    50                  55                  60

Asp Trp Asn Gly Trp Thr Pro Leu His Leu Ala Ala Lys Tyr Gly His
65                  70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala Ala His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Gly Ser Gly Asn Gly Thr
145                 150                 155                 160

Glu Gly Pro Asn Phe Tyr Val Pro Phe Ser Asn Ala Thr Gly Ser Gly
                165                 170                 175

His His His His His His
            180
```

```
<210> SEQ ID NO 64
<211> LENGTH: 163
<212> TYPE: PRT
<213> ORGANISM: Artificial Sequence
<220> FEATURE:
<223> OTHER INFORMATION: anticalin A-44 with hexa-his-tag

<400> SEQUENCE: 64
```

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
            20                  25                  30

Ile Pro Thr Thr Leu Thr Thr Leu Glu Gly Gly Asn Leu Glu Ala Lys
        35                  40                  45

Val Thr Met His Ile Lys Gly Arg Ser Gln Glu Val Lys Ala Val Leu
    50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala Gly Ser Gly His His His
145                 150                 155                 160

His His His

```
<210> SEQ ID NO 65
<211> LENGTH: 385
<212> TYPE: PRT
<213> ORGANISM: Artificial Sequence
<220> FEATURE:
<223> OTHER INFORMATION: anticalin A-44 with Fc-tag (3 SS bridges)

<400> SEQUENCE: 65
```

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
            20                  25                  30

Ile Pro Thr Thr Leu Thr Thr Leu Glu Gly Gly Asn Leu Glu Ala Lys
        35                  40                  45

Val Thr Met His Ile Lys Gly Arg Ser Gln Glu Val Lys Ala Val Leu
    50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

```
Gln Ser Glu Thr Ser Ser Pro Gly Ser Ala Pro Lys Ser Cys Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 66
<211> LENGTH: 385
<212> TYPE: PRT
<213> ORGANISM: Artificial Sequence
<220> FEATURE:
<223> OTHER INFORMATION: anticalin A-44 with Fc-tag (3 SS bridges)

<400> SEQUENCE: 66

Ala Ser Asp Glu Glu Ile Gln Asp Val Ser Gly Thr Trp Tyr Leu Lys
1               5                   10                  15

Ala Met Thr Val Asp Val Gly Ala Leu Arg Cys Leu Ala Gly Ser Val
            20                  25                  30

Ile Pro Thr Thr Leu Thr Thr Leu Glu Gly Gly Asn Leu Glu Ala Lys
        35                  40                  45

Val Thr Met His Ile Lys Gly Arg Ser Gln Glu Val Lys Ala Val Leu
    50                  55                  60

Ser Lys Thr Asp Glu Pro Gly Ile Tyr Thr Ala Ile Gly Gly Ile His
65                  70                  75                  80

Val Ala Lys Ile Gly Arg Ser His Val Lys Asp His Tyr Ile Phe Tyr
                85                  90                  95

Ser Glu Gly Cys Leu Ser Gly Val Pro Val Pro Gly Val Trp Leu Val
            100                 105                 110
```

-continued

```
Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
130                 135                 140

Gln Ser Glu Thr Ser Ser Pro Gly Ser Ala Pro Lys Ser Ser Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385
```

GLYCOSYLATED REPEAT-MOTIF-MOLECULE CONJUGATES

This application is a continuation of International Patent Application No. PCT/EP2010/006728, filed Nov. 4, 2010, which claims the benefit of and priority to European Application No. 09013887.6, filed Nov. 5, 2009.

Herein are reported GEMOCs (glycosylated repeat-motif-molecule conjugates), which are produced recombinantly and comprise an in vivo glycosylation, i.e. from the cell type expressing the EMOC (repeat-motif-molecule conjugate), as well as a method for producing these conjugates and the use of these conjugates.

BACKGROUND OF THE INVENTION

Different repeat-motif-molecules have been developed to provide an alternative to classical antigen binding molecules, such as immunoglobulins.

Exemplary repeat-motif-molecules are designed ankyrin repeat proteins (DARPins). DARPins can be expressed in functional form in the cytoplasm of *E.coli* strains. The repeat motif of DARPins comprises a 33-residue amino acid sequence. The repeats comprise a β-turn motif followed by a pair of antiparallel α-helices and a loop leading to the turn of the next repeat. Generally between 1 to more than 30 repeat motifs are present in ankyrin repeat-motif-molecules, whereby 4 to 6 are most frequent.

Kohl et al. (Kohl, A., et al., Proc. Natl. Acad. Sci. USA 100 (2003) 1700-1705) developed an artificial ankyrin repeat module based on the alignment of about 2000 naturally occurring ankyrin repeat sequences. This artificial consensus ankyrin repeat sequence comprises 27 fixed amino acid residues and 6 variable amino acid residues forming a (part of a) binding site (Forrer, P., et al., ChemBioChem 5 (2004) 183-189).

In order to obtain DARPins binding to a predetermined target molecule the variable amino acid residues of the artificial consensus ankyrin repeat sequence are randomized and a specific binder is identified via ribosome display (see e.g. WO 02/020565; Hanes, Proc. Natl. Acad. Sci. USA 94 (1997) 4937-4942).

In US 2009/0148905 antigen binding constructs are reported. Complement factor H-derived short consensus repeat-antibody constructs are reported in WO 2008/135237. Antibody-RNAse-conjugates are reported in WO 2007/122511. A Newcastle Disease Virus comprising a recombinant nucleic acid, wherein the nucleic acid codes for a binding protein that has a therapeutic activity when expressed by the virus-infected tumor cell is reported in US 2008/0206201. In US 2008/0248026 PTEN/AKT methods and compositions relating to BMP are reported. Recombinant expression of proteins in a disulfide-bridged, two-chain form is reported in WO2005/076902 and US 2008/0103098. In WO 2009/068649 antigen-binding constructs are reported.

SUMMARY OF THE INVENTION

Herein are reported repeat-motif-molecule conjugates in glycosylated form, i.e. expressed in mammalian cells.

Therefore, a first aspect as reported herein is a glycosylated repeat-motif-molecule conjugate of the following formula (repeat-motif-molecule–linker$_n$)$_m$–(conjugation partner)$_q$–(linker$_o$–repeat-motif-molecule)$_p$ wherein n and o are independently of each other and independently for each value of m and p and q integer values of 0 or 1, and m and p are independently of each other integer values of 0 or 1 or 2 or 3 or 4 or 5 or 6 or 7, and q is independently of the values of n, m, o, and p an integer value of 0 or 1, and wherein the repeat-motif-molecule conjugate comprises at least one oligosaccharide attached to a glycosylation site, and wherein at least m=q=1 or p=q=1.

In one embodiment the repeat-motif-molecule is an ankyrin-repeat-motif-molecule or a leucine-rich-repeat-motif-molecule. In a further embodiment the ankyrin-repeat-motif-molecule has an amino acid sequence of SEQ ID NO: 4 or a variant thereof. In another embodiment the linker is a peptidic linker selected from SEQ ID NO: 14 and SEQ ID NO: 25 to SEQ ID NO: 33. In one embodiment the conjugation partner is a multimerizing conjugation partner. In still a further embodiment the multimerizing conjugation partner is selected from natural or engineered pairs of heavy chain CH2 and CH3 domains, from natural or engineered pairs of heavy chain CH1 domain and light chain constant domain, from natural or engineered heavy chain hinge region, from natural or engineered sequences of heavy chain hinge region and CH2 and CH3 domains, from leucine zipper domain, from isoleucine zipper domain, from 4-helix-bundles, and from p53 tetramerization domain, or from combinations thereof.

In one embodiment the conjugate according to the invention is characterized in that it has the formula of ((repeat-motif-molecule–linker$_n$)$_m$–(conjugation partner)$_q$–(linker$_o$–repeat-motif-molecule)$_p$)$_r$ with
i) n=1, m=1, q=1, p=0, r=1, or
ii) n=1, m=1, q=1, p=0, r=2, or
iii) n=0, m=1, q=1, p=0, r=1, or
iv) n=0, m=1, q=1, p=0, r=2, or
v) m=0, o=1, q=1, p=1, r=1, or
vi) m=0, o=1, q=1, p=1, r=2, or
vii) m=0, o=0, q=1, p=1, r=1, or
viii) m=0, o=0, q=1, p=1, r=2, or
ix) m=1, n=0, o=1, q=1, p=1, r=1, or
x) m=1, n=0, o=1, q=1, p=1, r=2, or
xi) m=1, n=1, o=1, q=1, p=1, r=1, or
xii) m=1, n=1, o=1, q=1, p=1, r=1, wherein the conjugation partner is selected from natural or engineered pairs of heavy chain CH2 and CH3 domains, natural or engineered pairs of heavy chain CH1 domain and light chain constant domain, natural or engineered heavy chain hinge regions, natural or engineered sequences of heavy chain hinge region and CH2 and CH3 domains, and wherein the repeat-motif-molecule is an ankyrin-repeat-motif-molecule.

In a further embodiment the conjugate is characterized in that the at least one oligosaccharide is a mixture of oligosaccharides obtained by the expression of the conjugate in CHO cells or HEK293 cells.

In one embodiment the conjugate is characterized in that m=0, q=1, p=1, and o=0 or o=1, and r=1 or 2, wherein the conjugation partner is selected from a conjugate of N-terminal SEQ ID NO: 50 or 51 or 52 and C-terminal of SEQ ID NO: 43 or 44, or of N-terminal of SEQ ID NO: 53 or 54 or 55, and C-terminal of SEQ ID NO: 45 or 46, and wherein the repeat-motif-molecule is an ankyrin-repeat-motif-molecule.

Another aspect as reported herein is a glycosylated repeat-motif-molecule conjugate, characterized in comprising two glycosylated repeat-motif-molecule conjugates as reported herein.

In another embodiment the glycosylated repeat-motif-molecule conjugate comprises two glycosylated repeat-motif-molecule conjugates according to one of the previous embodiments.

In a further embodiment the glycosylated repeat-motif-molecule conjugate further comprises
a) in case the conjugation partner of the repeat-motif-molecule is selected from SEQ ID NO: 50, 51 and 52 two conjugates of N-terminal of SEQ ID NO: 53 or 54 or 55 and C-terminal of SEQ ID NO: 45 or 46, or
b) in case the conjugation partner of the repeat-motif-molecule is selected from SEQ ID NO: 53, 54 and 55 two conjugates of N-terminal of SEQ ID NO: 50 or 51 or 52 and C-terminal of SEQ ID NO: 43 or 44.

A further aspect as reported herein is a nucleic acid comprising the following elements:
the immediate early enhancer and promoter from the human cytomegalovirus,
a 5'-untranslated region of an antibody germline gene,
an immunoglobulin heavy chain signal sequence,
a repeat-motif-molecule conjugate's encoding sequence,
a polyadenylation ("poly A") signal sequence.

Another aspect as reported herein is a method for producing a glycosylated repeat-motif-molecule conjugate as reported herein comprising
cultivating a mammalian cell comprising a nucleic acid as reported herein under conditions suitable for the expression of the repeat-motif-molecule,
recovering the glycosylated repeat-motif-molecule from the cell or the cultivation medium and thereby producing the glycosylated repeat-motif-molecule,
optionally purifying the recovered glycosylated repeat-motif-molecule.

In one embodiment the mammalian cell is selected from CHO cells and HEK293 cells.

In one embodiment the multimerizing conjugation partner is an engineered heavy chain hinge region with three cysteine residues. In another embodiment the conjugation partner comprises the engineered antibody heavy chain hinge region, a CH2 domain and a CH3 domain. In a further embodiment the repeat-motif-molecule is an anticalin. In still another embodiment the repeat-motif-molecule is conjugated to the N-terminus of the conjugation partner.

DETAILED DESCRIPTION OF THE INVENTION

Herein are reported glycosylated repeat-motif-molecule conjugates (GEMOCs) of the general formula:

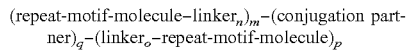

(repeat-motif-molecule–linker$_n$)$_m$–(conjugation partner)$_q$–(linker$_o$–repeat-motif-molecule)$_p$ wherein n and o are independently of each other and independently for each value of m and p integer values of 0 or 1, and m and p are independently of each other integer values of 0 or 1 or 2 or 3 or 4 or 5 or 6 or 7, q is independently 0 or 1,
wherein the conjugation partner comprises at least one glycosylation site and the GEMOC is expressed in a mammalian cell.

The term "glycosylated" or grammatical equivalents thereof denotes that the respective repeat-motif-molecule comprise a saccharide residue covalently linked to an amino acid of the amino acid backbone of the repeat-motif-molecule. In one embodiment the repeat-motif-molecule comprises at least one N- or O-glycosylation site motif, either a natural occurring or engineered motif (see SEQ ID NO: 56 and 58). In one embodiment the N-glycosylation site motif is selected from asp-X-thr, asp-X-ser, or asp-X-cys, wherein X can be any amino acid residues but not proline (pro, P). In another embodiment a glycosylation tag is added to the repeat-motif-molecule (see e.g. SEQ ID NO: 60, 61, 62, and 63; see also Meder, D., et al., J. Cell Biol. 168 (2005) 303-313; Bulbarelli, A., et al., J. Cell Sci., 115 (2002) 1689-1702). Thus, in one embodiment the conjugate comprises as repeat-motif-molecule a molecule of SEQ ID NO: 62 or 63. With these glycosylation tag comprising repeat-motif-molecules a good glycosylation can be achieved.

The term "mammalian cell" denotes a cell selected from CHO cells, BHK cells, HEK cells, COS cells, Per.C6® cells, or hybridoma cells.

The term "amino acid" as used within this application denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy a-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "antibody" refers to a molecule consisting of one or more polypeptide(s) substantially encoded by antibody genes. An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an antibody's light or heavy chain in turn comprises different segments, i.e. four framework regions (FR) and three hypervariable regions (CDR).

The term "hinge region" denotes the fragment of a, in one embodiment human, full length antibody heavy chain of from residue 216, which is normally a glutamic acid residue, to residue 226, which is normally a cysteine residue, or to residue 230, which is normally a proline residue. The hinge region comprises cysteine residues which can form disulfide bonds with the corresponding cysteine residues of a second hinge region, e.g. of a second antibody heavy chain. In one embodiment the hinge region comprises two cysteine residues.

The terms "second heavy chain constant domain" and "CH2 domain" and "CH2" which can be used interchangeably denote the fragment of a, in one embodiment human, full length antibody heavy chain of from residue 231 to residue 340. The CH2 domain comprises residue 297, which is normally the amino acid asparagine, at which a saccharide is covalently attached to the amino acid backbone.

The terms "third heavy chain constant domain" and "CH3 domain" and "CH3" which can be used interchangeably denote the fragment of a, in one embodiment human, full length antibody heavy chain of from residue 341 to residue 447, i.e. C-terminal to the CH2 domain.

The terms "antibody-dependent cell-mediated cytotoxicity" and "ADCC" which can be used interchangeably within this application denote a mechanism of cell lysis effected by nonspecific cytotoxic cells having an Fc-Receptor (FcR) on its cell surface, such as natural killer cells (NK cells), neutrophils and macrophages. These cells recognize and lyse cells with surface bound antibody having an Fc-Receptor binding portion, such as an Fc-part.

The terms "complement dependent cytotoxicity" and "CDC" which can be used interchangeably within this application denote a mechanism of cell lysis effected by complement, which is initiated by binding of Clq to e.g. an antibody bound to its antigen.

The term "binding to a target molecule" denotes a specific interaction between a binding, i.e. complementarity providing, molecule and its binding partner, i.e. a specific target molecule. The strength of this specific interaction denoted as binding affinity is given as $K_D$-value. The term "not specifically binding to a target molecule" denotes a non-specific interaction between a binding molecule and its target molecules with a $K_D$-value of $10^{-5}$ mol/l or higher (e.g. $10^{-3}$ mol/l), in one embodiment with a $K_D$-value of $10^{-6}$ mol/l or higher. The binding affinity is determined with a standard binding assay, such as surface plasmon resonance technique (BIAcore®). This binding affinity value has not to be treated as an exact value, it is merely a point of reference. The term "specifically binding to a target molecule" denotes a specific interaction between a binding molecule and its target molecule with a $K_D$-value of $10^{-7}$ mol/l or lower (e.g. $10^{-10}$ mol/l), in one embodiment with a $K_D$-value of $10^{-8}$ mol/l or lower.

In one embodiment the repeats of the repeat-motif-molecule are of from 20 to 40 amino acid residues in length. The repeats are arranged in individual structural units forming together the repeat-motif-molecule. In one embodiment the repeat-motif-molecule is selected from ankyrin-repeat-motif-molecule and leucine-rich-repeat-motif-molecule (LR-RPs).

In one embodiment the conjugation partner comprises an immunoglobulin membrane anchor domain or a GPI-anchor domain.

The term "repeat-motif-molecule" denotes a natural occurring or artificial polypeptide that can be expressed as single molecule, i.e. not conjugated to a second molecule or to a second copy of itself, in soluble form in the cytoplasm or periplasm of E. coli. In one embodiment the repeat-motif-molecule comprises at least two structurally identical units (repeats). These units do not need to be identical in their amino acid sequence. These units can but do not need to be independently folding domains. The repeat-motif-molecule can but does not have to comprise other sequence stretches in addition to the repetitive units. In one embodiment the repeat-motif-molecule is an ankyrin-repeat-motif-molecule. In another embodiment the repeat-motif-molecule is a leucine-rich-repeat-motif-molecule.

The term "ankyrin-repeat-motif-molecule" denotes an artificial polypeptide comprising of from 1 to 30 consensus 33-residue amino acid sequences. Each of the repeats comprises a β-turn motif followed by a pair of antiparallel α-helices and a loop leading to the turn of the next repeat. In one embodiment the ankyrin-repeat-motif-molecule comprises of from 1 to 30 repeats, in another embodiment of from 2 to 10 repeat, and in a further embodiment of from 3 to 6 repeats.

In one embodiment the ankyrin-repeat-motif-molecule is derived from one of the following consensus sequences by random mutagenesis and selection for target molecule binding, e.g. by ribosome display, yeast display or phage display:

```
                                          (SEQ ID NO: 01)
DGNT(P,A)LHLA(A,V) ENG(H,N)LE(I,V)VKL L(L,I)
EAGA(D,N)INA, (SEQ ID NO: 02)
DSDGNTPLHL AAENGQLEVV KLLLEAGADV NAR, (SEQ ID NO: 03)
(D,T)KNGLTPLH(L,I) AAQEGHLEVV KLLLENGA(D,N)
(V,I) NAK, (SEQ ID NO: 04)
DxxGxTPLHL AAxxGHLEIV EVLLK(H,N,Y)GADV NAx, (SEQ ID NO: 05)
ADVNAKDKDG YTPLHLAARE GHLEIVEVLL KAG, (SEQ ID NO: 06)
DxxGxTPLHLAaxxGpxpaVpxLLpxGADVNAx, (SEQ ID NO: 07)
DxxGxTPLHLAxxxGxxxVVxLLLxxGADVNAx, (SEQ ID NO: 08)
DxxGxTPLHLAxxxGxxxIVxVLLxxGADVNAx, (SEQ ID NO: 09)
D11G1TPLHLAA11GHLEIVEVLLK2GADVNA1,
``` with "x" denoting a fully variable position, with the amino acids given in brackets denoting the specific variants possible at this position, with "a" denoting an amino acid with an apolar side chain, with "p" denoting an amino acid residue with a polar side chain, with "1" denoting an amino acid residue selected from the group consisting of (in one letter code) amino acid residues A, D, E, F, H, I, K, L, M, N, Q, R, S, T, V, W and Y, and with "2" denoting an amino acid residue selected from the group consisting of the amino acid residues H, N and Y.

GEMOCs comprising ankyrin-repeat-motif-molecules binding to any predetermined target molecule can be obtained by screening libraries comprising randomized GEMOCs or randomized ankyrin-repeat-motif-molecules e.g. by ribosome display (see e.g. WO 02/120565; Hanes, J. and Plückthun, A., Proc. Natl. Acad. Sci. USA 94 (1997) 4937-4942).

In one embodiment the GEMOC comprises an N-terminal capping repeat of the amino acid sequence of DLGKKLLE AARAGQDDEVRILMANGADV (SEQ ID NO: 47).

In one embodiment the GEMOC comprises a C-terminal capping repeat of the amino acid sequence of VNAQDKF-GKT AFDISIDNGNEDLAEILQ (SEQ ID NO: 48).

In another embodiment the repeat-motif-molecule is a leucine-rich-repeat-motif-molecule (LRR). Methods for making leucine-rich-repeat-motif-molecules are reported in WO 2006/083275.

In general antibodies have activities selected from a neutralizing activity, a targeting activity for a toxic moiety, or an effector function.

In FIG. 1 the domain architecture of an antibody is shown. A full length antibody comprises two so called light chains and two so called heavy chains. Each of the light chains in turn comprises a light chain variable domain and a light chain constant domain. The light chain constant domain is selected from a kappa type domain or a lambda type domain. Each of the heavy chains in turn comprises a heavy chain variable domain, a first heavy chain constant domain (CH1), a hinge region, a second heavy chain constant domain (CH2), a third heavy chain constant domain (CH3), and optionally a fourth heavy chain constant domain (CH4). In addition comprises a full length antibody disulfide bonds between the light chain constant domain and the first heavy chain constant domain as well as two disulfide bonds between the second heavy chain constant domains of two heavy chains.

In one embodiment the conjugation partner in the GEMOC is a full length antibody heavy chain or a full length antibody light chain but each without a variable domain. In one embodiment the conjugation partner in the GEMOC is an antibody heavy chain or an antibody light chain each with a variable domain. In another embodiment the repeat-motif-molecule is conjugated to the C-terminus of the respective antibody chain either directly of via a peptidic linker. In one embodiment the GEMOC comprises two GEMOCs of the previous embodiment.

In one embodiment the conjugation partner is an antibody light or heavy chain of an anti-Aβ antibody. Such an anti-Aβ antibody and the corresponding nucleic acid sequences are, for example, reported in WO 2003/070760 or US 2005/0169925 or in SEQ ID NO: 50 to 55 or a variant thereof.

The conjugates as reported herein comprise various variants containing one or more repeat-motif-molecule, each of them binding to the same target molecule or to different target molecules. In the conjugates as reported herein to one terminus of the non-repeat-motif-molecule, i.e. the conjugation partner, irrespective of being the C-terminus or the N-terminus, only one, i.e. a single repeat-motif-molecule is covalently linked.

A first variant is a conjugate comprising two or more repeat-motif-molecules, each binding to the same or different target molecules, wherein each pair of repeat-motif-molecules is joined by a peptidic linker. In one embodiment the number of repeat-motif-molecules is selected from two, three, four, five, six, seven, eight, nine, or ten. In FIG. 2 exemplary conjugates comprising two or more repeat-motif-molecules joint by peptidic linkers are shown.

A second variant is a conjugate comprising one or more repeat-motif-molecules and one or more non-repeat-motif-molecule. Each of the repeat-motif-molecules binds to the same or a different target molecule. The non-repeat-motif-molecule provides the scaffold to which the one or more repeat-motif-molecules are covalently linked, optionally and independently of each other via a peptidic linker. In one embodiment the non-repeat-motif-molecule is selected from antibody CL domain, antibody CH1 domain, antibody hinge region, antibody CH2 domain, antibody CH3 domain, antibody CH4 domain, membrane anchor motifs, transmembrane domains, glycosylation tag sequences, purification or detection tag sequences, or a combination of one or more thereof, either natural occurring or engineered variants thereof. In one embodiment the non-repeat-motif-molecule comprises two or more polypeptides covalently linked together by one or more disulfide bond(s). In one embodiment the non-repeat-motif-molecule is an antibody Fc-part. In one embodiment the non-repeat-motif-molecule is a dimer consisting of two monomers each comprising in N- to C-terminal direction a heavy chain hinge region, a CH2 domain and a CH3 domain, or a dimer consisting of two monomers each comprising in N- to C-terminal direction a CH1 domain, a heavy chain hinge region, a CH2 domain and a CH3 domain, or a tetramer comprising two monomers each comprising in N- to C-terminal direction a CH1 domain, a heavy chain hinge region, a CH2 domain and a CH3 domain and two monomers comprising a light chain constant domain. In another embodiment each of the monomers independently of each other further comprises a variable domain.

The term "peptidic linker" denotes linkers of natural and/or synthetic origin comprising amino acid residues connected to each other via peptide bonds. They consist of a linear amino acid chain wherein the 20 naturally occurring amino acids are the monomeric building blocks. The chain has a length of from 1 to 50 amino acid residues, in one embodiment between 3 and 28 amino acid residues, in a further embodiment between 4 and 20 amino acid residues. The linker may contain repetitive amino acid sequences or sequences of naturally occurring polypeptides. The linker has the function to ensure that the two components connected through the linker can fold correctly and be presented properly due to steric and rotational freedom. In one embodiment the linker is a "synthetic peptidic linker" that is designated to be rich in glycine, glutamine, and/or serine residues. These residues are arranged e.g. in small repetitive units of up to five amino acids, such as (G)GGGS, (Q)QQQG, or (S)SSSG (SEQ ID NO: 14, 15, and 16). This small repetitive unit may be repeated for two to five times to form a multimeric unit. Other synthetic peptidic linkers are composed of a single amino acid, that is repeated between 10 to 20 times, such as e.g. serine in the linker GSSSSSSSSSSSSSSSG (SEQ ID NO: 17). In one embodiment the linker is selected from [GQ4]3GNN (SEQ ID NO: 18), LSLSPGK (SEQ ID NO: 19), LSPNRGEC (SEQ ID NO: 20), LSLSGG (SEQ ID NO: 21), LSLSPGG (SEQ ID NO: 22), G3[SG4]2SG (SEQ ID NO: 23), or G3[SG4]2SG2 (SEQ ID NO: 24).

In one embodiment the linker has from 4 to 20 amino acid residues. In one embodiment the linker is the same between the repeat-motif-molecules, in another embodiment the conjugate contains linker with two or more different amino acid sequences. In a further embodiment the linker is selected from (G3S), (G3S)2, (G3S)3, (G3S)4, (G3S)5, (G4S), (G4S)2, (G4S)3, (G4S)4, (G4S)5 (SEQ ID NO: 14 and 25 to 33), preferably from (G4S)3 and (G4S)4 (SEQ ID NO: 31 and SEQ ID NO: 32).

In one embodiment the conjugate as reported herein comprises one repeat-motif-molecule and one non-repeat-motif-molecule, and optionally a peptidic linker in between these molecules. The repeat-motif-molecule is covalently linked either to the C-terminus or to the N-terminus of the non-repeat-motif-molecule or to one of the C-termini or to one of the N-termini of the polypeptides forming the non-repeat-motif-molecule.

In FIGS. 3 to 5 exemplary conjugates of the embodiments of the second variant are shown. In FIG. 3 conjugates of one repeat-motif-molecule to the N-terminus and C-terminus of the different individual antibody domains are shown. In FIG. 4 conjugates of one repeat-motif-molecule to the N-terminus and C-terminus of combinations of two, three or four antibody domains are shown. In FIG. 5 conjugates of one repeat-motif-molecule to the N-terminus and C-terminus of disulfide bond linked antibody domains (CL-CH1 or hinge-hinge) are shown, optionally these conjugates may comprise in addition further antibody domains except variable domains.

In another embodiment the conjugate as reported herein comprises two repeat-motif-molecule and one non-repeat-motif-molecule, and optionally up to two peptidic linker(s). One repeat-motif-molecule is covalently linked to the C-terminus and one to the N-terminus of the non-repeat-motif-molecule or both are covalently linked to the C-termini or to the N-termini of the polyp eptides forming the non-repeat-motif-molecule or one of the repeat-motif-molecules is covalently linked to a C-terminus and one is covalently linked to an N-terminus of the polypeptides forming the non-repeat-motif-molecule. Therein the C-terminus and the N-terminus are the termini of the same polypeptide or of different polypeptides. In FIGS. 6 to 8 exemplary conjugates of this embodiment are shown. In FIG. 6 the two repeat-motif-molecules are conjugated to a non-repeat-motif-molecule comprising only one C-terminus and one N-terminus, wherein the non-repeat-motif-molecule may comprise one or more antibody domains. In FIGS. 7 and 8 the two repeat-motif-molecules are conjugated to a non-repeat-motif-molecule comprising disulfide bond linked antibody domains, optionally these conjugates may comprise in addition further antibody domains except variable domains.

In a further embodiment the conjugate comprises four repeat-motif-molecule and one non-repeat-motif-molecule, and optionally up to four peptidic linker(s). In this embodiment the non-repeat-motif-molecule comprises at least two polypeptides covalently associated together, in one embodiment via one or more disulfide bonds. In one embodiment the repeat-motif-molecules are covalently linked to the respective number of C-termini and N-termini of the non-repeat-motif-molecule. In another embodiment two of the repeat-motif-molecules are conjugated to each other forming dimeric repeat-motif-molecules and the dimeric repeat-motif-molecule is in turn conjugated to the non-repeat-motif-molecule. In FIGS. 9 to 11 exemplary conjugates of this embodiment are shown. In FIG. 9 the four repeat-motif-molecules are conjugated to a non-repeat-motif-molecule comprising two C-termini and two N-termini, wherein the non-repeat-motif-molecule may comprise one or more antibody domains. In FIGS. 10 and 11 the four repeat-motif-molecules are conjugated to a non-repeat-motif-molecule comprising disulfide bond linked antibody domains, optionally these conjugates may comprise in addition further antibody domains except variable domains.

In still another embodiment the conjugate comprises six repeat-motif-molecule and one non-repeat-motif-molecule, and optionally up to six peptidic linker(s). In this embodiment the non-repeat-motif-molecule comprises at least two polypeptides covalently associated together, in one embodiment via one or more disulfide bonds. In one embodiment the repeat-motif-molecules are covalently linked to the respective number of C-termini and N-termini of the non-repeat-motif-molecule. In another embodiment four of the repeat-motif-molecules are conjugated to each other forming dimeric repeat-motif-molecules and the dimeric repeat-motif-molecule is in turn conjugated to the non-repeat-motif-molecule and two repeat-motif-molecules are not conjugated to each other but are each conjugated to a single terminus of the non-repeat-motif-molecule. In FIG. 12 an exemplary conjugate of this embodiment is shown.

In a further embodiment the conjugate comprises eight repeat-motif-molecule and one non-repeat-motif-molecule, and optionally up to eight peptidic linker(s). In this embodiment the non-repeat-motif-molecule comprises at least two polypeptides covalently associated together, in one embodiment via one or more disulfide bonds. In one embodiment the repeat-motif-molecules are covalently linked to the respective number of C-termini and N-termini of the non-repeat-motif-molecule. In another embodiment of from two to eight of the repeat-motif-molecules are conjugated to each other forming dimeric repeat-motif-molecules and the dimeric repeat-motif-molecule is in turn conjugated to the non-repeat-motif-molecule and the remaining number of repeat-motif-molecules are not conjugated to each other but are each conjugated to a single terminus of the non-repeat-motif-molecule.

The repeat-motif-molecule may be a derivative of a scaffold selected from the group consisting of CTLA-4 (Evibody), lipocalin, protein A derived molecules such as the Z-domain of protein A (Affibody, SpA), A-domain (Avimer, Maxibody), heat shock proteins such as GroEl and GroES, transferrin (transbody), peptide aptamer, C-type lectin domain (Tetranectin), human y-crystallin and human ubiquitin (affilins), PDZ domains, scorpion toxin, kunitz type domains of human protease inhibitors, and fibronectin (adnectin), repeat-motif-molecules derived from the Src homology domains (e.g. SH2 or SH3 domains), repeat-motif-molecules derived from PDZ domains, repeat-motif-molecules derived from the beta-lactamase, repeat-motif-molecules derived from high affinity protease inhibitors, repeat-motif-molecules derived from small disulfide binding protein scaffolds such as scorpion toxins, repeat-motif-molecules comprising repeat binding domains such as the EGF-like domain, the Kringle-domain, the PAN domain, the Gla domain, the SRCR domain, the Kunitz domain, the Bovine pancreatic trypsin inhibitor domain, the Kazal-type serine protease inhibitor domain, the Trefoil (P-type) domain, the von Willebrand factor type C domain, the anhaphylatoxin-like domain, the CUB domain, the thyroglobulin type I repeat, the LDL-receptor class A domain, the Sushi domain, the Link domain, the Thrombospondin type I domain, the immunoglobulin-like domains, the C-type lectin domain, the MAM domain, the von Willebrand factor type A domain, the Somatomedin B domain, the WAP-type four disulfide core domain, the F518 type C domain, the Hemopexin domain, the Laminin-type EGF-like domain, the C2 domain, repeat-motif-molecules derived from Avimers, repeat-motif-molecules derived from Telobodies, repeat-motif-molecules derived from Evibodies, repeat-motif-molecules derived from Microbodies (see e.g. Jeong, K. J. and Silverman, J., Nat. Biotechnol. 23 (2005) 1493-1494; Panni, S., et al., J. Biol. Chem. 277 (2002) 21666-21674; Schneider, S., et al., Nat. Biotechnol. 17 (1999) 170-175; Legendre, D., et al., Protein Sci. 11 (2002) 1506-1518; Stoop, A. A., et al., Nat. Biotechnol. 21 (2003) 1063-1068; Vita, C., et al., Proc. Natl. Acad. Sci. USA 92 (1995) 6404-6408; WO 2006/055689; US 2006/0234299).

In one embodiment the GEMOC comprises a conjugation partner selected from an antibody substructure, minibody, adnectin, anticalin, affibody, affilin, knottin, glybody, C-type lectin-like domain protein, designed ankyrin-repeat proteins (DARPin), Tetranectin, kunitz domain protein, Thioredoxin, cytochrome b562, zinc finger scaffold, Staphylococcal nuclease scaffold, fibronectin or fibronectin dimer, tenascin, N-cadherin, E-cadherin, ICAM, titin, GCSF-receptor, cytokine receptor, glycosidase inhibitor, antibiotic chromoprotein, myelin membrane adhesion molecule PO, CD8, CD4, CD2, class I MHC, T-cell antigen receptor, CD 1, C2 and I-set domains of VCAM-1, 1-set immunoglobulin domain of myosin-binding protein C, 1-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, and thaumatin.

In one embodiment the conjugation partner is an anticalin. In a further embodiment the anticalin is anticalin A-44. In one embodiment the conjugate comprises the amino acid sequence of SEQ ID NO: 64, and/or SEQ ID NO: 65, and/or SEQ ID NO: 66. It has been found that GEMOCS comprising an anticalin can be expressed at higher yields compared to GEMOCS comprising DARPins. In one embodiment the anticalin is fused to an antibody Fc-part. In another embodiment the Fc-part is the Fc-part of human IgG1 or human IgG4 with or without mutations. Exemplary mutations are the amino acid exchanges L234A and L235A for IgG1, and S228P and L235E for IgG4.

It has been found that it is advantageous for the production of GEMOCS comprising repeat-motif-molecules fused to the N-termini of an antibody Fc-part, such as a human IgG1 Fc-part or a human IgG4 Fc-part with or without the above identified amino acid exchanges, that the hinge region comprises three interchain disulfide bonds. Compared to conjugates containing two interchain disulfide bridges in the hinge region conjugates with three interchain disulfide bridges in the hinge region can be produced with reduced by product content, especially with respect to fragmentation.

The herein before reported GEMOCs comprising two or more repeat-motif-molecules provide a possibility for bispecific, trispecific or tetraspecific target molecule binding constructs. The term "bispecific" denotes that the GEMOC comprises at least two repeat-motif-molecules binding to two different target molecules. The term "trispecific" denotes that the GEMOC comprises at least three repeat-motif-molecules binding to three different target molecules. The term "tetraspecific" denotes that the GEMOC comprises at least four repeat-motif-molecules binding to four different target molecules.

In case of a GEMOC comprising antibody domains the production of mispaired byproducts as well as fragments has to be circumvented or at least minimized in order to achieve acceptable production yields, and to avoid the requirement for sophisticated purification procedures. An approach to circumvent the problem of mispaired byproducts, which is known as 'knobs-into-holes', aims at forcing the pairing of two different conjugates each comprising an antibody heavy chains CH3 domain by introducing mutations into the CH3 domains to modify the contact interface. On one chain bulky amino acids are replaced by amino acids with short side chains to create a 'hole'. Concomitantly, amino acids with large side chains are introduced into the other CH3 domain, to create a 'knob'. By coexpressing these two modified conjugates high yields of heterodimer formation ('knob-hole') versus homodimer formation ('hole-hole' or 'knob-knob') was observed (see e.g. Ridgway, J. B., Protein Eng. 9 (1996) 617-621; WO 96/027011). A further approach to clearly reduce the formation of mispaired byproducts is the use of a technology called "domain-exchange" or "crossover". Therein the specific interaction between antibody CL and CH1 domains is exploited. In one embodiment the conjugation partner in the GEMOCs as reported herein comprise two polypeptides whereof one comprises an antibody light chain constant domain (CL) and the other comprises an antibody heavy chain first constant domain (CH1). Exemplary bispecific GEMOCs are shown in FIG. 13.

The term "target molecule" denotes a molecule that is complementary to and provides for interaction sites for interacting with a repeat-motif-molecule. In one embodiment the target molecule is selected from cell surface molecules, soluble cell surface molecules, cytokines, hormones, enzymes, immunoglobulins, toxins, virus particle proteins, plaque proteins and plaque precursor proteins, or nanoparticles.

The GEMOCs as reported herein comprise a conjugation partner providing a scaffold for presenting the repeat-motif-molecule(s). This conjugation partner can provide in addition further functionality, such as e.g. a receptor binding functionality. The conjugation partner is in one embodiment selected from antibody domains, in one embodiment it comprises the CH2 domain of an antibody. The antibody CH2 domain provides for the Fc-Receptor binding functionality which is required for ADCC or CDC. In another embodiment the conjugation partner is a molecule that can multimerize or associate with other GEMOCs comprising the same conjugation partner or the respective complementary association partner.

Such a multimerizing conjugation partner or pair of conjugation partner and complementary association partner is in one embodiment selected from leucine zippers, the pair comprising the regulatory subunit of cAMP-dependent protein kinase A (PKA) and the anchoring domain of a kinase anchoring proteins (AKA).

The employed conjugation partner in the GEMOCs should be of human origin, highly stable with regard to fold and degradation, "inert", i.e. no cytokine or signaling function, easy and economic in production, allow for further processing (e.g. proteolytic cleavage, chemical modification of peptide, post translational modification), of appropriate size (no renal filtration) or other systemic elimination, and not immunogenic.

The term "multimerizing conjugation partner" denotes molecules capable of covalently or non-covalently associating two or more individual GEMOCs. Multimerizing conjugation partners are in one embodiment selected from the leucine zipper domain (Kostelny, S. A., et al., J. Immunol. 148 (1992) 1547-1553; de Kruif, J., et al., J. Biol. Chem. 271 (1996) 7630-7634), a yeast GCN4 leucine zipper, an isoleucine zipper domain, the helix-turn-helix motif (Pack, P., et al., Biotechnol. 11 (1993) 1271-1277), the max-interacting proteins and related molecules (U.S. Pat. No. 5,512,473), the polyglutamic acid-polylysine domains (U.S. Pat. No. 5,582,996), the natural or engineered pair of heavy chain CH2-CH3 domain, the natural or engineered pair of heavy chain CH1 domain-light chain constant domain (Mueller, K. M., et al., FEBS Lett. 422 (1998) 259-264), the 180 amino acid carboxyl terminal domain of the TATA binding protein (Colemen, R. A., et al., J. Biol. Chem. 270 (1995) 13842-13849), VCAM and VLA-4, integrins and extracellular matrix proteins, integrins and cell surface molecules (e.g. CD54 or CD102), ALCAMs, glutathione transfereases, SRCR domains, a receptor dimer pair (e.g., interleukin-8 receptor (IL-8R), integrin heterodimers (such as LFA-1 and GPIIIb/IIIa), or only the dimerization region(s) thereof, dimeric ligand polypeptides (e.g. nerve growth factor (NGF), neurotrophin-3 (NT-3), interleukin-8 (IL-8), vascular endothelial growth factor (VEGF), and brain-derived neurotrophic factor (BDNF) (see e.g. Arakawa, T., et al., J. Biol. Chem. 269 (1994) 27833-27839; Radziejewski, C., et al., Biochem. 32 (1993) 13350-6)), or only the dimerization region(s) thereof, generally a pair of cysteine residues able to form a disulfide bond, a pair of peptides or polypeptides, each comprising at least one cysteine residue (e.g. from about one, two or three to about ten cysteine residues) such that disulfide bond(s) can form between the peptides or polypeptides, generally coiled-coil domains (see e.g. Lupas, A., et al., Science 252 (1991) 1162-1164), the tetramerization domain of p53, the N-terminal residues (amino acids 20-80) of cartilage oligomeric matrix protein (COMP), alpha-helical sequences (see e.g. Eisenberg, D., et al., Protein 1 (1986) 16-22; Ho, S. P. and DeGrado, W. F., J. Am. Chem. Soc. 109 (1987) 6751-6758; Regan, L. and DeGrado, W. F., Science 241 (1988) 976-978; Hill, C. P., et al., Science 249 (1990) 543-546; Plückthun, A. and Pack, P., Immunotechnol. 3 (1997) 83-105). In one embodiment the multimerizing conjugation partner is selected from natural or engineered pairs of heavy chain CH2 and CH3 domains, natural or engineered pairs of heavy chain CH1 domain and light chain constant domain, natural or engineered heavy chain hinge region. In a further embodiment the multimerizing conjugation partner is selected from natural or engineered pairs of heavy chain CH2 and CH3 domains, natural or engineered pairs of heavy chain CH1 domain and light chain constant domain, from natural or engineered sequences of heavy chain hinge region and CH2 and CH3 domains. In another embodiment the multimerizing conjugation partner is selected from natural or engineered pairs of heavy chain CH2 and CH3 domains, natural or engineered pairs of heavy chain CH1 domain and light chain constant domain.

Antibodies can proteolytically be cleaved by the enzyme papain close to the N-terminal side of each hinge region resulting in two antigen binding fragments (Fab) and one constant region fragment (Fc). The Fab fragment consists of the entire light chain and the N-terminal a fragment of the heavy chain comprising the VH and CH1 domain. The Fc-part in turn comprises the remaining domains of the two heavy chains linked by the disulfide bonds in the hinge region.

The Fc-part of an antibody interacts with components of the immune system, e.g. the complement cascade (complement dependent cytotoxicity (CDC)) or by binding to the Fc-gamma receptors (antibody dependent cell cytotoxicity (ADCC)) or cytotoxic effector cells. To alter the effector function of the Fc-part substitutions of amino acid residues can be made (U.S. Pat. No. 5,648,260; U.S. Pat. No. 5,624,821). The Fc-part is responsible for mediating effector functions such as cytokine induction, ADCC, phagocytosis, complement dependent cytotoxicity (CDC) and half-life/clearance rate of antibody and antigen-antibody complexes. The Fc-part generally starts at position 226 (Cys) or 230 (Pro) and extends to the C-terminus of the antibody heavy chains.

The GEMOCs as reported herein are glycosylated proteins comprising one or more carbohydrate residues. In vivo protein production comprises post-translational modification steps, especially glycosylation. The sugar (glycosyl) residues are added enzymatically to the protein amino acid sequence at N- or O-glycosylation motifs. Antibodies for example are glycosylated proteins with one or more carbohydrate moieties in the Fc-part and also in the variable domains. The carbohydrate moieties of the Fc-part are at least partly responsible for the effector function and only less important for antigen binding or half-life of the antibody (Jefferis, R., Biotechnol. Prog. 21 (2005) 11-16).

Depending on the amino acid sequence of the constant region of the heavy chains, antibodies (immunoglobulins) are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs are the heavy chain constant regions of immunoglobulins are called α (IgA), δ (IgD), ε (IgE), γ (IgG), and μ (IgM), respectively. Depending on the amino acid sequence of the constant domain the antibody light chains are denoted as kappa (κ) or lambda (λ) light chain.

The term "glycosylated" denotes that oligosaccharides are attached to at least one amino acid residue. Due to the involvement of a multitude of enzymes in the post-translational glycosylation in cells, i.e. in vivo, a recombinantly produced polypeptide is obtained having a glycosylation patter, i.e. a glycosylation heterogeneity, due to the cell expressing the polypeptide. Thus, therefore a recombinantly produced polypeptide comprises not only a single, defined N- or O-linked oligosaccharide at a specified amino acid residue, but is a mixture of polypeptides each having the same amino acid sequence but comprising different oligosaccharides at this specified amino acid position, i.e. has a glycosylation pattern. Therefore, a glycosylated EMOC comprises a group of conjugates each with the same amino acid sequence but with different oligosaccharides attached to a specified amino acid position. The term "oligosaccharide" as used within this application denotes a polymeric saccharide comprising two or more covalently linked monosaccharide units. In one embodiment the oligosaccharide attached to a glycosylation site is a mixture of oligosaccharides obtained by the expression of the conjugate in a CHO cell or HEK293 cell, i.e. the oligosaccharide is a mixture of oligosaccharide obtained by post-translational modification of the cell expressing the conjugate, i.e. it is characteristic for the cell expressing the conjugate. The glycosylation and glycosylation pattern obtained by a cell expressing a polypeptide, i.e. in vivo, is completely different from the glycosylation or glycosylation pattern obtained in vitro.

Another aspect of the current invention is a method for producing the GEMOCs as reported herein by expressing the respective encoding nucleic acid in a mammalian cell.

In detail, herein is reported a method for producing a glycosylated repeat-motif-molecule conjugate in a mammalian cell comprising providing a mammalian cell comprising a nucleic acid encoding the repeat-motif-molecule conjugate, cultivating the cell under conditions suitable for the expression of the repeat-motif-molecule, recovering the glycosylated repeat-motif-molecule from the cell or the cultivation medium and thereby producing the glycosylated repeat-motif-molecule, optionally purifying the recovered glycosylated repeat-motif-molecule.

GEMOCs as reported herein can be produced in mammalian cells, i.e. as in vivo glycosylated repeat-motif-molecule conjugates. It is herein reported a method for the production of repeat-motif-molecule conjugates in a glycosylated form, in one embodiment in an in vivo glycosylated form. Such an in vivo glycosylation, i.e. a glycosylation in the same cell also expressing the repeat-motif-molecule conjugate, is a cell specific post-translational modification. Recombinantly produced polypeptides can be glycosylated in vitro, i.e. after isolation from the producing cell (see e.g. Leung, S., et al., J. Immunol. 154 (1995) 5919-5926; U.S. Pat. No. 5,443,953 for antibodies).

Methods for purifying polypeptides and immunoglobulins are well established and widespread used and are employed either alone or in combination. Such methods are, for example and in certain embodiments, affinity chromatography using microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and preparative electrophoretic methods (such as gel electrophoresis, capillary electrophoresis) (Vijayalakshmi, M. A., Appl. Biochem. Biotech. 75 (1998) 93-102). In one embodiment the chromatography column packing is a chromatography material selected from an affinity chromatography material, or an ion exchange chromatography material, or a thiophilic adsorption chromatography material, or a hydrophobic interaction chromatography material, or an aromatic adsorption chromatography material, or a metal chelate affinity chromatography material, or a size exclusion chromatography material.

To produce a secreted polypeptide, the structural gene of interest also may comprise a DNA segment that encodes a signal sequence/leader peptide. The signal sequence directs the newly synthesized polypeptide to and through the membrane of the Endoplasmic Reticulum (ER) where the polypeptide can be routed for secretion. The signal sequence is cleaved off by a signal peptidases during the protein crosses the ER membrane. As for the function of the signal sequence the recognition by the host cell's secretion machinery is essential. Therefore the used signal sequence has to be recognized by the host cell's proteins and enzymes of the secretion machinery.

Translational regulatory elements include a translational initiation (AUG) and stop codon (TAA, TAG or TGA). An internal ribosome entry site (IRES) can be included in some constructs.

Thus, another aspect as reported herein is a nucleic acid for expression of a repeat-motif-molecule conjugate in a mammalian cell comprises the following elements:
the immediate early enhancer and promoter from the human cytomegalovirus,
a 5'-untranslated region of an antibody germline gene,
an immunoglobulin heavy chain signal sequence,
the repeat-motif-molecule conjugate's encoding sequence,
a polyadenylation ("poly A") signal sequence.

In one embodiment the 5'-untranslated region of an antibody germline gene is of a human antibody germline gene. In another embodiment the immunoglobulin heavy chain signal sequence is a murine or human immunoglobulin heavy chain signal sequence. In a further embodiment the immunoglobulin heavy chain signal sequence includes a signal sequence intron (signal sequence 1, intron, signal sequence 2 [L1-intron-L2]).

The subject matter presented herein will be exemplified in the following with two model repeat-motif-molecules binding to HER2 (DARPin H10-2-G3, scaffold N2C (2 repeats), Zahnd, C., et al., J. Mol. Biol. 369 (2007) 1015-1028; DARPin 9-26, scaffold N3C (3 repeats), Steiner, D., et al., J. Mol. Biol. 382 (2008) 1211-1227). Four expression constructs for the expression of these GEMOCs in HEK293 cells were tested (in N- to C-terminal direction):
1) leader-peptide–repeat-motif-molecule–hexa-histidine-tag,
2) leader-peptide–repeat-motif-molecule–immunoglobulin Fc fragment,
3) leader-peptide–immunoglobulin Fc fragment–repeat-motif-molecule,
4) leader-peptide–immunoglobulin Fab-fragment–repeat-motif-molecule.

Thus, further aspects as reported herein are the GEMOCs of SEQ ID NO: 10, 11, 12, 13, 34, 35, 36, 37, 38, 39, 40, 41, 42, the GEMOCs comprising SEQ ID NO: 11 and 11, SEQ ID NO: 13 and 13, SEQ ID NO: 11 and 13, SEQ ID NO: 34 and 34, SEQ ID NO: 35 and 35, SEQ ID NO: 34 and 35, SEQ ID NO: 36 and 37, SEQ ID NO: 39 and 39, as well as the respective nucleic acids encoding them, as well as the respective nucleic acids with these encoding nucleic acid sequences and sequence combinations, as well as the methods for producing these GEMOCs.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO: 01 Ankyrin-repeat-motif-molecule amino acid consensus sequence 1.
SEQ ID NO: 02 Ankyrin-repeat-motif-molecule amino acid consensus sequence 2.
SEQ ID NO: 03 Ankyrin-repeat-motif-molecule amino acid consensus sequence 3.
SEQ ID NO: 04 Ankyrin-repeat-motif-molecule amino acid consensus sequence 4.
SEQ ID NO: 05 Ankyrin-repeat-motif-molecule amino acid consensus sequence 5.
SEQ ID NO: 06 Ankyrin-repeat-motif-molecule amino acid consensus sequence 6.
SEQ ID NO: 07 Ankyrin-repeat-motif-molecule amino acid consensus sequence 7.
SEQ ID NO: 08 Ankyrin-repeat-motif-molecule amino acid consensus sequence 8.
SEQ ID NO: 09 Ankyrin-repeat-motif-molecule amino acid consensus sequence 9.
SEQ ID NO: 10 Model repeat-motif-molecule H10-2-G3 with C-terminally conjugated hexa-histidine-tag amino acid sequence.
SEQ ID NO: 11 Model repeat-motif-molecule H10-2-G3 with C-terminally conjugated IgG1 Fc-part.
SEQ ID NO: 12 Model repeat-motif-molecule 9-26 with C-terminally conjugated hexa-histidine-tag amino acid sequence.
SEQ ID NO: 13 Model repeat-motif-molecule 9-26 with C-terminally conjugated IgG1 Fc-part.
SEQ ID NO: 14 to 33 Peptidic linker sequences.
SEQ ID NO: 34 Model repeat-motif-molecule H10-2-G3 with C-terminally conjugated IgG1 Fc-part with two disulfide bonds in the hinge region.
SEQ ID NO: 35 Model repeat-motif-molecule 9-26 with C-terminally conjugated IgG1 Fc-part with two disulfide bonds in the hinge region.
SEQ ID NO: 36 Model repeat-motif-molecule H10-2-G3 with C-terminally conjugated IgG1 Fc-part with CH3-knob-domain.
SEQ ID NO: 37 Model repeat-motif-molecule 9-26 with C-terminally conjugated IgG1 Fc-part with CH3-hole-domain.
SEQ ID NO: 38 Model repeat-motif-molecule H10-2-G3 with C-terminally conjugated model repeat-motif-molecule 9-26.
SEQ ID NO: 39 Model repeat-motif-molecule H10-2-G3 with C-terminally conjugated IgG1 Fc-part with two disulfide bonds in the hinge region with C-terminally conjugated model repeat-motif-molecule 9-26.

SEQ ID NO: 40 Model repeat-motif-molecule H10-2-G3 with C-terminally conjugated model repeat-motif-molecule 9-26 with C-terminally conjugated hexa-histidine-tag.

SEQ ID NO: 41 Model repeat-motif-molecule 9-26 with C-terminally conjugated model repeat-motif-molecule H10-2-G3 with C-terminally conjugated hexa-histidine-tag.

SEQ ID NO: 42 Dimeric model repeat-motif-molecule 9-26 with C-terminally conjugated hexa-histidine-tag.

SEQ ID NO: 43 Human IgG1 constant region.

SEQ ID NO: 44 Human IgG4 constant region.

SEQ ID NO: 45 Human kappa constant region.

SEQ ID NO: 46 Human lambda constant region.

SEQ ID NO: 47 N-terminal capping repeat.

SEQ ID NO: 48 C-terminal capping repeat.

SEQ ID NO: 49 CMV promoter sequence.

SEQ ID NO: 50 Anti-Aβ antibody variable heavy chain domain amino acid sequence.

SEQ ID NO: 51 Anti-Aβ antibody variable heavy chain domain amino acid sequence.

SEQ ID NO: 52 Anti-Aβ antibody variable heavy chain domain amino acid sequence.

SEQ ID NO: 53 Anti-Aβ antibody variable light chain domain amino acid sequence.

SEQ ID NO: 54 Anti-Aβ antibody variable light chain domain amino acid sequence.

SEQ ID NO: 55 Anti-Aβ antibody variable light chain domain amino acid sequence.

SEQ ID NO: 56 Model repeat-motif-molecule H10-2-G3 with C-terminally conjugated hexa-histidine-tag amino acid sequence and introduced engineered glycosylation site at the beginning of the C-capping repeat.

SEQ ID NO: 57 Model repeat-motif-molecule H10-2-G3 with C-terminally conjugated IgG1 Fc-part and thereto C-terminally conjugated membrane anchor domain.

SEQ ID NO: 58 Model repeat-motif-molecule 9-26 with C-terminally conjugated hexa-histidine-tag amino acid sequence and introduced engineered glycosylation site at the beginning of the C-capping repeat.

SEQ ID NO: 59 Model repeat-motif-molecule 9-26 with C-terminally conjugated IgG1 Fc-part and thereto C-terminally conjugated membrane anchor domain.

SEQ ID NO: 60 Model repeat-motif-molecule H10-2-G3 with C-terminally conjugated hexa-histidine-tag amino acid sequence and glycosylation tag in the C-terminal region.

SEQ ID NO: 61 Model repeat-motif-molecule 9-26 with C-terminally conjugated hexa-histidine-tag amino acid sequence and glycosylation tag in the C-terminal region.

SEQ ID NO: 62 Model repeat-motif-molecule H10-2-G3 with C-terminally conjugated hexa-histidine-tag amino acid sequence and glycosylation tag.

SEQ ID NO: 63 Model repeat-motif-molecule 9-26 with C-terminally conjugated hexa-histidine-tag amino acid sequence and glycosylation tag.

SEQ ID NO: 64 Model conjugate comprising anticalin A-44 with hexa-histidine-tag.

SEQ ID NO: 65 Model anticalin A-44 with Fc-tag and three disulfide bridges in the hinge region.

SEQ ID NO: 66 Model anticalin A-44 with Fc-tag and two disulfide bridges in the hinge region.

EXAMPLE 1

Plasmid Construction

Standard methods were used to manipulate DNA as described in Sambrook, J. et al., Molecular cloning: A laboratory manual; Cold Spring Harbor Laboratory Press, Cold Spring Harbor, New York, 1989. The molecular biological reagents were used according to the manufacturer's instructions. Desired gene segments were prepared by gene synthesis. The synthesized gene fragments were cloned into a specified expression vector. The DNA sequence of the subcloned gene fragments were confirmed by DNA sequencing.

Expression Plasmids 9800 and 9803

A gene segment encoding the conjugates of SEQ ID NO: 10 or SEQ ID NO: 12 was cloned into a specified expression plasmid via the unique restriction sites BsmI and Bpu10I. The expression plasmid was designed to combine the conjugate's encoding sequence with a C-terminal hexa-histidine-tag, e.g. for expression in HEK293 cells and subsequent purification. Beside the expression cassette for the conjugate the plasmid comprises:
- an origin of replication from the vector pUC18 which allows replication of this plasmid in *E. coli*, and
- a β-lactamase gene which confers ampicillin resistance in *E. coli*.

The transcription unit of the conjugate's encoding sequence comprises the following elements:
- the immediate early enhancer and promoter from the human cytomegalovirus,
- a 5'-untranslated region of a human antibody germline gene,
- a murine immunoglobulin heavy chain signal sequence including a signal sequence intron (signal sequence 1, intron, signal sequence 2 [L1-intron-L2]) and the unique restriction site BsmI at the 3' end of L2,
- the conjugate's encoding sequence,
- a GSG linker encoding a unique Bpu10I at the 3' end of the conjugate's encoding sequence and in frame with the conjugate's encoding sequence,
- a hexa-histidine-tag at the 3' end of the GSG linker, in frame with the conjugate's encoding sequence and the GSG linker,
- a polyadenylation ("poly A") signal sequence, and
- the unique restriction sites NheI and EagI at the 3'-end of the expressed sequence.

Figure 1:
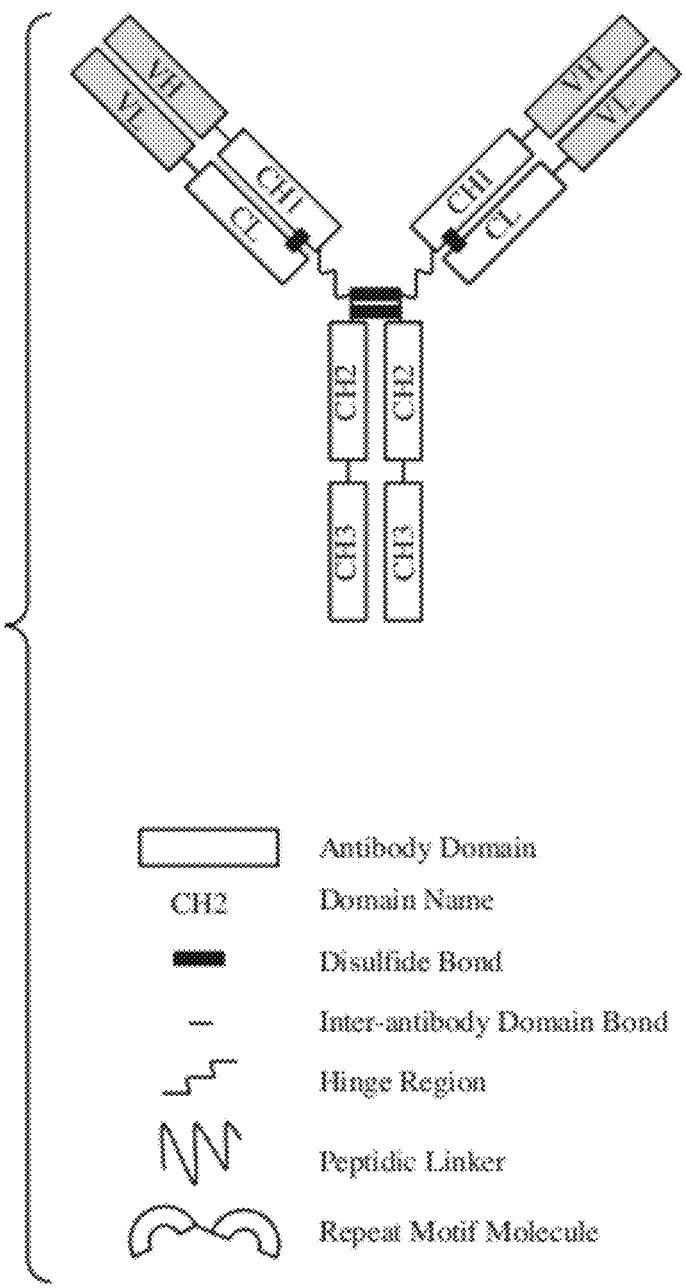
FIG. 1 Schematic presentation of the domain architecture of an antibody and symbol legend for further figures.
Figure 2:
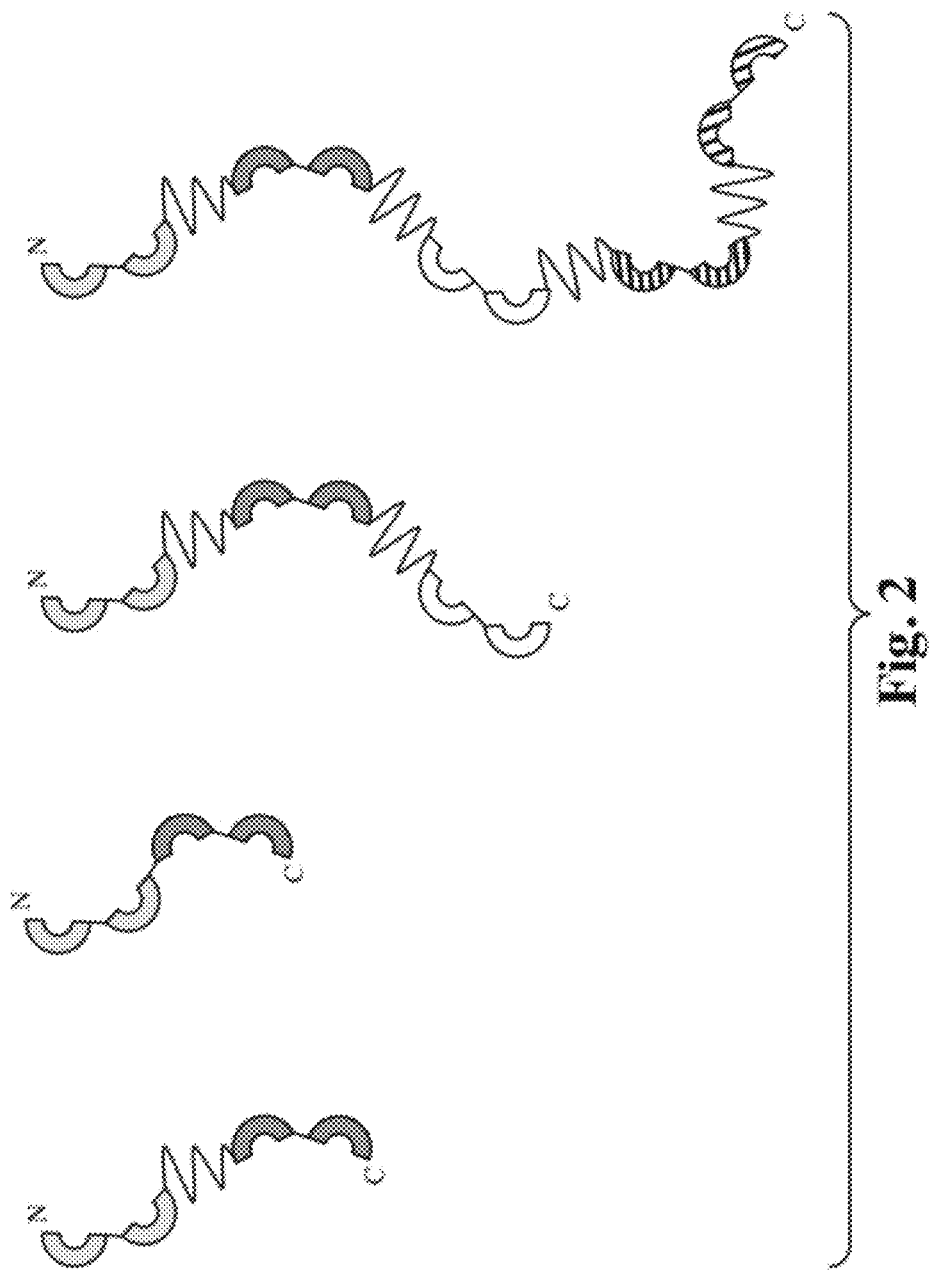
FIG. 2 Exemplary conjugates comprising two or more repeat-motif-molecules.
Figure 3:
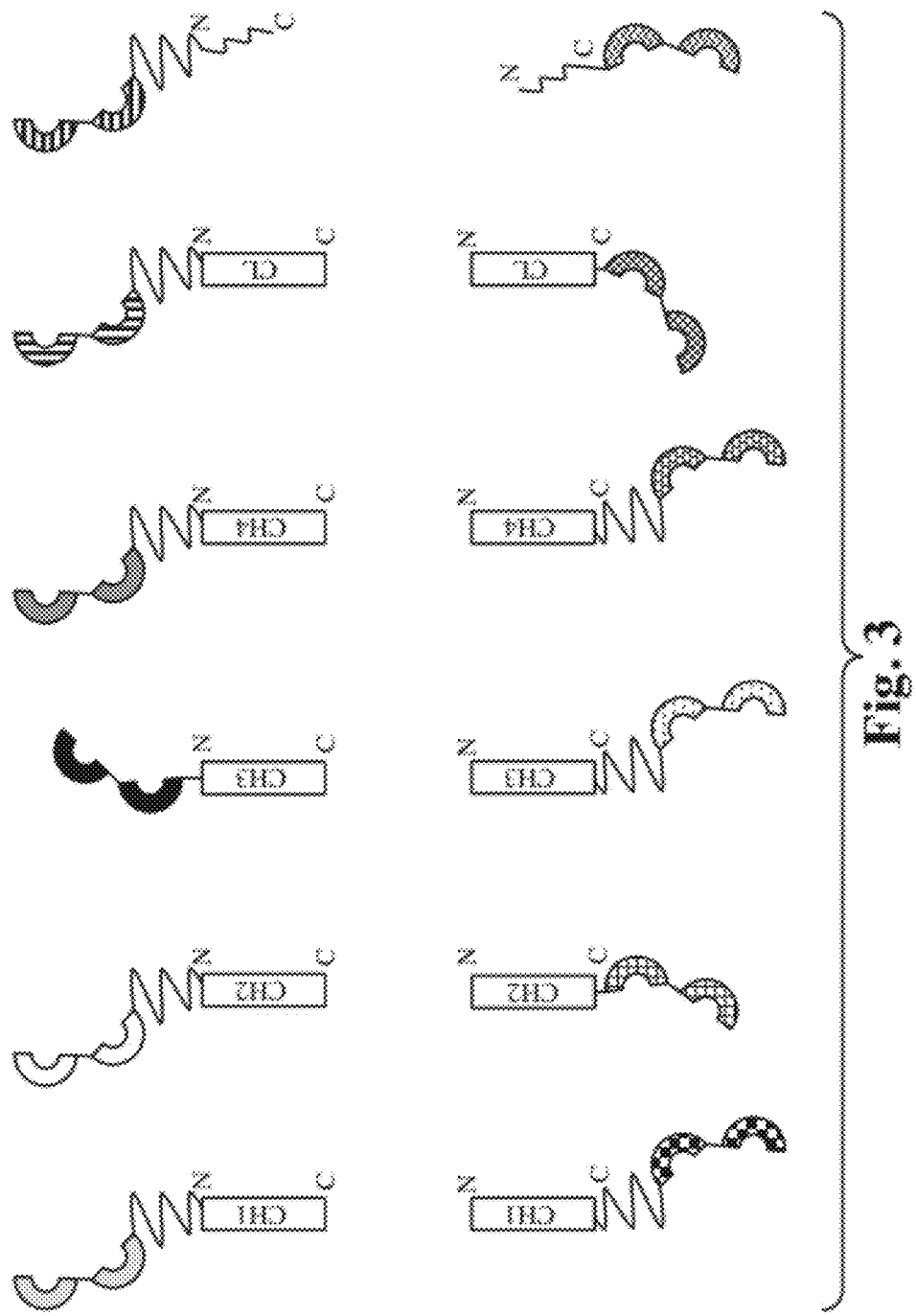
FIG. 3 Exemplary conjugates of one repeat-motif-molecule to the N-terminus and C-terminus of different individual antibody domains.
Figure 4:
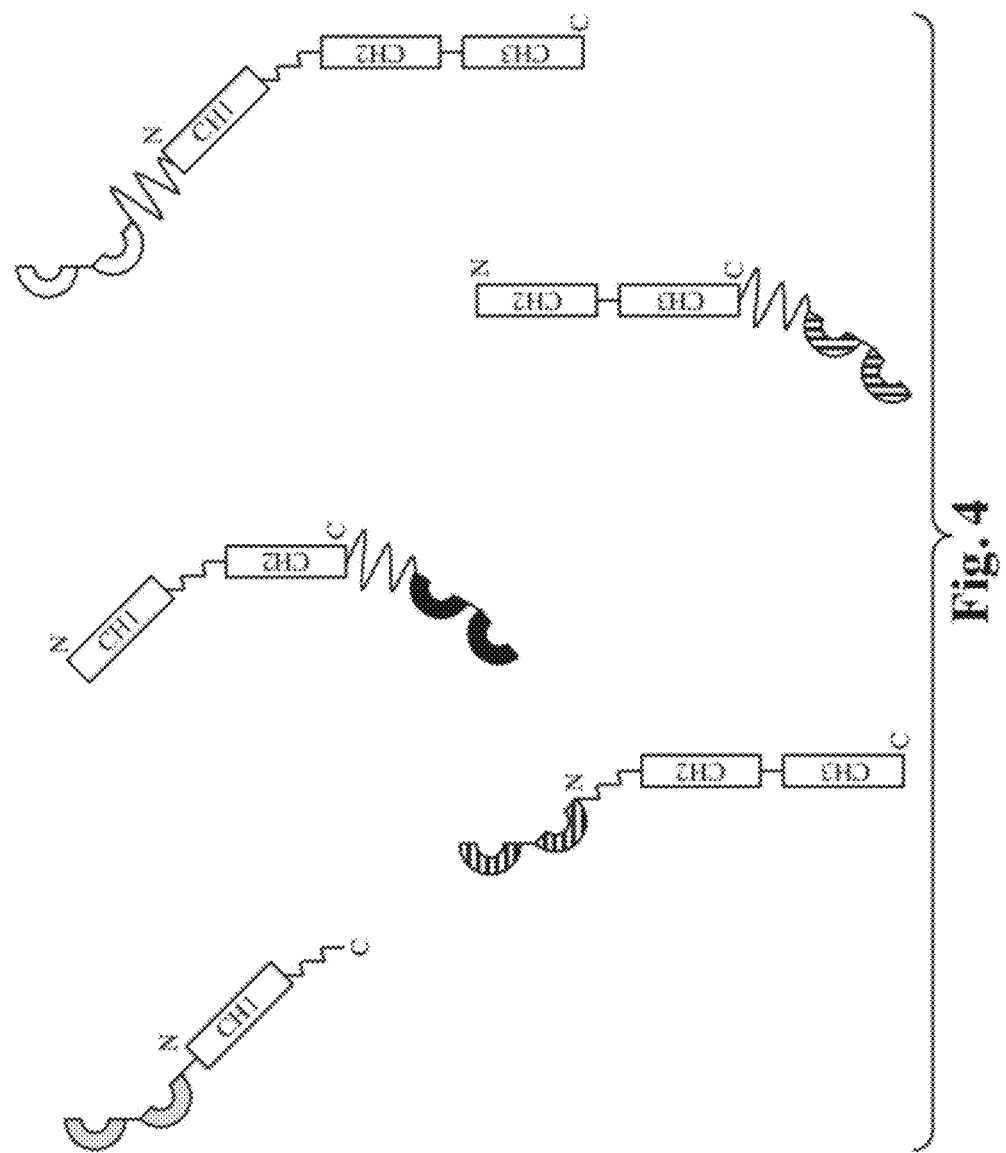
FIG. 4 Exemplary conjugates of one repeat-motif-molecule to the N-terminus and C-terminus of combinations of two, three or four antibody domains.
Figure 5:
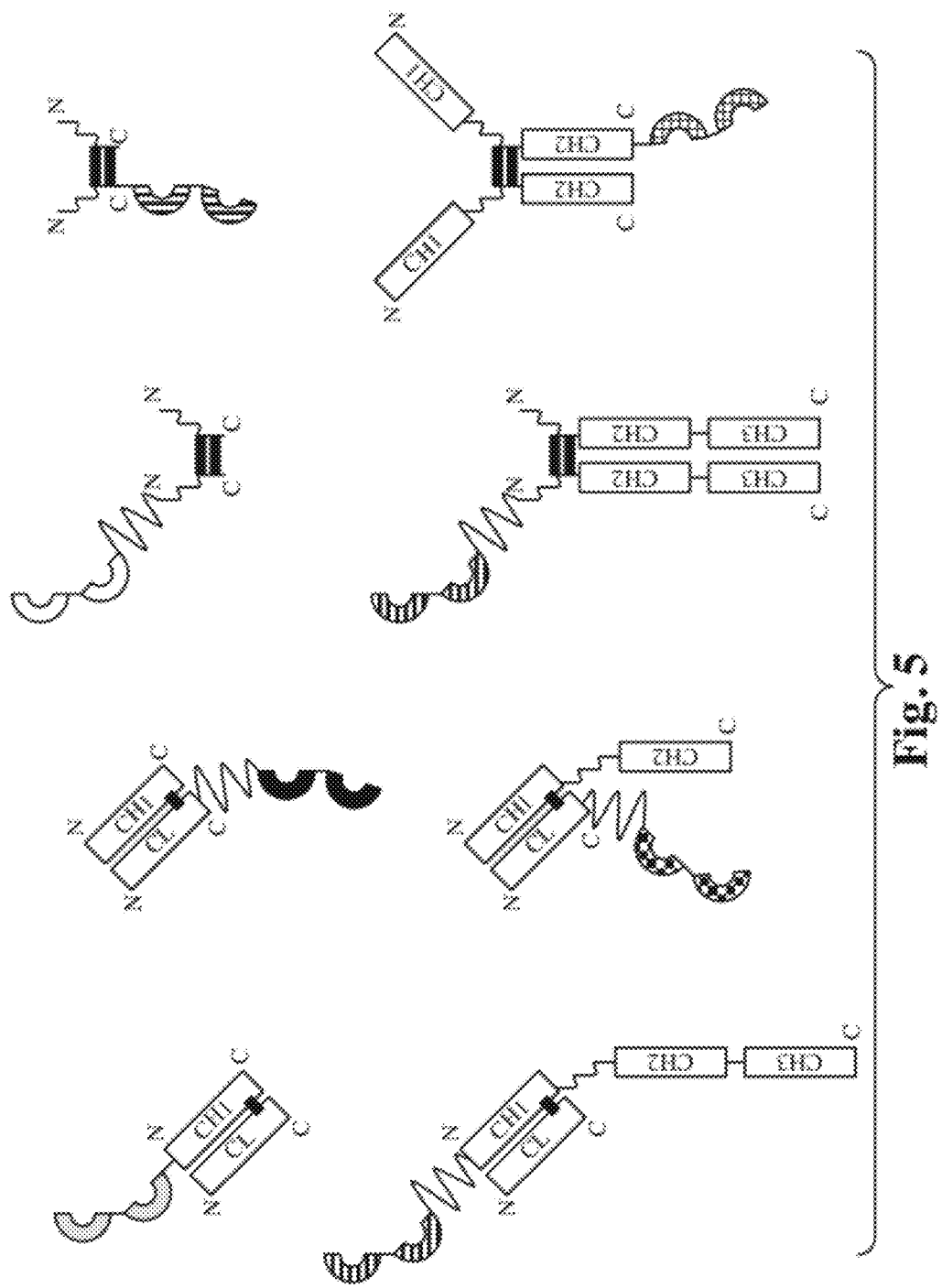
FIG. 5 Exemplary conjugates of one repeat-motif-molecule to the N-terminus and C-terminus of disulfide bond linked antibody domains.
Figure 6:
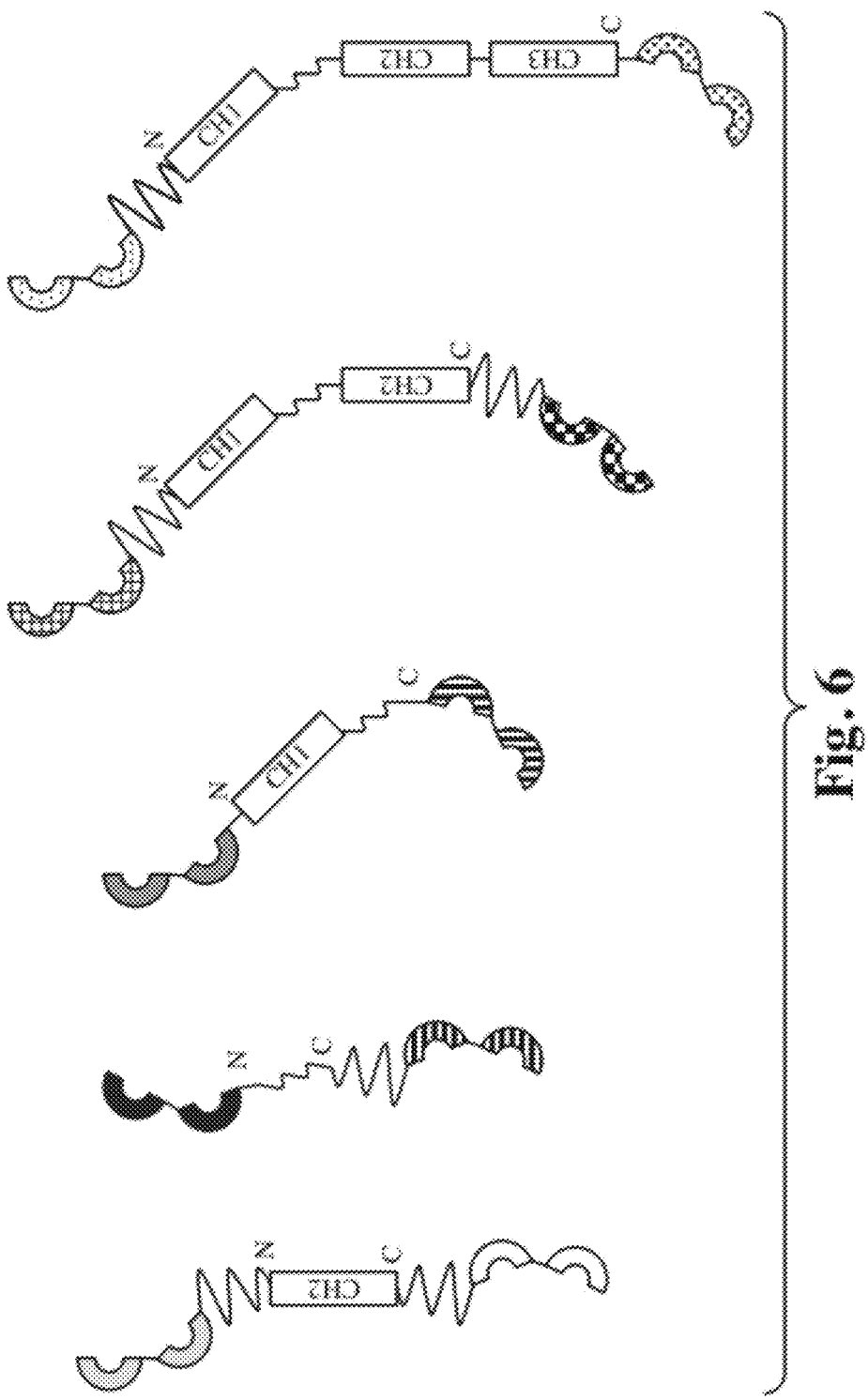
FIG. 6 Exemplary conjugates of two repeat-motif-molecules conjugated to a non-repeat-motif-molecule comprising only one C-terminus and one N-terminus.
Figure 7:
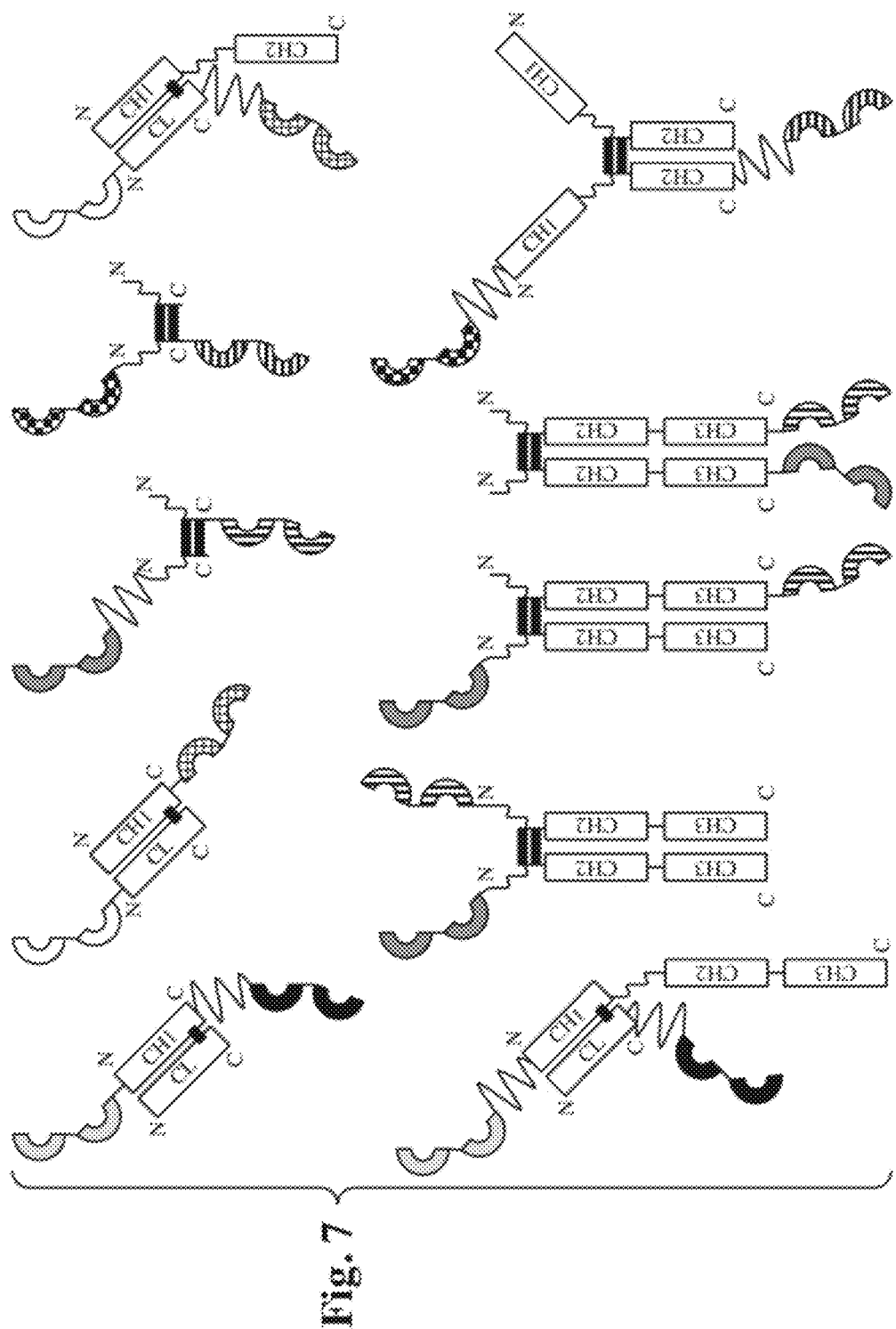
FIG. 7 Exemplary conjugates of two repeat-motif-molecules conjugated to a non-repeat-motif-molecule comprising disulfide bond linked antibody domains (part 1).
Figure 8:
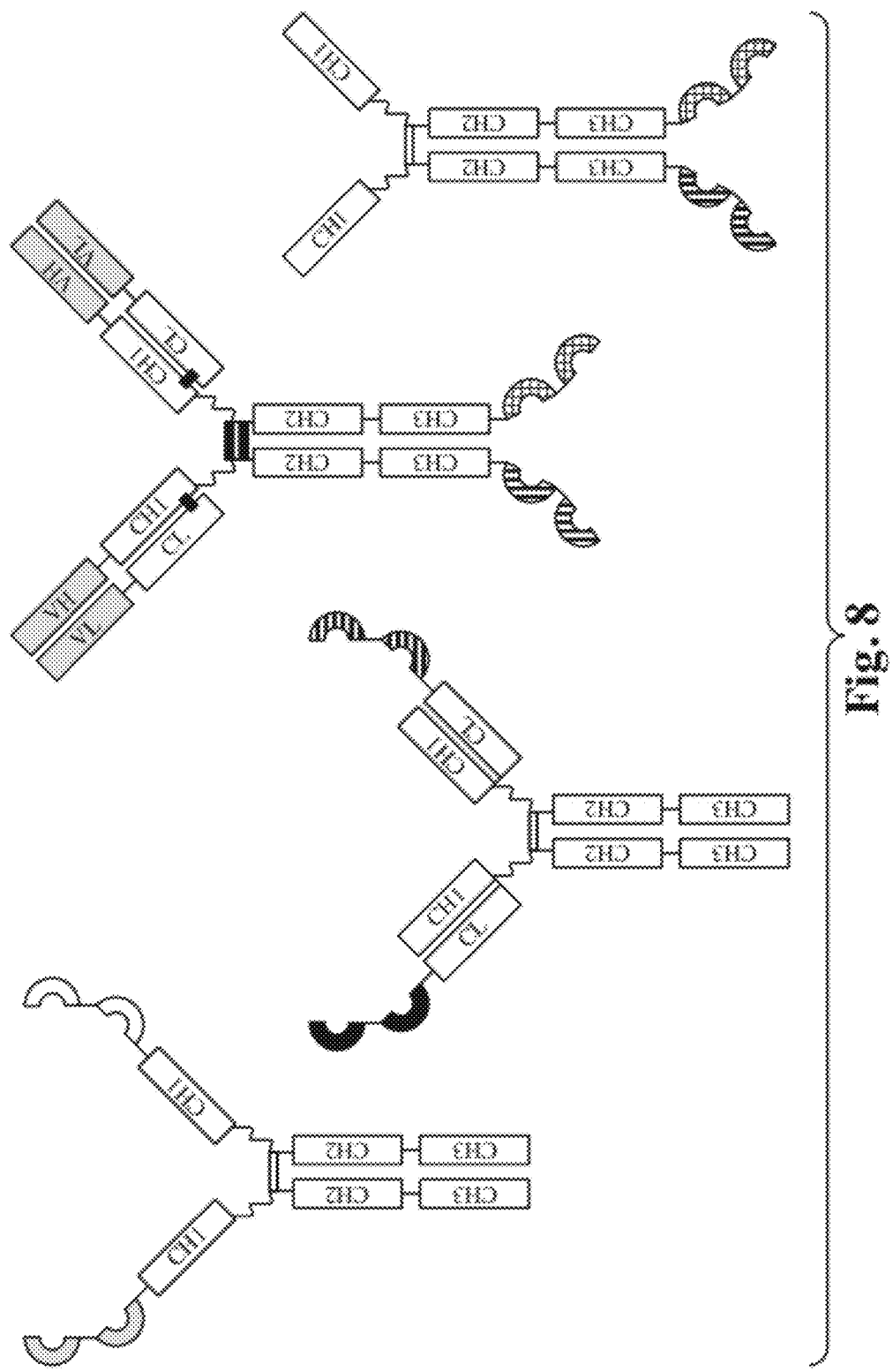
FIG. 8 Exemplary conjugates of two repeat-motif-molecules conjugated to a non-repeat-motif-molecule comprising disulfide bond linked antibody domains (part 2).
Figure 9:
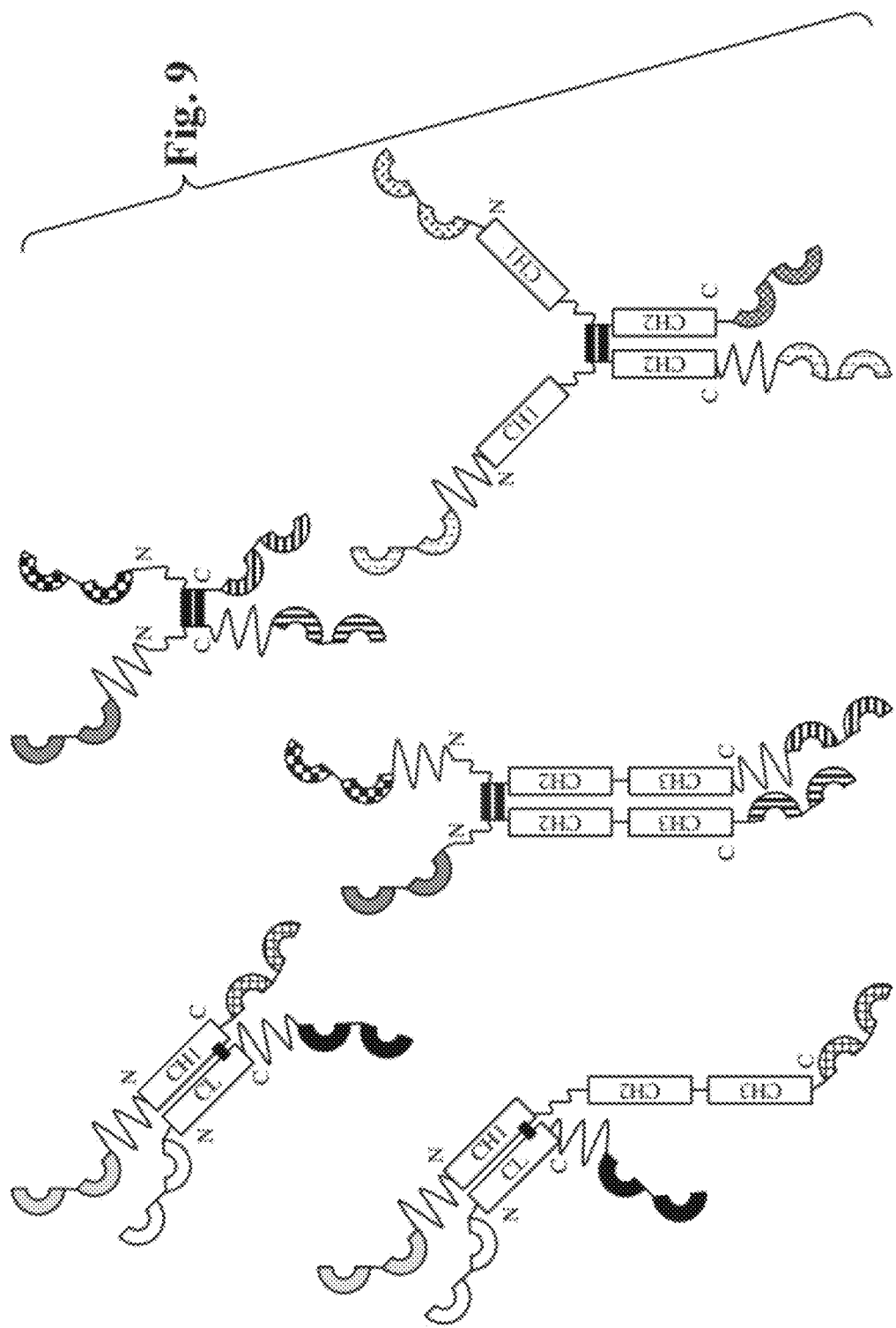
FIG. 9 Exemplary conjugates of four repeat-motif-molecules conjugated to a non-repeat-motif-molecule comprising two C-termini and two N-termini.
Figure 10:
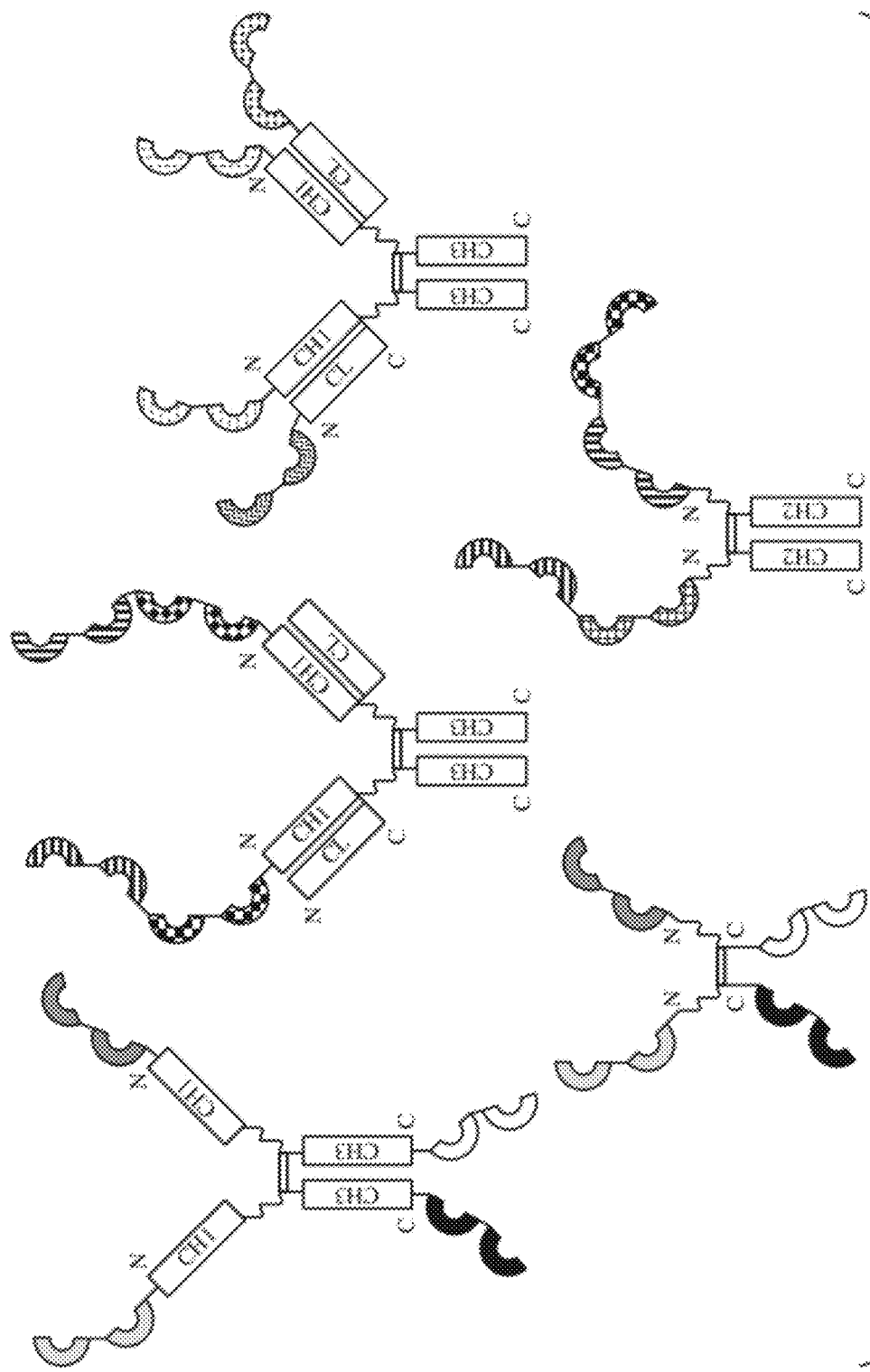
FIG. 10 Exemplary conjugates of four repeat-motif-molecules are conjugated to a non-repeat-motif-molecule comprising disulfide bond linked antibody domains (part 1).
Figure 11:
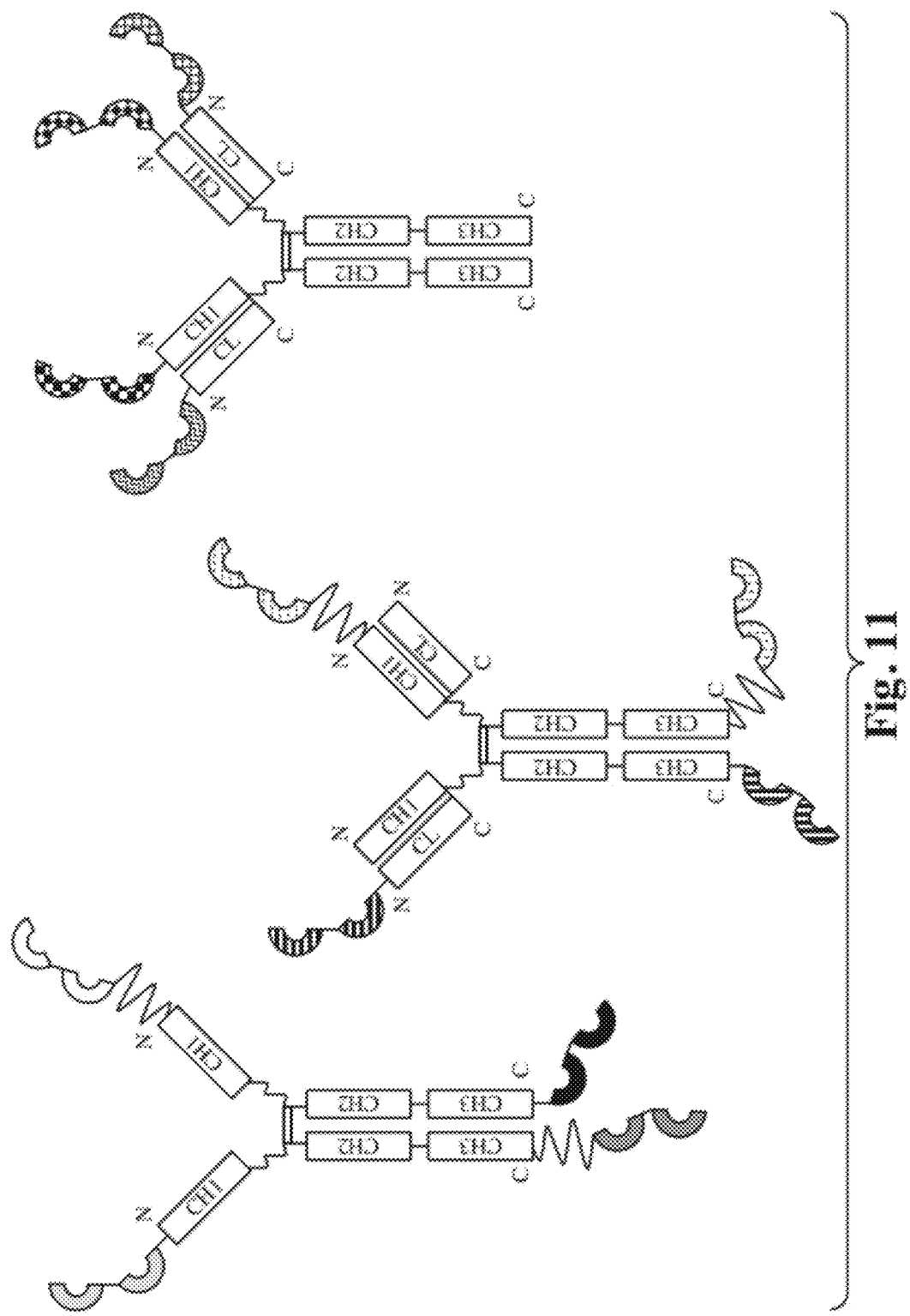
FIG. 11 Exemplary conjugates of four repeat-motif-molecules are conjugated to a non-repeat-motif-molecule comprising disulfide bond linked antibody domains (part 2).
Figure 12:
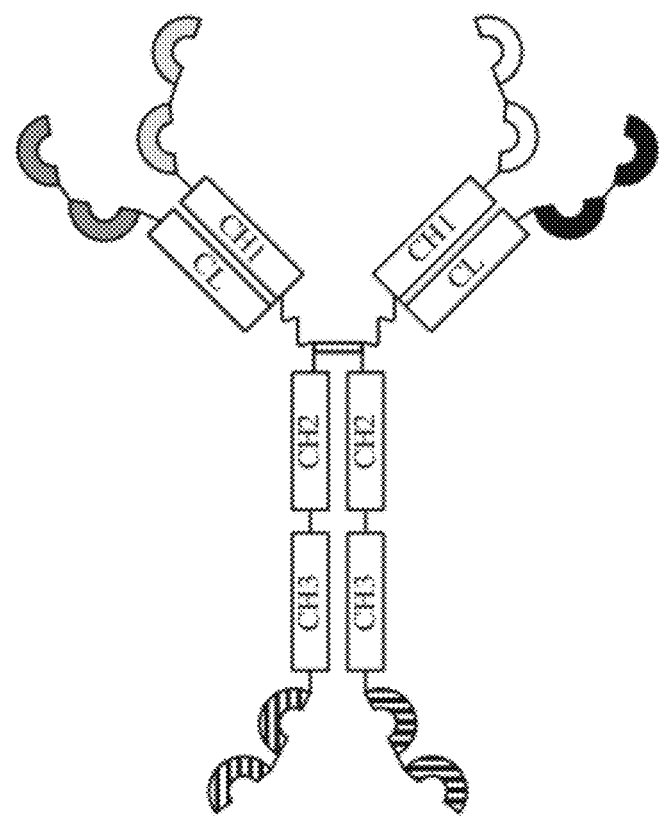
FIG. 12 Exemplary conjugate of six repeat-motif-molecules and one non-repeat-motif-molecule.
Figure 13:
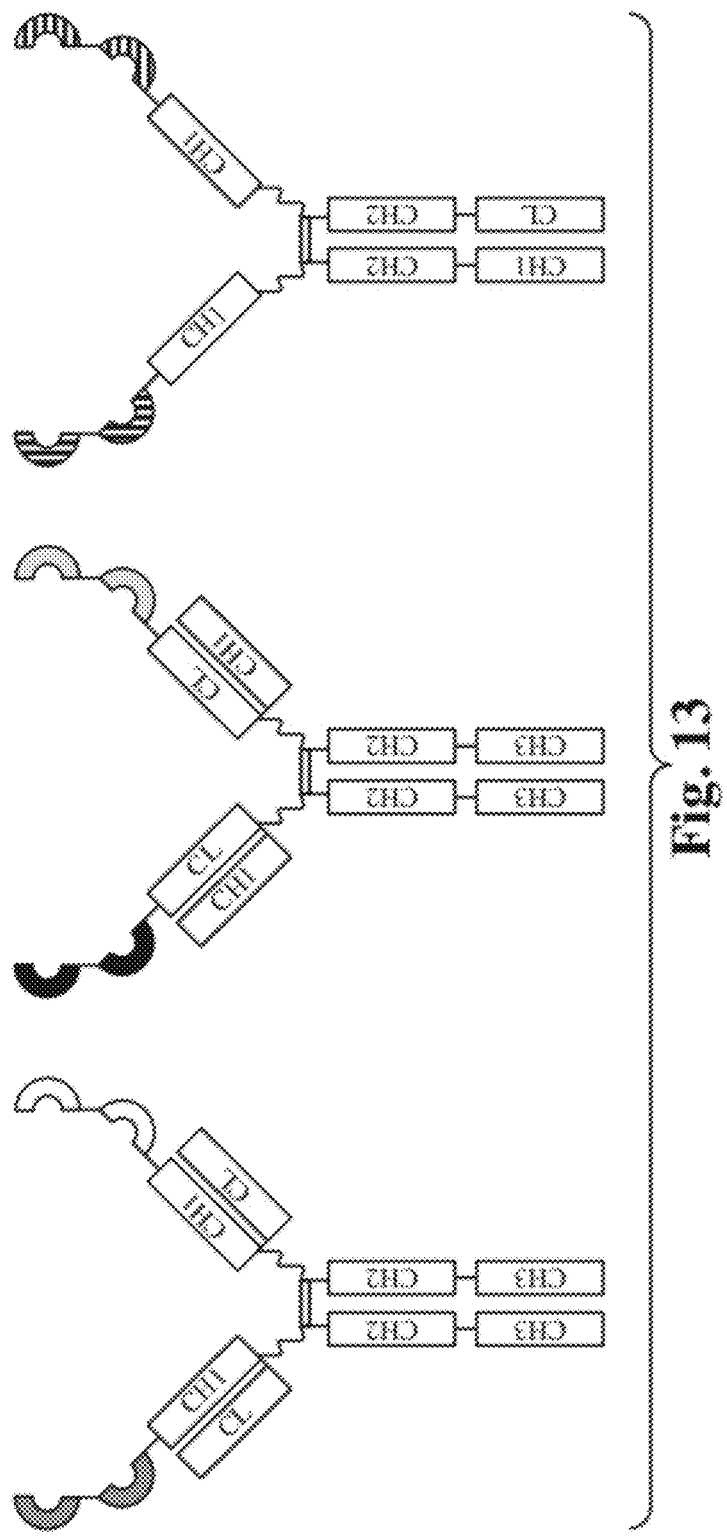
FIG. 13 Exemplary domain exchanged GEMOCs.
Figure 14:
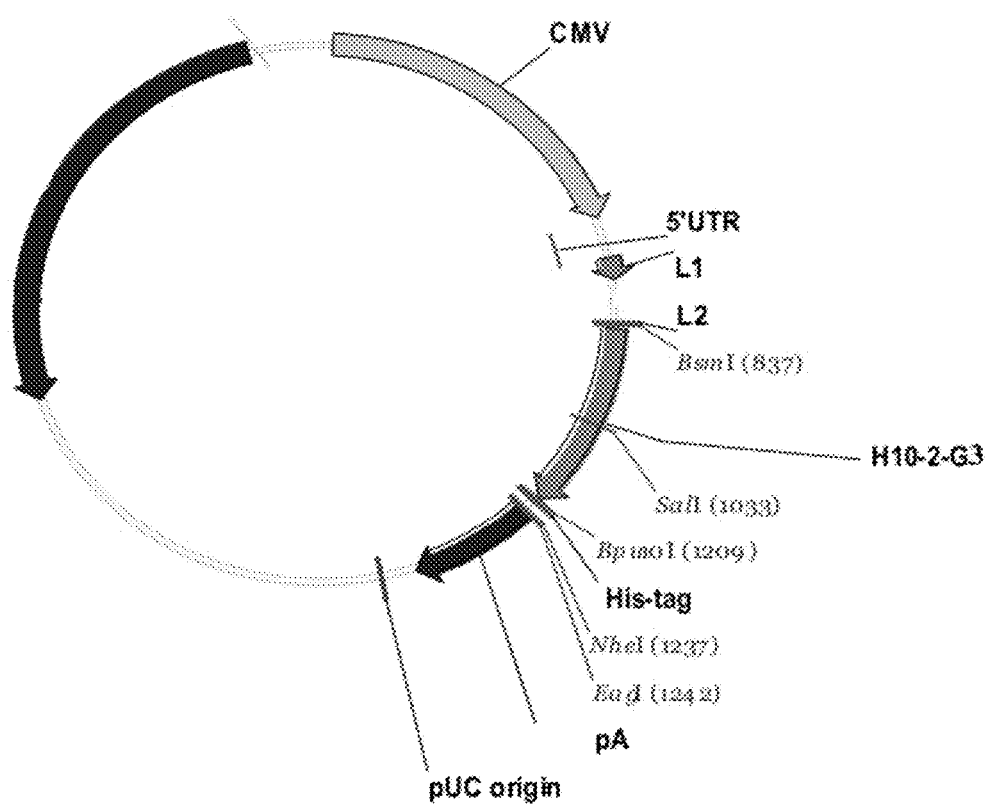
FIG. 14 Plasmid map of expression plasmids 9800.

The plasmid map of expression plasmids 9800 and 9803 accordingly, is shown in FIG. 14. The amino acid sequences of the mature (without signal sequence) conjugates are denoted in SEQ ID NO: 10 and 12.

Expression Plasmids 9801 and 9804

A gene segment encoding conjugate of SEQ ID NO: 11 or SEQ ID NO: 13 was cloned into a specified expression plasmid via the unique restriction sites HindIII and Pm1I. The expression plasmid was designed to conjugate the conjugate to the N-terminus of the hinge region of an immunoglobulin of class IgG1, thereby replacing the naturally present VH and CH1 domains. The resulting expression plasmid was useful for the expression of the conjugates of SEQ ID NO: 11 and 13, respectively, e.g. in HEK293 cells. Beside the expression cassette for the repeat-motif-molecule conjugated to the IgG1-hinge, -CH2 and -CH3 sequences the plasmid comprises:
- an origin of replication from the vector pUC 18 which allows replication of this plasmid in *E. coli*, and
- a β-lactamase gene which confers ampicillin resistance in *E. coli*.

The transcription unit of the repeat-motif-molecule-hinge-CH2-CH3 conjugate is composed of the following elements:
- the immediate early enhancer and promoter from the human cytomegalovirus,
- the Intron A sequence of the human cytomegalovirus,
- a 5'-untranslated region of a human antibody germline gene,
- a murine immunoglobulin heavy chain signal sequence including a signal sequence intron (signal sequence 1, intron, signal sequence 2 [L1-intron-L2]) and the unique restriction site BsmI at the 3' end of L2,
- the conjugate's encoding sequence,
- sequences encoding the hinge region, the CH2- and CH3-domain of human IgG1, with a unique Pm1I restriction site in the hinge region to allow cloning of the conjugate's encoding sequence, and
- a polyadenylation ("poly A") signal sequence.

Figure 15:
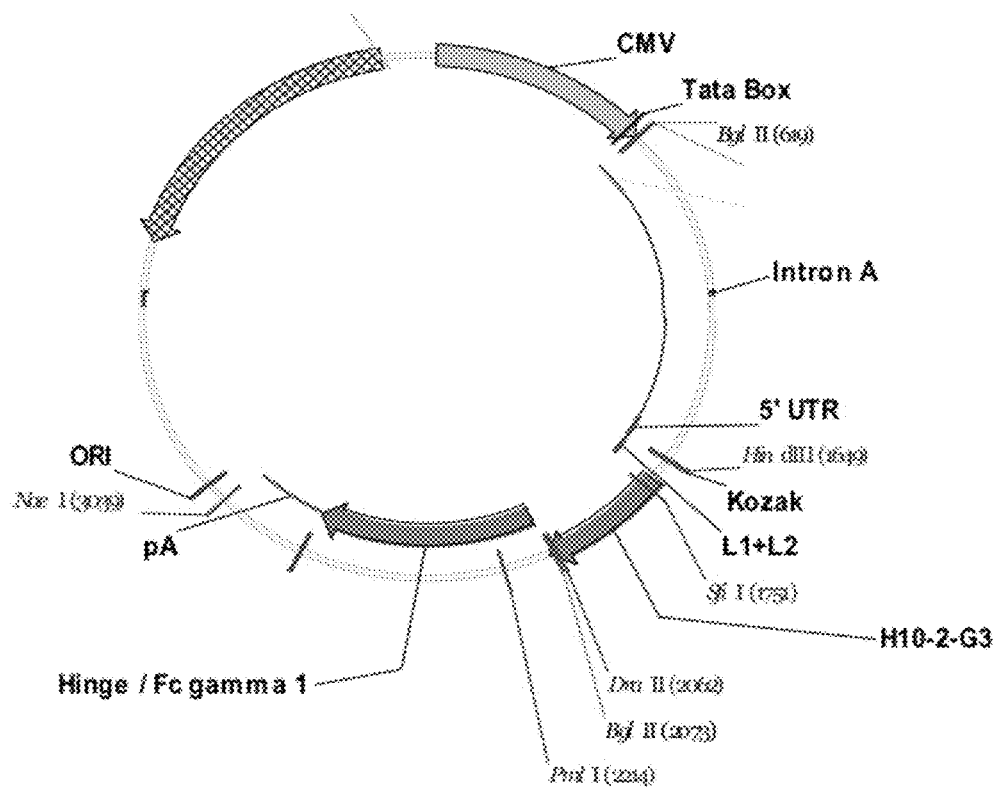
FIG. 15 Plasmid map of the expression plasmid 9801.
Figure 16:
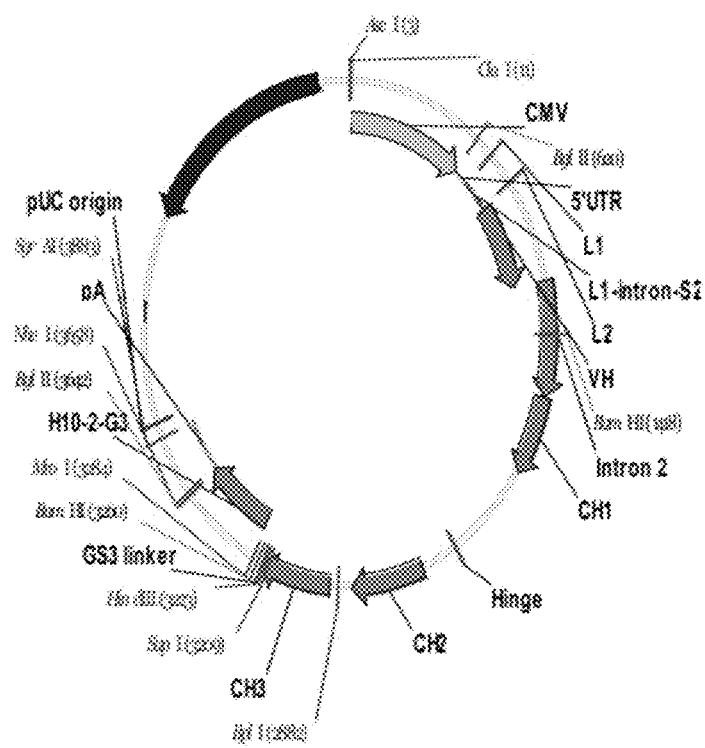
FIG. 16 Plasmid map of the heavy chain-polypeptide-conjugate expression plasmid 9807.

The plasmid map of the expression plasmid 9801, and 9804 accordingly, is shown in FIG. 15. The amino acid sequences of the mature (without signal sequence) conjugates are shown in SEQ ID NO: 11 and 13.

Expression Plasmids 9807 and 9808

An example antibody with which the repeat-motif-molecules of SEQ ID NO: 10 and 12 without hexa-histidine-tag can be conjugated is an antibody against the amyloid β-A4 peptide (anti-Aβ antibody). Such an antibody and the corresponding nucleic acid sequences are, for example, reported in WO 2003/070760 or US 2005/0169925. A gene segment encoding the conjugate was cloned into a specified expression plasmid via the unique restriction sites MroI and NheI. The expression plasmid was designed to conjugate the polypeptide to the C-terminus of a human immunoglobulin heavy chain of the subclass IgG1 (genomically organized expression cassette; exon-intron organization). The resulting expression plasmid was useful for the expression of the conjugates e.g. in HEK293 cells. Beside the expression cassette of the heavy chain of a monoclonal antibody-repeat-motif-molecule conjugate the plasmid comprises:
- an origin of replication from the vector pUC18 which allows replication of this plasmid in *E. coli*, and
- a β-lactamase gene which confers ampicillin resistance in *E. coli*.

The transcription unit of the heavy chain-repeat-motif-molecule conjugate is composed of the following elements:
- the immediate early enhancer and promoter from the human cytomegalovirus,
- a 5'-untranslated region of a human antibody germline gene,
- a murine immunoglobulin heavy chain signal sequence including a signal sequence intron (signal sequence 1, intron, signal sequence 2 [L1-intron-L2]),
- an anti-Ab antibody variable heavy chain domain encoding segment arranged with a splice donor site and a unique BamHI restriction site at the 3'-end,
- a nucleic acid encoding the human γ1 constant domains CH1, hinge, CH2 and CH3 separated by introns,
- a (G4S)3 linker fused in frame to the 3' end of the CH3 domain,
- the unique restriction sites MroI and NheI at the linker's 3' end to allow the cloning of the polypeptide in frame to the C-terminus of the linker, and
- a polyadenylation ("poly A") signal sequence.

The plasmid map of the heavy chain-repeat-motif-molecule conjugate expression plasmid 9807, and 9808 accordingly, is shown in FIG. 15.

Expression Plasmid 5170

For the expression of the light chain of the antibody the plasmid 5170 was used. Plasmid 5170 is an expression plasmid e.g. for transient expression of an antibody light chain (genomically organized expression cassette; exon-intron organization) in HEK293 cells.

Beside the antibody K-light chain expression cassette this plasmid comprises:
- a neomycine resistance gene as a selectable marker,
- an origin of replication from the vector pUC18 which allows replication of this plasmid in *E. coli*, and
- a β-lactamase gene which confers ampicillin resistance in *E. coli*.

The transcription unit of the antibody K-light chain gene is composed of the following elements:
- the immediate early enhancer and promoter from the human cytomegalovirus,
- a 5'-untranslated region of a human antibody germline gene, a murine immunoglobulin heavy chain signal sequence including a signal sequence intron (signal sequence 1, intron, signal sequence 2 [L1-intron-L2]), an anti-Aβ antibody variable light chain domain encoding segment arranged with a splice donor site and a unique BamHI restriction site at the 3'-end, a truncated human κ-light chain intron 2, the human κ-light gene constant domain, a polyadenylation ("poly A") signal sequence, and the unique restriction sites AscI and SgrAI at the 3'-end.

Figure 17:
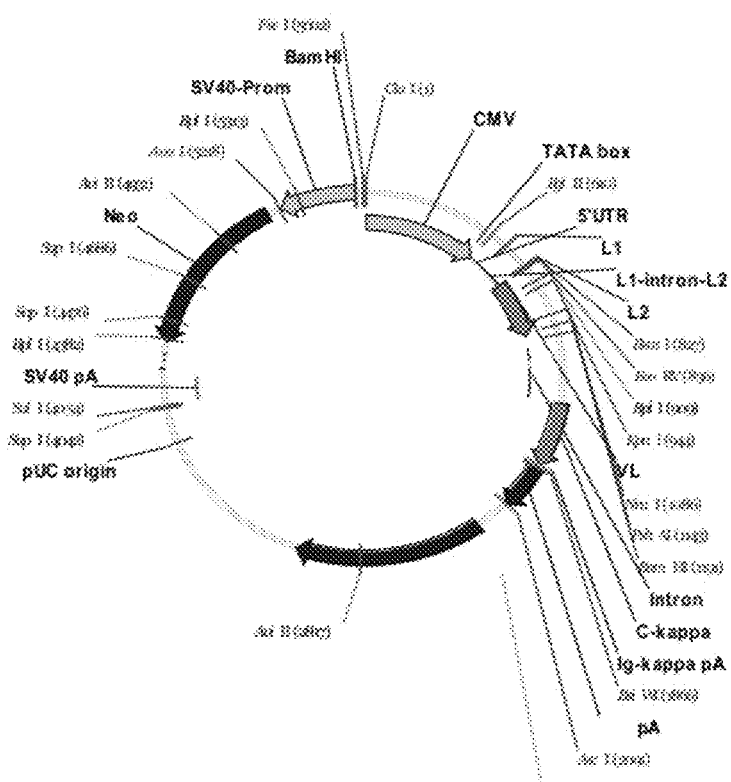
FIG. 17 Plasmid map of the antibody light chain expression vector 5170.

The plasmid map of the antibody κ-light chain expression vector 5170 is shown in FIG. 17.

EXAMPLE 2

Transient Transfection and Expression

Recombinant conjugates according to the invention as exemplified in Example 1 were obtained by transient transfection of HEK293-Freestyle cells (human embryonic kidney cell line 293, Invitrogen) growing in suspension. The transfected cells were cultivated in F17 medium (Gibco) or Freestyle 293 medium (Invitrogen), supplemented with 6 mM Glutamine, either Ultra-Glutamine (Biowhittake/Lonza) or L-Glutamine (Sigma), with 8% $CO_2$ at 37° C. in shake flasks in the scale of 30 ml to 250 ml medium. For transfection Fectin (Invitrogen) was used in a ratio of reagent (μl) to DNA (μg) of 4:3. In the case of conjugates to the C-terminus of an antibody heavy chain, light and heavy chains were expressed from two different plasmids using a molar ratio of light chain to heavy chain encoding plasmid ranging from 1:2 to 2:1, respectively. The conjugate containing cell culture supernatants were harvested at day 6 to 8 after transfection. General information regarding the recombinant expression of human immunoglobulins in e.g. HEK293 cells is given in: Meissner, P. et al., Biotechnol. Bioeng. 75 (2001) 197-203.

EXAMPLE 3

Expression Analysis Using SDS-PAGE

LDS sample buffer, fourfold concentrate (4×LDS): 4 g glycerol, 0.682 g TRIS (tris-(hydroxymethyl)-aminomethane), 0.666 g TRIS-HCl (tris-(hydroxymethyl)-aminomethane-hydrochloride), 0.8 g LDS (lithium dodecyl sulfate), 0.006 g EDTA (ethylene diamin tetra acid), 0.75 ml of a 1% by weight (w/w) solution of Serva Blue G250 in water, 0.75 ml of a 1% by weight (w/w) solution of phenol red, add water to make a total volume of 10 ml.

Figure 18:
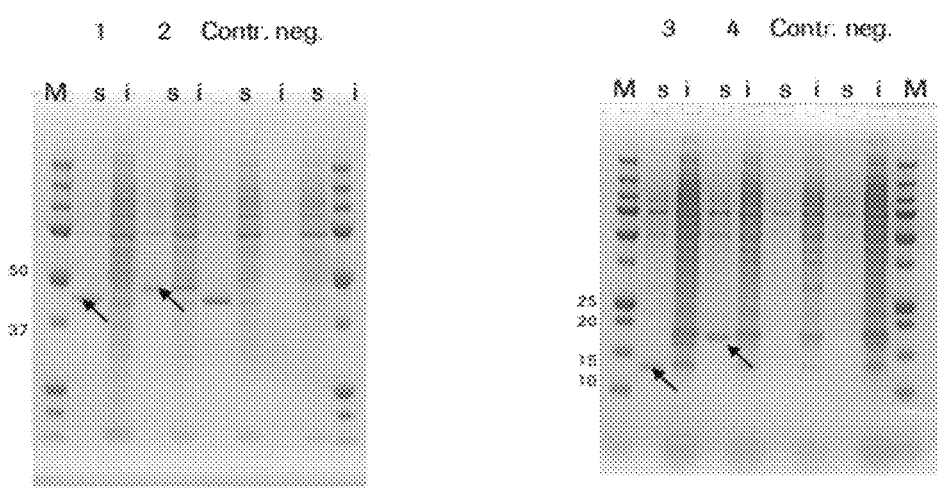
FIG. 18 SDS-PAGE gels of expressed ankyrin-repeat-motif-molecule conjugates in the supernatant of transiently transfected HEK293 cells on day 7; Construct 1=protein of SEQ ID NO: 10, construct 2=protein of SEQ ID NO: 12, construct 3=protein of SEQ ID NO: 11, construct 4=protein of SEQ ID NO: 13.

The culture broth containing the secreted conjugate was centrifuged to remove cells and cell debris. An aliquot of the clarified supernatant was admixed with 1/4 volumes (v/v) of 4×LDS sample buffer and 1/10 volume (v/v) of 0.5 M 1,4-dithiothreitol (DTT). Then the samples were incubated for 10 min. at 75° C. and protein separated by SDS-PAGE. The NuPAGE® Pre-Cast gel system (Invitrogen) was used according to the manufacturer's instruction. In particular, 10% NuPAGE® Novex® Bis-TRIS Pre-Cast gels (pH 6.4) and a NuPAGE® MES running buffer was used. The polypeptides and polypeptide-conjugates could be clearly detected (see FIG. 18).

EXAMPLE 4

Protein Purification by Affinity Chromatography and Gel Filtration Chromatography Fc- and Antibody-conjugates The expressed and secreted Fc- and antibody-conjugates were purified by affinity chromatography using the protein A affinity material MabSelectSure (GE Healthcare). Briefly, after centrifugation (10,000 g for 10 minutes) and filtration through a 0.45 μm filter the conjugate containing clarified culture supernatants was applied on a MabSelectSure column equilibrated with PBS buffer (10 mM $Na_2HPO_4$, 1 mM $KH_2PO_4$, 137 mM NaCl and 2.7 mM KCl, pH 7.4). Unbound proteins were removed by washing with equilibration buffer. The conjugate was eluted with 0.1 M citrate buffer, pH 3.3, and the product containing fractions were neutralized with 1 M TRIS pH 9.0. Afterwards, the solution was dialyzed against PBS buffer at 4° C., concentrated with an Amicon Centricon concentration device, and stored in an ice-water bath at 0° C. Aggregation of the Fc- and antibody-conjugates was analyzed by analytical size exclusion chromatography. Fractions showing high molecular weight aggregates were subjected to preparative size exclusion chromatography. Briefly, the buffer of the conjugate was exchanged to histidine buffer (20 mM histidine, 140 mM NaCl, pH 6.0) by repeated concentration and dilution in a Centricon device (Amicon). After concentration to 1-4 ml, the conjugate containing solution was applied to a Superdex200 High Load column (GE HealthCare) equilibrated with the same histidine buffer. Fractions of 1 ml were collected. All fractions were analyzed by analytical SEC (Superdex200, GE HealthCare) and fractions with purely monomeric conjugate were pooled. The integrity of the conjugates were analyzed by SDS-PAGE in the presence and absence of a reducing agent and staining with Coomassie brilliant blue as described in the previous paragraph.

Conjugates of SEQ ID NO: 10 and 12

The expressed and secreted conjugates comprising an hexa-histidine-tag (SEQ ID NO: 10 and 12) were purified by affinity chromatography using Nickel chelating affinity material Ni-Sepharose HP HighTrap (GE Healthcare) according to known methods. Briefly, after centrifugation (10,000 g for 10 minutes) and filtration through a 0.45 μm filter the conjugate containing clarified culture supernatant was applied on a Ni-Sepharose column equilibrated with phosphate buffer (50 mM $Na_3PO_4$, 300 mM NaCl, pH 8.0). Unbound proteins were removed by washing with phosphate equilibration buffer containing 20 mM imidazole. The conjugate was eluted with a conductivity gradient. Afterwards, the conjugate containing solution was extensively dialyzed against histidine buffer (20 mM histidine, 140 mM NaCl, pH 6.0) at 4° C., concentrated with an Amicon Centricon concentration device, and stored in an ice-water bath at 0° C. Aggregation of the Fc- and antibody-conjugates was analyzed by analytical size exclusion chromatography. Fractions showing high molecular weight aggregates were subjected to preparative size exclusion chromatography according to known methods. Briefly, the concentrated conjugate containing solution was applied to a Superdex200 High Load column (GE HealthCare) equilibrated with the same histidine buffer as reported above. Fractions of 1 ml were collected. All fractions were analyzed by analytical SEC (Superdex200, GE HealthCare) and fractions with purely monomeric conjugate were pooled. The integrity of the conjugate were analyzed by SDS-PAGE in the presence and absence of a reducing agent and staining with Coomassie brilliant blue as described in the previous paragraph.

EXAMPLE 5

Binding Assay by BIAcore

Figure 19:
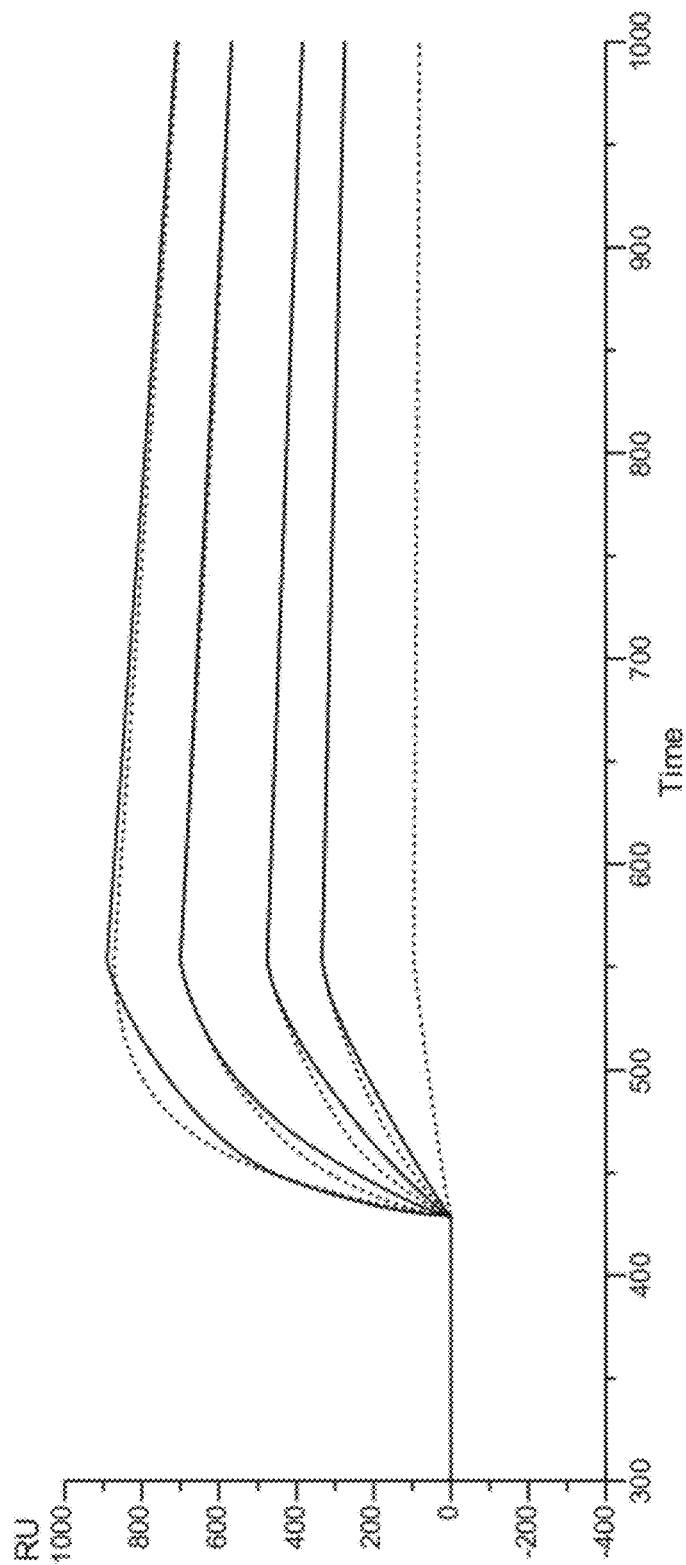
FIG. 19 BIAcore analysis of the binding of GEMOCs according to the invention to soluble HER2.

All surface plasmon resonance measurements were performed on a BIAcore 3000 instrument (GE Healthcare Biosciences AB, Sweden) at 25° C. Running and dilution buffer was PBS (1 mM $KH_2PO_4$, 10 mM $Na_2HPO_4$, 105 mM NaCl, 2.7 mM KCl), pH 6.0, 0.005% (v/v) Tween 20. Soluble protein A was diluted in 10 mM sodium acetate buffer, pH 5.0, and immobilized on a CM5 biosensor chip using the standard amine coupling kit (GE Healthcare Biosciences AB, Sweden) to obtain protein A surface densities of approximately 1000 RU. HBS-P (10 mM HEPES, pH 7.4, 118 mM NaCl, 0.005% surfactant P20; GE Healthcare Biosciences AB, Sweden) was used as running buffer during immobilization. The Fc- and antibody-conjugates in question were diluted with PBS, 0.005% (v/v) Tween 20, pH 6.0 to a concentration of 450 nM and injected over 3 minutes at a flow rate of 30 µl/minute. Then the soluble ligand was diluted into the same buffer to different concentrations between 70 and 680 nM and injected over 3 minutes at a flow rate of 30 µl/minute. Afterwards the sensor chip was regenerated for 1 minute with PBS, pH 8.0, 0.005% (v/v) Tween 20. Data analysis was performed with the BIAevaluation software (BIAcore, Sweden) (see FIG. 19).

EXAMPLE 6

Binding Assay by ELISA

The binding of the Fc- and antibody-conjugates were determined by means of an ELISA test (enzyme-linked immunosorbent assay). Herein a sandwich assay based on the streptavidin/biotin technology was used. A streptavidin-coated microtiter plate was used for the assay.

EXAMPLE 7

Binding Assay by FACS

The HER2 overexpressing stable cell line SK-BR-3 (ATCC #HTB-30) was cultivated in McCoy's 5a medium (PAN) supplemented with 10% fetal calf serum (FCS) and 2 mM L-glutamine. For detection of HER2 on the cell surface by the conjugate according to the invention, the cells were washed with PBS supplemented with 1% FCS as blocking reagent. The conjugate was incubated in PBS/1% FCS with the cells at 4° C. for 15 min., washed and incubated with an appropriate fluorescently labeled secondary antibody detecting the conjugate. The labeled cells were sorted by fluorescence assisted cell sorting (FACS) for the binding of the conjugate onto the cells.

What is claimed is:

1. Glycosylated ankyrin repeat-motif-molecule conjugate of the following formula (ankyrin repeat-motif-molecule–linker$_n$)$_m$–(conjugation partner)$_q$–(linker$_o$–ankyrin repeat- motif- molecule)$_p$ wherein n and o are independent of each other and independent for each value of m and p for integer values of 0 or 1;

wherein m is 1, p is 0 and q is 1, or m is 0, p is 1 and q is 1;

wherein the ankyrin repeat-motif-molecule conjugate comprises at least one oligosaccharide attached to a glycosylation site; and wherein the conjugation partner comprises an engineered pair of polypeptide chains comprising a human IgG1 heavy chain hinge region and human IgG1 CH2 and CH3 domains, wherein the conjugation partner comprises two separate polypeptide chains linked by three disulfide bonds in the hinge region, and wherein the conjugation partner does not contain a variable domain.

2. Conjugate according to claim 1, characterized in that said ankyrin-repeat-motif-molecule comprises the amino acid sequence of SEQ ID NO: 4 or a variant thereof.

3. Conjugate according to claim 1, characterized in that said linker is a peptidic linker selected from SEQ ID NO: 14 and SEQ ID NO: 25 to SEQ ID NO: 33.

4. Conjugate according to claim 1, characterized in that said conjugation partner is a multimerizing conjugation partner.

5. Conjugate according to claim 1, characterized in that
i) n=1, m=1, q=1, p=0, or
ii) n=0, m=1, q=1, p=0.

6. Conjugate according to claim 1, characterized in that
i) m=0, q=1, p=1, o=0, or
ii) m=0, q=1, p=1, o=1.

7. Conjugate according to claim 1, characterized in that said conjugation partner comprises the amino acid residues 121 to 352 of SEQ ID NO:11.

8. Conjugate according to claim 7, characterized in that said linker is a peptidic linker selected from SEQ ID NO: 18 to SEQ ID NO: 24.

* * * * *